United States Patent
Akahane et al.

(10) Patent No.: US 6,355,640 B1
(45) Date of Patent: *Mar. 12, 2002

(54) PYRAZOLOPYRIDINE ADENOSINE ANTAGONISTS

(75) Inventors: Atsushi Akahane, Hyogo; Shintaro Nishimura, Settsu; Hiromichi Itani, Hyogo, all of (JP); Kieran P. M. Durkin, Folsom, CA (US)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/072,696

(22) Filed: May 6, 1998

Related U.S. Application Data

(63) Continuation of application No. 08/663,119, filed as application No. PCT/JP94/02230 on Dec. 26, 1994, now Pat. No. 5,773,530.

(30) Foreign Application Priority Data

Dec. 29, 1993 (GB) ............................................. 9326524
Mar. 4, 1994 (GB) ............................................. 9404323

(51) Int. Cl.$^7$ .................... A61K 31/495; A61K 31/535; A61P 25/00; C07D 401/00; C07D 413/00
(52) U.S. Cl. ............... 514/252.06; 514/63; 514/217.05; 514/228.2; 514/228.8; 514/233.2; 540/598; 544/58.4; 544/96; 544/114; 544/229; 544/238
(58) Field of Search .......................... 514/228.2, 228.8, 514/233.2, 217.05, 252.06, 63; 540/598; 544/58.4, 96, 114, 238, 229

(56) References Cited

U.S. PATENT DOCUMENTS

| | | | | | |
|---|---|---|---|---|---|
| 4,985,444 A | * | 1/1991 | Shiokawa et al. | ........... | 514/300 |
| 5,155,114 A | * | 10/1992 | Shiokawa et al. | ........... | 514/300 |
| 5,204,346 A | * | 4/1993 | Shiokawa et al. | ....... | 514/234.5 |
| 5,773,530 A | * | 6/1998 | Akahane et al. | ............ | 544/238 |
| 6,214,843 B1 | * | 4/2001 | Kadowaki et al. | .......... | 514/322 |

OTHER PUBLICATIONS

Grant, R., Grant & Hackh Chemical Dictionary, 4th edition, p. 299, 1987.*

* cited by examiner

*Primary Examiner*—Brenda Coleman
(74) *Attorney, Agent, or Firm*—Oblon, Spivak, McClelland, Maier & Neustadt, P.C.

(57) ABSTRACT

The present invention relates to a novel pyrazolopyridine compound of the following formula:

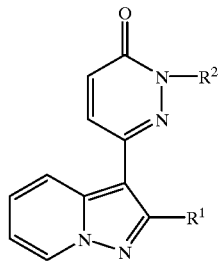

wherein $R^1$ is aryl, and $R^2$ is cyclo(lower)alkyl which may have one or more suitable substituent(s), etc;

and a pharmaceutically acceptable salt thereof, which is useful as a medicament; the processes for the preparation of said pyrazolopyridine compound or a salt thereof; a pharmaceutical composition comprising said pyrazolopyridine compound or a pharmaceutically acceptable salt thereof; etc.

7 Claims, No Drawings

PYRAZOLOPYRIDINE ADENOSINE ANTAGONISTS

This application is a continuation of U.S. Ser. No. 08/663,119, filed Sep. 13, 1996, now U.S. Pat. No. 5,773,530, which was filed as International Application Serial No. PCT/JP94/02230, filed Dec. 26, 1994.

TECHNICAL FIELD

The present invention relates to a novel pyrazolopyridine compound or a pharmaceutically acceptable salt thereof which are useful as a medicament.

1. Background Art

Some pyrazolopyridine compounds to be useful as psychostimulant, antihypertensive agent, remedy for renal failure, diuretics or the like are known (e.g. EP-0299209, EP-0379979, etc).

2. Disclosure of Invention

The present invention relates to a novel pyrazolopyridine compound and a pharmaceutically acceptable salt thereof useful as a medicament; the processes for the preparation of said pyrazolopyridine compound or a salt thereof; a pharmaceutical composition comprising, as an active ingredient, said pyrazolopyridine compound or a pharmaceutically acceptable salt thereof; a use of said pyrazolopyridine compound or a pharmaceutically acceptable salt thereof as a medicament; and a method for using said pyrazolopyridine compound for the therapeutic purpose, which comprises administering said pyrazolopyridine compound or a pharmaceutically acceptable salt thereof to a human being or an animal.

The pyrazolopyridine compound or a pharmaceutically acceptable salt thereof is an adenosine antagonist (especially, $A_1$ receptor antagonist) and possesses various pharmacological actions such as cognitive enhancing action, analgesic action, locomotor action, antidepressant action, diuretic action, cardioprotective effect, cardiotonic action, vasodilating action (e.g. cerebral vasodilating action, etc), the action of increasing the renal blood flow, renal protective effect, improvement of renal function, enhancing action of lipolysis, inhibition of anaphylactic bronchoconstriction, acceleration of the insulin release, the action of increasing the production of erythropoietin, inhibiting action of platelet aggregation, or the like; useful as cognitive enhancer, anti-dementia drug, psychostimulant, analgesic, cardioprotective agent, antidepressant, ameliorants of cerebral circulation, tranquilizer, drug for heart failure, cardiotonic agent, antihypertensive agent, drug for renal failure (renal insufficiency), drug for renal toxicity, renal protective agent, drug for improvement of renal function, diuretic, drug for edema, antiobesity, antiasthmatic, bronchodilator, drug for apnea, drug for gout, drug for hyperuricemia, drug for sudden infant death syndrome (SIDS), ameliorants of immunosuppressive action of adenosine, antidiabetic agent, drug for ulcer, drug for pancreatitis, drug for Ménière's syndrome, drug for anemia; drug for thrombosis, drug for myocardial infarction, drug for obstruction, drug for arteriosclerosis obliterans, drug for thrombophlebitis, drug for cerebral infarction, drug for transient ischemic attack, drug for angina pectoris, or the like; and useful for the prevention and/or treatment of depression, dementia (e.g. Alzheimer's disease, cerebrovascular dementia, Parkinson's disease, etc), anxiety, pain, cerebrovascular disease (e.g. stroke, etc), heart failure; hypertension (e.g. essential hypertension, nephrogenous hypertension, etc); circulatory insufficiency (acute circulatory insufficiency) cuased by, for example, the ischemia/reperfusion injury (e.g. myocardial ischemia/reperfusion injury, cerebral ischemia/reperfusion injury, peripheral ischemia/reperfusion injury, etc), shock (e.g. endotoxin shock, hemorrhagic shock, etc), surgical procedure, or the like; post-resuscitation asystole; bradyarrhythmia; electro-mechanical dissociation; hemodynamic collapse; SIRS (systemic inflammatory response syndrome); multiple organ failure; renal failure (renal insufficiency) (e.g. acute renal failure, etc), renal toxicity [e.g. renal toxicity induced by a drug such as cisplatins, gentamicin, FR-900506 (disclosed in EP-0184162), cyclosporin (e.g. cyclosporin A) or the like; glycerol, etc], nephrosis, nephritis, edema (e.g. cardiac edema, nephrotic edema, hepatic edema, idiopathic edema, drug edema, acute angioneurotic edema, hereditary angioneurotic edema, carcinomatous ascites, gestational edema, etc); obesity, bronchial asthma, gout, hyperuricemia, sudden infant death syndrome, immunosuppression, diabetes, ulcer such as peptic ulcer (e.g. gastric ulcer, duodenal ulcer, etc), pancreatitis, Ménière's syndrome, anemia; myocardial infarction, thrombosis (e.g. arterial thrombosis, cerebral thrombosis, etc), obstruction, arteriosclerosis obliterans, thrombophlebitis, cerebral infarction, transient ischemic attack, angina pectoris, or the like.

The novel pyrazolopyridine compound of the present invention can be shown by the following formula (I).

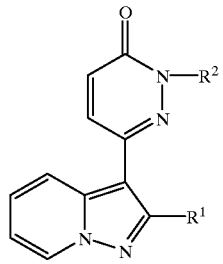

(I)

wherein $R^1$ is aryl, and $R^2$ is cyclo(lower)alkyl which may have one or more suitable substituent(s);
cyclo(lower)alkenyl which may have one or more suitable substituent(s);
lower alkyl substituted with aryl and acyl;
aryl which may have one or more suitable substituent(s);
saturated 3 to 8-memberd heteromonocyclic group containing 1 to 4 nitrogen atom(s) which may have one or more suitable substituent(s);
unsaturated 3 to 8-membered heteromonocyclic group containing 1 to 4 nitrogen atom(s) which may have one or more suitable substituent(s);
saturated 3 to 8-membered heteromonocyclic group containing 1 to 4 oxygen atom(s) which may have one or more suitable substituent(s); or
saturated condensed heterocyclic group containing 1 to 4 oxygen atom(s) which may have one or more suitable substituent(s).

The object compound (I) or a salt thereof of the present invention can be prepared by the following reaction schemes.
Process 1
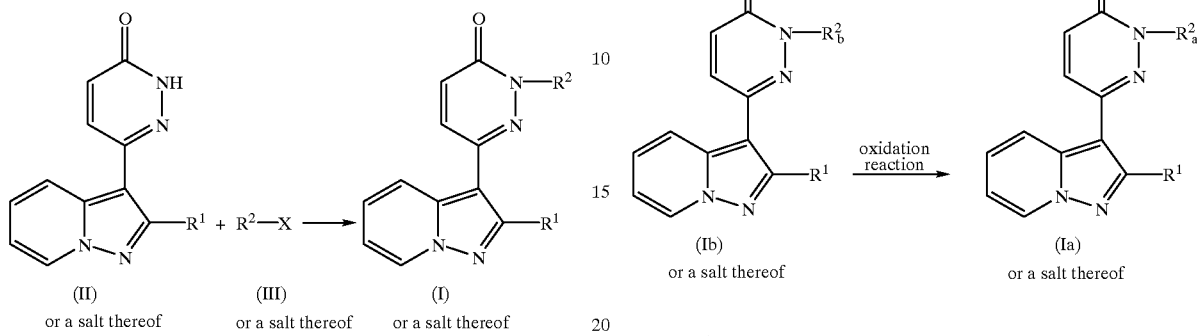
Process 2
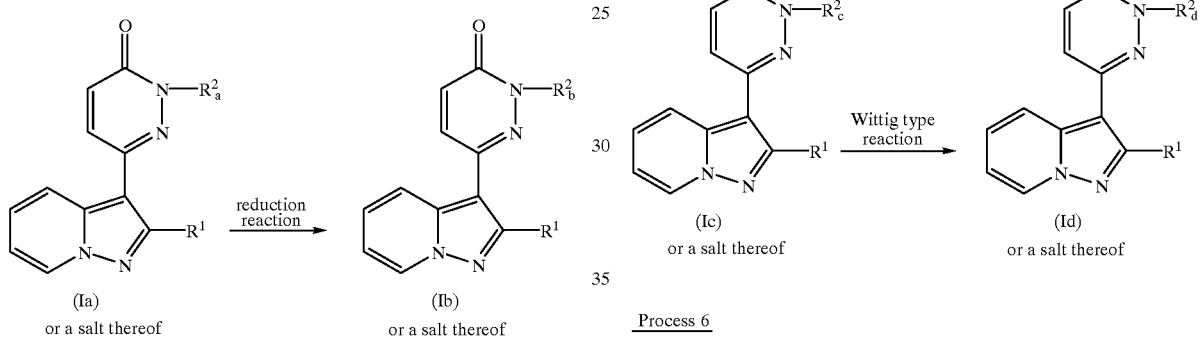
Process 3
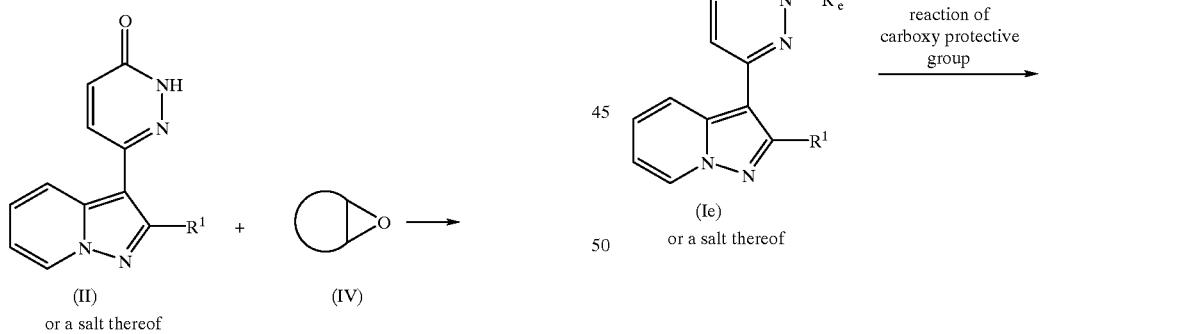
Process 4
Process 5
Process 6

Process 7

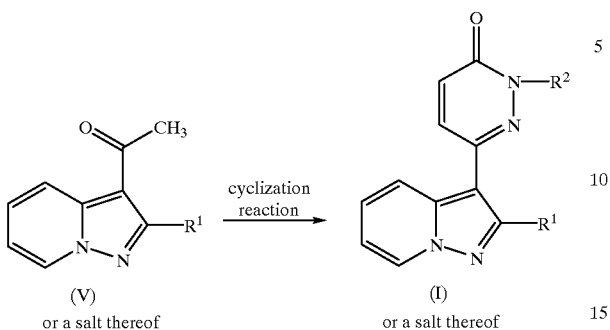

(V) or a salt thereof → (I) or a salt thereof
cyclization reaction

Process 8

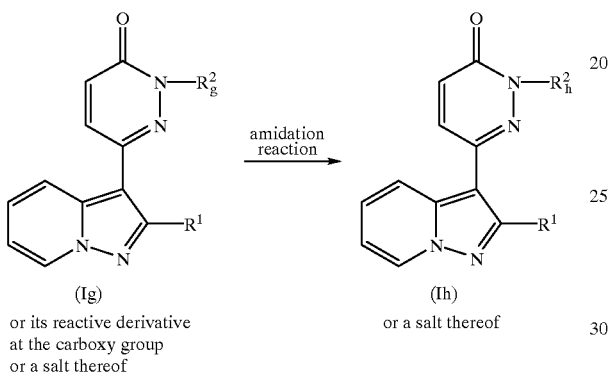

(Ig) or its reactive derivative at the carboxy group or a salt thereof → (Ih) or a salt thereof
amidation reaction wherein
R$^1$ and R$^2$ are each as defined above,
R$_a^2$ is cyclo(lower)alkyl having oxo, which may have one or more suitable substituent(s);
cyclo(lower)alkenyl having oxo, which may have one or more suitable substituent(s);
saturated 3 to 8-membered heteromonocyclic group containing 1 to 4 nitrogen atom(s) having oxo, which may have one or more suitable substituent(s);
unsaturated 3 to 8-membered heteromonocyclic group containing 1 to 4 nitrogen atom(s) having oxo, which may have one or more suitable substituent(s);
saturated 3 to 8-membered heteromonocyclic group containing 1 to 4 oxygen atom(s) having oxo, which may have one or more suitable substituent(s); or
saturated condensed heterocyclic group containing 1 to 4 oxygen atom(s) having oxo, which may have one or more suitable substituent(s);
R$_b^2$ is cyclo(lower)alkyl having hydroxy, which may have one or more suitable substituent(s);
cyclo(lower)alkenyl having hydroxy, which may have one or more suitable substituent(s);
saturated 3 to 8-membered heteromonocyclic group containing 1 to 4 nitrogen atom(s) having hydroxy, which may have one or more suitable substituent(s);
unsaturated 3 to 8-membered heteromonocyclic group containing 1 to 4 nitrogen atom(s) having hydroxy, which may have one or more suitable substituent(s);
saturated 3 to 8-membered heteromonocyclic group containing 1 to 4 oxygen atom(s) having hydroxy, which may have one or more suitable substituent(s); or
saturated condensed heterocyclic group containing 1 to 4 oxygen atom(s) having hydroxy, which may have one or more suitable substituent(s);

R$_c^2$ is cyclo(lower)alkyl having oxo, which may have one or more suitable substituent(s); or
cyclo(lower)alkenyl having oxo, which may have one or more suitable substituent(s),
R$_d^2$ is cyclo(lower)alkyl having lower alkylidene, which may have one or more suitable substituent(s);
cyclo(lower)alkyl having acyl(lower)alkylidene, which may have one or more suitable substituent(s);
cyclo(lower)alkyl having cyano(lower)alkylidene, which may have one or more suitable substituent(s);
cyclo(lower)alkyl having heterocyclic(lower)alkylidene, which may have one or more suitable substituent(s);
cyclo(lower)alkenyl having lower alkylidene, which may have one or more suitable substituent(s);
cyclo(lower)alkenyl having acyl(lower)alkyl, which may have one or more suitable substituent(s);
cyclo(lower)alkenyl having acyl(lower)alkylidene, which may have one or more suitable substituent(s);
cyclo(lower)alkenyl having cyano(lower)alkylidene, which may have one or more suitable substituent(s);
cyclo(lower)alkenyl having heterocyclic(lower)alkylidene, which may have one or more suitable substituent(s);
R$_e^2$ is cyclo(lower)alkyl having protected carboxy, which may have one or more suitable substituent(s);
cyclo(lower)alkyl having protected carboxy(lower)alkyl, which may have one or more suitable substituent(s);
cyclo(lower)alkyl having protected carboxy(lower)alkylidene, which may have one or more suitable substituent(s);
cyclo(lower)alkyl having N-protected carboxy(lower)alkylcarbamoyl(lower)alkyl, which may have one or more suitable substituent(s);
cyclo(lower)alkyl having N-lower alkyl-N-protected carboxy(lower)alkylcarbamoyl(lower)alkyl, which may have one or more suitable substituent(s);
cyclo(lower)alkyl having protected carboxy(lower)alkoxyimino, which may have one or more suitable substituent(s);
cyclo(lower)alkenyl having protected carboxy, which may have one or more suitable substituent(s);
cyclo(lower)alkenyl having protected carboxy(lower)alkyl, which may have one or more suitable substituent(s);
cyclo(lower)alkenyl having protected carboxy(lower)alkylidene, which may have one or more suitable substituent(s);
cyclo(lower)alkenyl having N-protected carboxy(lower)alkylcarbamoyl(lower)alkyl, which may have one or more suitable substituent(s);
cyclo(lower)alkenyl having N-lower alkyl-N-protected carboxy(lower)alkylcarbamoyl(lower)alkyl, which may have one or more suitable substituent(s);
cyclo(lower)alkenyl having protected carboxy(lower)alkoxyimino, which may have one or more suitable substituent(s);
saturated 3 to 8-membered heteromonocyclic group containing 1 to 4 nitrogen atom(s) having protected carboxy(lower)alkyl, which may have one or more suitable substituent(s);
unsaturated 3 to 8-membered heteromonocyclic group containing 1 to 4 nitrogen atom(s) having protected carboxy(lower)alkyl, which may have one or more suitable substituent(s);
saturated 3 to 8-membered heteromonocyclic group containing 1 to 4 oxygen atom(s) having protected carboxy(lower)alkyl, which may have one or more suitable substituent(s); or saturated condensed heterocyclic group containing 1 to 4 oxygen atom(s) having protected carboxy(lower)alkyl, which may have one or more suitable substituent(s);

$R_f^2$ is cyclo(lower)alkyl having carboxy, which may have one or more suitable substituent(s);

cyclo(lower)alkyl having carboxy(lower)alkyl, which may have one or more suitable substituent(s);

cyclo(lower)alkyl having carboxy(lower)alkylidene, which may have one or more suitable substituent(s);

cyclo(lower)alkyl having N-carboxy(lower)alkylcarbamoyl(lower)alkyl, which may have one or more suitable substituent(s);

cyclo(lower)alkyl having N-lower alkyl-N-carboxy(lower)alkylcarbamoyl(lower)alkyl, which may have one or more suitable substituent(s);

cyclo(lower)alkyl having carboxy(lower)alkoxyimino, which may have one or more suitable substituent(s);

cyclo(lower)alkenyl having carboxy, which may have one or more suitable substituent(s);

cyclo(lower)alkenyl having carboxy(lower)alkyl, which may have one or more suitable substituent(s);

cyclo(lower)alkenyl having carboxy(lower)alkylidene, which may have one or more suitable substituent(s);

cyclo(lower)alkenyl having N-carboxy(lower)alkylcarbamoyl(lower)alkyl, which may have one or more suitable substituent(s);

cyclo(lower)alkenyl having N-lower alkyl-N-carboxy(lower)alkylcarbamoyl(lower)alkyl, which may have one or more suitable substituent(s);

cyclo(lower)alkenyl having carboxy(lower)alkoxyimino, which may have one or more suitable substituent(s);

saturated 3 to 8-membered heteromonocyclic group containing 1 to 4 nitrogen atom(s) having carboxy(lower)alkyl, which may have one or more suitable substituent(s);

unsaturated 3 to 8-membered heteromonocyclic group containing 1 to 4 nitrogen atom(s) having carboxy(lower)alkyl, which may have one or more suitable substituent(s);

saturated 3 to 8-membered heteromonocyclic group containing 1 to 4 oxygen atom(s) having carboxy(lower)alkyl, which may have one or more suitable substituent(s); or saturated condensed heterocyclic group containing 1 to 4 oxygen atom(s) having carboxy(lower)alkyl, which may have one or more suitable substituent(s);

$R_g^2$ is cyclo(lower)alkyl having carboxy(lower)alkyl, which may have one or more suitable substituent(s);

cyclo(lower)alkyl having carboxy(lower)alkylidene, which may have one or more suitable substituent(s);

cyclo(lower)alkenyl having carboxy(lower)alkyl, which may have one or more suitable substituent(s);

cyclo(lower)alkenyl having carboxy(lower)alkylidene, which may have one or more suitable substituent(s);

$R_h^2$ is cyclo(lower)alkyl having amidated carboxy(lower)alkyl, which may have one or more suitable substituent(s);

cyclo(lower)alkyl having amidated carboxy(lower)alkylidene, which may have one or more suitable substituent(s);

cyclo(lower)alkenyl having amidated carboxy(lower)alkyl, which may have one or more suitable substituent(s);

cyclo(lower)alkenyl having amidated carboxy(lower)alkylidene, which may have one or more suitable substituent(s);

a compound of the formula

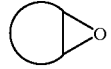

is cyclo(lower)alkane having epoxy, which may have one or more suitable substituent(s);

cyclo(lower)alkene having epoxy, which may have one or more suitable substituent(s);

saturated 3 to 8-membered heteromonocyclic compound containing 1 to 4 nitrogen atom(s) having epoxy, which may have one or more suitable substituent(s);

unsaturated 3 to 8-membered heteromonocyclic compound containing 1 to 4 nitrogen atom(s) having epoxy, which may have one or more suitable substituent(s);

saturated 3 to 8-membered heteromonocyclic compound containing 1 to 4 oxygen atom(s) having epoxy, which may have one or more suitable substituent(s); or saturated condensed heterocyclic compound containing 1 to 4 oxygen atom(s) having epoxy, which may have one or more suitable substituent(s); and X is an acid residue.

In addition to the processes as mentioned above, the object compound (I) or a salt thereof can be prepared, for example, according to the procedures as illustrated in Examples in the present specification or the similar manners thereto.

In starting compounds, there may be the novel compounds. They can be prepared, for example, according to the procedures as illustrated in Preparations in the present specification or the similar manners thereto.

It is to be noted that the object compound (I) may include the geometrical isomer(s) due to the double bond(s) and/or the stereo isomer(s) due to the asymmetric carbon atom(s). In this regard, one isomer can be converted to another according to a conventional manner in this field of the art.

Suitable pharmaceutically acceptable salts of the object compound (I) are conventional ones and include a metal salt such as an alkali metal salt (e.g. sodium salt, potassium salt, etc) and an alkaline earth metal salt (e.g. calcium, salt, magnesium salt, etc), an ammonium salt, an organic base salt (e.g. trimethylamine salt, triethylamine salt, pyridine salt, picoline salt, dicyclohexylamine salt, N,N'-dibenzylethylenediamine salt, etc), an organic acid salt (e.g. acetate, trifluoroacetate, maleate, tartrate, fumarate, methanesulfonate, benzenesulfonate, formate, toluenesulfonate, etc), an inorganic acid salt (e.g. hydrochloride, hydrobromide, hydriodide, sulfate, phosphate, etc), a salt with an amino acid (e.g. arginine, aspartic acid, glutamic acid, etc), and the like.

In the above and following descriptions of the present specification, suitable examples and illustrations of the various definitions which the present invention includes within the scope thereof are explained in detail as follows.

The term "lower" is intended to mean 1 to 6 carbon atom(s) unless otherwise indicated.

The term "higher" is intended to mean 7 to 20 carbon atoms unless otherwise indicated.

Suitable "aryl" may include phenyl, naphthyl, dihydronaphthyl (e.g., 1,2-dihydronaphthyl, 1,4- dihydronaphthyl, etc), tetrahydronaphthyl (e.g. 1,2,3,4-tetrahydronaphthyl, etc), indenyl, anthryl, and the like; in which the preferred one may be ($C_6$–$C_{10}$)aryl, and the more preferred one may be phenyl and tetrahydronaphthyl.

Said "aryl" ay nave one or more (preferably 1 to 3) suitable substituent(s) selected from the group consisting of hydroxy; oxo; lower alkoxy (e.g. methoxy, ethoxy, propoxy, butoxy, t-butoxy, pentyloxy, hexyloxy, etc); acyl(lower) alkoxy [in which the preferred one may be carboxy(lower) alkoxy or lower alkoxycarbonyl(lower)alkoxy; and the like, in which the preferred substituent(s) may be hydroxy; oxo; ($C_1$–$C_4$)alkoxy; carboxy($C_1$–$C_4$)alkoxy; or ($C_1$–$C_4$) alkoxycarbonyl($C_1$–$C_4$)alkoxy, and the more preferred one may be hydroxy; oxo; methoxy; carboxymethoxy; or methoxycarbonylmethoxy.

Suitable "lower alkyl" may include straight or branched ones such as methyl, ethyl, propyl, isopropyl, butyl, t-butyl, pentyl, hexyl or the like, in which the preferred one may be ($C_1$–$C_4$)alkyl and the more preferred one may be methyl, ethyl or propyl.

Suitable "lower alkylidene" may include methylene, ethylidene, propylidene, 1-methylethylidene, butylidene, pentylidene, hexylidene, and the like, in which the preferred one may be ($C_1$–$C_4$)alkylidene, and the more preferred one may be methylene.

Suitable "cyclo(lower)alkyl" may be cyclo($C_3$–$C_8$)alkyl such as cyclopropyl, cyclobutyl, cyclopentyl, cyclohexyl, cycloheptyl, cyclooctyl or the like, in which the preferred one may be cyclo($C_5$–$C_7$)alkyl such as cyclopentyl, cyclohexyl or cycloheptyl.

Said "cyclo(lower)alkyl" may have one or more (preferably 1 to 3) suitable substituent(s) selected from the group consisting of oxo; protected oxo (e.g. lower alkylenedioxy group such as ethylenedioxy, or the like; etc); hydroxy, protected hydroxy [e.g. acyloxy; tri(lower) alkylsilyloxy such as trimethylsilyloxy, t-butyldimethylsilyloxy, or the like; etc]; hydroxy(lower) alkyl (e.g. hydroxymethyl, 2-hydroxyethyl, 2-hydroxypropyl, 1-hydroxymethylethyl, 4-hydroxybutyl, 2-hydroxymethyl-2-methylethyl, 5-hydroxypentyl, 3-hydroxyhexyl, etc) [in which the preferred one may be hydroxy($C_1$–$C_4$)alkyl and the more preferred one may be 2-hydroxyethyl]; acyl; lower alkyl; lower alkylidene; acyl (lower)alkyl; acyl(lower)alkylidene; cyano; cyano(lower) alkyl (e.g. cyanomethyl, 2-cyanoethyl, 2-cyanopropyl, 1-cyanomethylethyl, 4-cyanobutyl, 2-cyanomethyl-2-methylethyl, 5-cyanopentyl, 3-cyanohexyl, etc) [in which the preferred one may be cyano($C_1$–$C_4$)alkyl, and the more preferred one may be cyanomethyl]; cyano(lower) alkylidene (e.g. cyanomethylene, 2-cyanoethylidene, 2-cyanopropylidene, 4-cyanobutylidene, 5-cyanopentylidene, 3-cyanohexylidene, etc) [in which the preferred one may be cyano($C_1$–$C_4$)alkylidene, and the more preferred one may be cyanomethylene]; heterocyclic(lower) alkylidene which may have one or more suitable substituent (s); hydroxyimino; lower alkoxyimino (e.g. methoxyimino, ethoxyimino, propoxyimino, butoxyimino, t-butoxyimino, pentyloxyimino, hexyloxyimino, etc) [in which the preferred one may be ($C_1$–$C_4$)alkoxyimino, and the more preferred one may be methoxyimino]; acyl(lower)alkoxyimino [in which the preferred one may be carboxy(lower) alkoxyimino or protected carboxy(lower)alkoxyimino, the more preferred one may be carboxy(lower)alkoxyimino or lower alkoxycarbonyl(lower)alkoxyimino, the much more preferred one may be carboxy($C_1$–$C_4$)alkoxyimino or ($C_1$–$C_4$)alkoxycarbonyl($C_1$–$C_4$)alkoxyimino, and the most preferred one may be carboxymethoxyimino or t-butoxycarbonylmethoxyimino]; acyloxyimino [in which the preferred one may be hydroxysulfonyloxyimino]; hydrazono; acylhydrazono [in which the preferred one may be carbamoylhydrazono]; and the like.

Suitable "cyclo(lower)alkenyl" may be cyclo($C_3$–$C_8$) alkenyl such as cyclopropenyl, cyclobutenyl, cyclopentenyl, cyclohexenyl, cycloheptenyl, cyclooctenyl or the like, in which the preferred one may be cyclo($C_5$–$C_7$)alkenyl such as cyclopentenyl, cyclohexenyl or cycloheptenyl, and the more preferred one may be cyclohexenyl or cycloheptenyl.

Said "cyclo(lower)alkenyl" may have one or more (preferably 1 to 3) suitable substituent(s) as exemplified above for those of "cyclo(lower)alkyl".

Suitable "acyl" may include lower alkanoyl (e.g. formyl, acetyl, propionyl, butyryl, isobutyryl, pivaloyl, hexanoyl, etc); carboxy; protected carboxy; hydroxysulfonyl; and the like.

Suitable "protected carboxy" may be (1) an esterified carboxy, in which concrete examples of esterified carboxy may be the ones such as lower alkoxycarbonyl (e.g. methoxycarbonyl, ethoxycarbonyl, propoxycarbonyl, sopropoxycarbonyl, butoxycarbonyl, isobutoxycarbonyl, z-butoxycarbonyl, pentyloxycarbonyl, hexyloxycarbonyl, 1-cyclopropylethoxycarbonyl, etc) which may have suitable substituent(s), for example, lower alkanoyloxy (lower)alkoxycarbonyl [e.g. acetoxymethoxycarbonyl, propionyloxymethoxycarbonyl, butyryloxymethoxycarbonyl, valeryloxymethoxycarbonyl, pivaloyloxymethoxycarbonyl, 1-acetoxyethoxycarbonyl, 1-propionyloxyettoxycarbonyl, pivaloyloxymethoxycarbonyl, 2-propionyloxyethoxycarbonyl, hexanoyloxymethoxycarbonyl, etc]; lower alkanesulfonyl(lower)alkoxycarbonyl [e.g. 2-mesylethoxycarbonyl, etc]; mono(or di or tri)halo (lower)alkoxycabronyl [e.g. 2-iodoethoxycarbonyl, 2,2,2-trichloroethoxycarbonyl, etc]; lower alkenyloxycarbonyl [e.g. vinyloxycarbonyl, allyloxycarbonyl, etc]; lower alkynyloxycarbonyl [e.g. ethynyloxycarbonyl, propynyloxycarbonyl, etc]; ar(lower)alkoxycarbonyl [preferably mono- (or di- or tri-)phenyl(lower)alkoxycarbonyl] which may have suitable substituent s) [e.g. benzyloxycarbonyl, 4-methoxybenzyloxycarbonyl, 4-nitrobenzyloxycarbonyl, phenethyloxycarbonyl, trityloxycarbonyl, benzhydryloxycarbonyl, bis (methoxyphenyl)methoxycarbonyl, 3,4-dimethoxybenzyloxycarbonyl, 4-hydroxy-3,5-di-t-butylbenzyloxycarbonyl, etc]; aryloxycarbonyl which may have suitable substituent(s) [e.g. phenoxycarbonyl, 4-chlorophenoxycarbonyl, tolyloxycarbonyl, 4-t-butylphenoxycarbonyl, xyloxycarbonyl, mesityloxycarbonyl, cumenyloxycarbonyl, etc]; or the like;

(2) amidated carboxy, in which concrete examples of amidated carboxy may be carbamoyl; N-(lower) alkylcarbamoyl (e.g. N-methylcarbamoyl, N-ethylcarbamoyl, N-isopropylcarbamoyl, N-butylcarbamoyl, N-pentylcarbamoyl, N-hexylcarbamoyl, etc);

N-(higher)alkylcarbamoyl (e.g. N-heptylcarbamoyl, N-(2-methylhepryl)carbamoyl, N-nonylcartbamoyl, N-decanylcarbamoyl, N-tricyclo[3.3.1.1$^{3,7}$]-decanylcarbamoyl, N-undecanylcarbamoyl, N-(bicyclo[4.3.2]urdecanyl)carbamoyl, N-dodecanylcarbamoyl, N-tridecanylcarbamoyl, N-tetradecanylcarbamoyl, N-pentadecanylcarbamoyl, N-hexadecanylcarbamoyl, N-heptadecanylcarbamoyl, N-octadecanylcarbamoyl, N-nonadecanylcarbamoyl, N-icosanylcarbamoyl, etc);

N,N-di(lower)alkylcarbamoyl [e.g. N,N-dimethylcarbamoyl, N,N-diethylcarbamoyl, N-methyl-N-ethylcarbamoyl, N,N-dipropylcarbamoyl, N,N-di(t-butyl)carbamoyl, N-pentyl-N-hexylcarbamoyl, etc];

N-lower alkyl-N-ar(lower)alkylcarbamoyl (e.g. N-methyl-N-benzylcarbamoyl, etc);

N-carboxy(lower)alkylcarbamoyl [e.g. N-carboxymethylcarbamoyl, N-(2-carboxyethyl)carbamoyl, N-(2-carboxypropyl)carbamoyl, N-(3-carboxypropyl)carbamoyl, N-(1-carboxymethylethyl)carbamoyl, N-(4-carboxybutyl)carbamoyl, N-(2-carboxymethyl-2-methylethyl)carbamoyl, N-(5-carboxypentyl)carbamoyl, N-(3-carboxyhexyl)carbamoyl, etc];

N-protected carboxy(lower)alkylcarbamoyl, in which the preferred one may be N-esterified carboxy(lower)alkylcarbamoyl, and the more preferred one may be N-lower alkoxycarbonyl(lower)alkylcarbamoyl [e.g. N-(methoxycarbonylmethyl)carbamoyl, N-(ethoxycarbonylmethyl)carbamoyl, N-(2-ethoxycarbonylethyl)carbamoyl, N-(2-t-butoxycarbonylethyl)carbamoyl, N-(3-methoxycarbonylpropyl)carbamoyl, N-(1-propoxycarbonylpropyl)carbamoyl, N-(1-isopropoxycarbonylmethylethyl)carbamoyl, N-(butoxycarbonylmethyl)carbamoyl, N-(t-butoxycarbonylmethyl)carbamoyl, N-(4-isobutoxycarbonylbutyl)carbamoyl, N-(2-t-butoxycarbonylmethyl-2-methylethyl)carbamoyl, N-(3-pentyloxycarbonylpentyl)carbamoyl, N-(6-hexyloxycarbonylhexyl)carbamoyl, N-[(1-cyclopropylethoxy)carbonylmethyl]carbamoyl, etc];

N-lower alkyl-N-carboxy(lower)alkylcarbamoyl [e.g. N-methyl-N-(carboxymethyl)carbamoyl, N-methyl-N-(2-carboxyethyl)carbamoyl, N-ethyl-N-(2-carboxypropyl)carbamoyl, N-propyl-N-(3-carboxypropyl)carbamoyl, N-isopropyl-N-(1-carboxymethylethyl)carbamoyl, N-butyl-N-(4-carboxybutyl)carbamoyl, N-t-butyl-N-(2-carboxymethyl-2-methylethyl)carbamoyl, N-pentyl-N-(5-carboxypentyl)carbamoyl, N-hexyl-N-(3-carboxyhexyl)carbamoyl, etc];

N-lower alkyl-N-protected carboxy(lower)alkylcarbamoyl, in which the preferred one may be N-lower alkyl-N-esterified carboxy(lower)alkylcarbamoyl, and the more preferred one may be N-lower alkyl-N-lower alkoxycarbonyl(lower)alkylcarbamoyl [e.g. N-methyl-N-(methoxycarbonylmethyl)carbamoyl, N-methyl-N-(ethoxycarbonylmethyl)carbamoyl, N-methyl-N-(2-ethoxycarbonylethyl)carbamoyl, N-ethyl-N-(2-t-butoxycarbonylethyl)carbamoyl, N-propyl-N-(3-methoxycarbonylpropyl)carbamoyl, N-isopropyl-N-(1-propoxycarbonylpropyl)carbamoyl, N-propyl-N-(1-isopropoxycarbonylmethylethyl)carbamoyl, N-butyl-N-(butoxycarbonylmethyl)carbamoyl, N-isobutyl-N-(t-butoxycarbonylmethyl)carbamoyl, N-butyl-N-(4-isobutoxycarbonylbutyl)carbamoyl, N-methyl-N-(2-t-butoxycarbonylmethyl-2-methylethyl)-carbamoyl, N-pentyl-N-(3-pentyloxycarbonylpentyl)-carbamoyl, N-hexyl-N-(6-hexyloxycarbonylhexyl)carbamoyl, N-ethyl-N-[(1-cyclopropylethoxy)carbonylmethyl]carbamoyl, etc];

N-hydroxy(lower)alkylcarbamoyl [e.g. N-hydroxymethylcarbamoyl, N-(2-hydroxyethyl)carbamoyl, N-(1-hydroxyethyl)carbamoyl, N-(3-hydroxypropyl)carbamoyl, N-(1-hydroxybutyl)carbamoyl, N-(2-hydroxymethyl-2-methylethyl)carbamoyl, N-(5-hydroxypentyl)carbamoyl, N-(3-hydroxyhexyl)carbamoyl, etc]; a group of the formula:

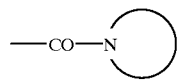

(wherein a group of the formula:

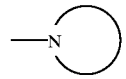

is N-containing heterocyclic group which may have one or more suitable substituent(s), in which N-containing heterocyclic group may contain the other hetero atom(s) such as N, O or S in its ring; or the like; or the like.

Suitable aforesaid "N-containing heterocyclic group" may include saturated or unsaturated, monocyclic or polycyclic heterocyclic group such as unsaturated 3 to 8-membered (more preferably 5 to 7-membered) heteromonocyclic group containing 1 to 4 nitrogen atom(s), for example, azepinyl (e.g. 1H-azepinyl, etc), pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc), tetrazolyl (e.g. 1H-tetrazolyl, 2H-tetrazolyl, etc) etc;

saturated 3 to 8-membered (more preferably 5 to 7-membered) heteromonocyclic group containing 1 to 4 nitrogen atom(s), for example, perhydroazepinyl (e.g. perhydro-1H-azepinyl, etc), pyrrolidinyl, imidazolidinyl, piperidino, piperazinyl, etc;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc;

saturated condensed heterocyclic group containing 1 to 4 nitrogen atom(s), for example, 7-azabicyclo[2.2.1]-heptyl, 3-azabicyclo[3.2.2]nonanyl, etc;

unsaturated 3 to 8-membered (more preferably 5 or 6-membered) heteromonocyclic group containing 1 to 2 oxygen atom(s) and 1 to 3 nitrogen atom(s), for example, dihydrooxazinyl (e.g. 5,6-dihydro-4H-dihydro-1,3-oxazinyl, etc), oxazolyl, isoxazolyl, oxadiazolyl (e.g. 1,2,4-oxadiazolyl, 1,3,4-oxadiazolyl, 1,2,5-oxadiazolyl, etc), etc;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc;

unsaturated condensed heterocyclic group containing 1 to 2 oxygen atom(s) and 1 to 3 nitrogen atom(s), for example, benzoxazolyl, benzoxadiazolyl, etc;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc), dihydrothiazinyl, etc;

saturated 3 to 8-membered (more preferably 5 or 6-membered) heteromonocyclic group containing 1 to 2 sulfur. atom(s) and 1 to 3 nitrogen atom(s), for example, thiazolidinyl, thiomorpholinyl, etc;

unsaturated condensed heterocyclic group containing 1 to 2 sulfur atom(s) and 1 to 3 nitrogen atom(s), for example, benzothiazolyl, benzothiadiazolyl, etc; in which the preferred one may include saturated 3 to 8-membered heteromonocyclic group containing 1 to 4 nitrogen atom(s), saturated 3 to 8-membered heteromonocyclic group containing 1 to 2 oxygen atom(s) and 1 to 3 nitrogen atom(s), and saturated 3 to 8-membered heteromonocyclic group containing 1 to 2 sulfur atom(s) and 1 to 3 nitrogen atom(s).

"N-containing heterocyclic group" thus defined may have one or more referably 1 to 3) suitable substituent(s) such as lower alkyl as mentioned above; hydroxy(lower)alkyl ,e.g. hydroxymethyl, 1-hydroxyethyl, 2-hydroxyethyl, 3-hydroxypropyl, 2-hydroxybutyl, 1-methyl-1-hydroxymethylethyl, 4-hydroxypentyl, 3-hydroxyhexyl, etc); lower alkoxy(lower)alkyl (e.g. methoxymethyl, 2-methoxyethyl, 1-ethoxyethyl, 3-propoxypropyl, 2-(t-butoxy)butyl, 5-pentyloxypentyl, 3-hexyloxyhexyl, etc); acyloxy(lower)alkyl such as lower alkanoyloxy(lower)alkyl (e.g. acetoxymethyl, 1-acetoxyethyl, 2-acetoxyethyl, 2-propionyloxyethyl, 3-propionyloxypropyl, 2-butyryloxybutyl, 4-pivaloyloxypentyl, 6-hexanoyloxyhexyl, etc) or the like; protected carboxy such as lower alkoxycarbonyl as mentioned above; carboxy; ar(lower)alkyl such as phenyl(lower)alkyl (e.g. benzyl, phenethyl, etc), di-phenyl(lower)alkyl (e.g. benzhydryl, etc) or tri-phenyl(lower)alkyl (e.g. trityl, etc); lower alkylamino (e.g. methylamino, ethylamino, propylamino, butylamino, t-butylamino, pentylamino, hexylamino, etc); acyl such as lower alkanoyl as mentioned before; or the like.

Suitable "acyl" moiety in the terms "acyl(lower)alkoxy", "acyl(lower)alkyl", "acyl(lower)alkylidene", "acyloxy", "acyl(lower)alkoxyimino", "acyloxyimino", and "acylhydrazono" can be referred to the ones exemplified before for "acyl".

Suitable "lower alkyl" moiety in the term "acyl(lower)alkyl" may be the ones as exemplified before for "lower alkyl".

Suitable example of acyl(lower)alkyl" may be carboxy (lower)alkyl such as carboxymethyl, 2-carboxyethyl, 3-carboxypropyl, 1-carboxymethylethyl, 4-carboxybutyl, 2-carboxymethyl-2-methylethyl, 5-carboxypentyl, 3-carboxyhexyl, or the like, lower alkanoyl(lower)alkyl such as acetylmethyl, formylmethyl, 2-acetylethyl, 3-propionylpropyl, 4-butyrylbutyl, 3-pentanoylpentyl, 6-hexanoylhexyl, or the like, in which the preferred one may be carboxy($C_1$–$C_4$)alkyl or ($C_1$–$C_4$)alkanoyl($C_1$–$C_4$)alkyl, and the more preferred one may be carboxymethyl, 2-carboxyethyl, 3-carboxypropyl or acetylmethyl.

Another suitable example of "acyl(lower)alkyl" may be protected carboxy(lower)alkyl, in which the preferred one may be esterified carboxy(lower)alkyl, the more preferred one may be lower alkoxycarbonyl(lower)alkyl such as methoxycarbonylmethyl, ethoxycarbonylmethyl, 2-ethoxycarbonylethyl, 1-propoxycarbonylpropyl, 2-isopropoxycarbonylpropyl, butoxycarbonylmethyl, t-butoxycarbonylmethyl, 4-isobutoxycarbonylbutyl, 3-pentyloxycarbonylpentyl, 6-hexyloxycarbonylhexyl, (1-cyclopropylethoxycarbonyl)methyl, or the like, or phenyl (lower)alkoxycarbonyl(lower)alkyl such as benzyloxycarbonylmethyl, 2-benzyloxycarbonylethyl, 1-phenethyloxycarbonylethyl, 3-benzyloxycarbonylpropyl, 2-benzyloxycarbonylbutyl, 2-phenethyloxycarbonylmethyl-2-methylethyl, 3-benzyloxycarbonylpentyl, 6-benzyloxycarbonylhexyl, or the like, the much more preferred one may be ($C_1$–$C_4$)alkoxycarbonyl-($C_1$–$C_4$)alkyl, or phenyl($C_1$–$C_4$)alkoxycarbonyl($C_1$–$C_4$)alkyl, and the most preferred one may be methoxycarbonylmethyl, ethoxycarbonylmethyl, t-butoxycarbonylmethyl, 2-benzyloxycarbonylethyl or 3-benzyloxycarbonylpropyl.

In aforesaid "protected carboxy(lower)alkyl, another preferred one may be amidated carboxy(lower)alkyl, in which the more preferred one may be carbamoyl(lower)-alkyl, N-(lower)alkylcarbamoyl(lower)alkyl, N,N-di-(lower) alkylcarbamoyl(lower)alkyl, N-carboxy(lower)-alkylcarbamoyl (lower)alkyl, N-lower alkoxycarbonyl-(lower)alkylcarbamoyl(lower)alkyl, N-lower alkyl-N-carboxy(lower)alkylcarbamoyl(lower)alkyl, N-lower alkyl-N-lower alkoxycarbonyl(lower)alkylcarbamoyl(lower) alkyl, N-hydroxy(lower)alkylcarbamoyl(lower)alkyl, or a group of the formula:

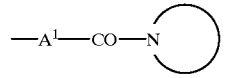

[wherein $A^1$ is lower alkyl, and the group of the formula:

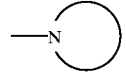

is saturated 3 to 8-membered heteromonocyclic group containing 1 to 4 nitrogen atom(s), saturated 3 to 8-membered heteromonocyclic group containing 1 to 2 oxygen atom(s) and 1 to 3 nitrogen atom(s), or saturated 3 to 8-membered heteromonocyclic group containing 1 to 2 sulfur atom(s) and 1 to 3 nitrogen atom(s), each of which may have 1 to 3 suitable substituent(s) selected from the group consisting of lower alkyl, lower alkanoyl, mono-(or di- or tri-)-phenyl(lower) alkyl and lower alkylamino);

the much more preferred one may be carbamoyl($C_1$–$C_4$) alkyl, N-($C_1$–$C_4$)alkylcarbamoyl($C_1$–$C_4$)alkyl, N,N-di ($C_1$–$C_4$)-alkylcarbamoyl($C_1$–$C_4$)alkyl, N-carboxy ($C_1$–$C_4$)alkyl-carbamoyl($C_1$–$C_4$)alkyl, N-($C_1$–$C_4$) alkoxycarbonyl($C_1$–$C_4$)-alkylcarbamoyl($C_1$–$C_4$)alkyl, N-($C_1$–$C_4$)alkyl-N-carboxy-($C_1$–$C_4$)alkylcarbamoyl ($C_1$–$C_4$)alkyl, N-($C_1$–$C_4$)alkyl-N-($C_1$–$C_4$) alkoxycarbonyl($C_1$–$C_4$)-alkylcarbamoyl($C_1$–$C_4$)alkyl, N-hydroxy($C_1$–$C_4$)-alkylcarbamoyl($C_1$–$C_4$)alkyl, or a group of the formula:

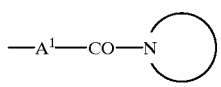

[wherein A¹ is $(C_1-C_4)$alkyl, and the group of the formula:

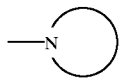

is 1-pyrrolidinyl; piperidino which may have 1 to 3 $(C_1-C_4)$alkylamino;
1-piperazinyl which may have 1 to 3 $(C_1-C_4)$alkyl, $(C_1-C_4)$alkanoyl or tri-phenyl$(C_1-C_4)$alkyl; morpholino; or thiomorpholin-4-yl], and the most preferred one may be carbamoylmethyl, 3-carbamoylpropyl, (N-methylcarbamoyl)methyl, 3-(N-methylcarbamoyl) propyl, (N,N-dimethylcarbamoyl)methyl, 3-(N,N-dimethylcarbamoyl)-propyl, (N-carboxymethylcarbamoyl)methyl, [N-(2-carboxyethyl)carbamoyl]methyl, [N-(3-carboxypropyl)carbamoyl]methyl, 3-(N-carboxymethylcarbamoyl)propyl, (N-t-butoxycarbonylmethylcarbamoyl)methyl, (N-(2-t-butoxycarbonylethyl)carbamoyl]methyl, [N-(3-methoxycarbonylpropyl)carbamoyl]methyl, 3-(N-ethoxycarbonylmethylcarbamoyl)propyl, (N-methyl-N-carboxymethylcarbamoyl)methyl, [(N-methyl-N-(2-carboxyethyl)carbamoyl]methyl, (N-methyl-N-ethoxycarbonylmethylcarbamoyl)methyl, [N-methyl-N-(2-ethoxycarbonylethyl)carbamoyl]methyl, [N-(2-hydroxyethyl)carbamoyl]methyl, pyrrolidin-1-ylcarbonylmethyl, piperidinocarbonylmethyl, (4-methylaminopiperidino)carbonylmethyl, (4-methylpiperazin-1-yl)carbonylmethyl, (4-acetylpiperazin-1-yl)carbonylmethyl, piperazin-1-ylcarbonylmethyl, (4-tritylpiperazin-1-yl) carbonylmethyl, morpholinocarbonylmethyl, or thiomorpholin-4-ylcarbonylmethyl.

Suitable "lower alkylidene" moiety in the terms "acyl (lower)alkylidene" and "heterocyclic(lower)alkylidene which may have one or more suitable substituent(s)" may be the ones as exemplified before for "lower alkylidene".

Suitable example of "acyl(lower)alkylidene" may be carboxy(lower)alkylidene such as carboxymethylene, 2-carboxyethylidene, 2-carboxypropylidene, 4-carboxybutylidene, 5-carboxypentylidene, 3-carboxyhexylidene, or the like, in which the preferred one may be carboxy$(C_1-C_4)$alkylidene, and the more preferred one may be carboxymethylene.

Another suitable example of "acyl(lower)alkylidene" may be protected carboxy(lower)alkylidene, in which the preferred one may be esterified carboxy(lower)alkylidene, the more preferred one may be lower alkoxycarbonyl(lower) alkylidene such as methoxycarbonylmethylene, ethoxycarbonylmethylene, 2-ethoxycarbonylethylidene, 1-propoxycarbonylpropylidene, 2-isopropoxycarbonylpropylidene, butoxycarbonylmethylene, t-butoxycarbonylmethylene, 4-isobutoxycarbonylbutylidene, 3-pentyloxycarbonylpentylidene, 6-hexyloxycarbonylhexylidene, (1-cyclopropylethoxycarbonyl)methylene, or the like, the much more preferred one may be $(C_1-C_4)$alkoxycarbonyl-$(C_1-C_4)$alkylidene, and the most preferred one may be methoxycarbonylmethylene, ethoxycarbonylmethylene, t-butoxycarbonylmethylene.

Suitable "heterocyclic" moiety in the term "heterocyclic (lower)alkylidene which may have one or more suitable substituent(s)" can be referred to the ones as exemplified before for "N-containing heterocyclic group", in which the preferred one may be unsaturated 3 to 8-membered heteromonocyclic group containing 1 to 4 nitrogen atom(s) or unsaturated 3 to 8-membered heteromonocyclic group containing 1 to 2 oxygen atom(s) and 1 to 3 nitrogen atom(s), in which the more preferred one may be dihydrooxazinyl or tetrazolyl.

"Heterocyclic(lower)alkylidene" may have one or more (preferably 1 to 4) suitable substituent(s) (preferably on its heterocyclic moiety) such as lower alkyl, or the like.

Suitable "saturated 3 to 8-membered heteromonocyclic-group containing 1 to 4 nitrogen atom(s)" in the term "saturated 3 to 8-membered heteromonocyclic group containing 1 to 4 nitrogen atom(s) which may have one or more suitable substituent(s)" may include perhydroazepinyl (e.g. perhydro-1H-azepinyl, etc) pyrrolidinyl, imidazolidinyl, piperidyl, piperazinyl, and; the like;
in which the preferred one may be 5 to 7-membered one, and the more preferred one may be pyrrolidinyl, or piperidyl.

Suitable "unsaturated 3 to 8-membered heteromonocyclic group containing 1 to 4 nitrogen atom(s)" in the term "unsaturated 3 to 8-membered heteromonocyclic group containing 1 to 4 nitrogen atom(s) which may have one or more suitable substituent(s)" may include azepinyl (e.g. 1H-azepinyl, etc) pyrrolyl, pyrrolinyl, imidazolyl, pyrazolyl, pyridyl and its N-oxide, dihydropyridyl, pyrimidinyl, dihydropyrimidinyl (e.g. 1,2-dihydropyrimidinyl, etc), tetrahydropyrimidinyl (e.g. 1,2,3,4-tetrahydropyrimidinyl, etc), pyrazinyl, pyridazinyl, triazolyl (e.g. 4H-1,2,4-triazolyl, 1H-1,2,3-triazolyl, 2H-1,2,3-triazolyl, etc), tetrazolyl (e.g. 1H-tetrazolyl, 2H-tetrazolyl) and the like; in which the preferred one may be 5 to 7-membered one, and the more preferred one may be tetrahydropyrimidinyl.

Suitable "saturated 3 to 8-membered heteromonocyclic group containing 1 to 4 oxygen atom(s)" in the term "saturated 3 to 8-membered heteromonocyclic group containing 1 to 4 oxygen atom(s) which may have one or more suitable substituent(s)" may include perhydrofuryl, perhydropyranyl, dioxanyl, and the like; in which the preferred one may be 5 to 7-membered one, and the more preferred one may be perhydrofuryl.

Suitable "saturated condensed heterocyclic group containing 1 to 4 oxygen atom(s)" in the term "saturated condensed heterocyclic group containing 1 to 4 oxygen atom(s) which may have one or more suitable substituent(s)" may include perhydrochromanyl, perhydroisochromanyl, perhydrobenzofuryl (e.g. perhydrobenzo[b]furyl, perhydrobenzo[c]furyl, etc), and the like;
in which the preferred one may be perhydrobenzofuryl.

Aforesaid "saturated 3 to 8-membered heteromonocyclic group containing 1 to 4 nitrogen atom(s)", "unsaturated 3 to 8-membered heteromonocyclic group containing 1 to 4 nitrogen atom(s)", "saturated 3 to 8-membered heteromonocyclic group containing 1 to 4 oxygen atom(s)" and "saturated condensed heterocyclic group containing 1 to 4 oxygen atom(s)" each may have one or more (preferably 1 to 4) suitable substituent(s) selected from the group consisting of oxo; hydroxy; lower alkyl as mentioned before; acyl as mentioned before (in which the preferred one may be protected carboxy, the more preferred one may be lower alkoxycarbonyl, and the most preferred one may be t-butoxycarbonyl); acyl(lower)alkyl as mentioned before (in which the preferred one may be carboxy(lower)alkyl or protected carboxy(lower)alkyl, the more preferred one may be carboxy(lower)alkyl or lower alkoxycarbonyl(lower) alkyl, and the most preferred one may be carboxymethyl, methoxycarbonyimethyl, or ethoxycarbonylmethyl); and the like.

Suitable "lower alkyl", "aryl" and "acyl" in the term "lower alkyl substituted with aryl and acyl" can be referred to the ones as exemplified above for "lower alkyl" moiety in the term "acyl(lower)alkyl", "aryl" and "acyl", respectively.

Suitable example of "lower alkyl substituted with aryl and acyl" may be lower alkyl substituted with phenyl and carboxy such as α-carboxybenzyl, 1-carboxy-2-phenylethyl, 1-carboxymethyl-2-phenylethyl, 4-carboxy-2-phenylbutyl, 1-benzyl-2-carboxy-1-methylethyl, 5-phenyl-3-carboxypentyl, 4-phenyl-3-carboxyhexyl, or the like, in which the preferred one may be $(C_1-C_4)$alkyl substituted with phenyl and carboxy, and the more preferred one may be α-carboxybenzyl.

Suitable "cyclo(lower)alkane having epoxy" may include epoxycyclobutane, epoxycyclopentane, epoxycyclohexane, epoxycycloheptane, epoxycyclooctane, and the like.

Suitable "cyclo(lower)alkene having epoxy" may include 3,4-epoxycyclopentene, 4,5-epoxycyclohexene, 3,4-epoxycycioheptene, 5,6-epoxycyclooctene, and the like.

"Saturated 3 to 8-membered heteromonocyclic compound-containing 1 to 4 nitrogen atom(s) having epoxy" is a heterocyclic compound corresponding to "saturated 3 to 8 membered heteromonocyclic group containing 1 to 4 nitrogen atom(s)" which has epoxy as its substituent and this "saturated 3 to 8-membered heteromonocyclic compound containing 1 to 4 nitrogen atom(s) having epoxy" may have one or more (preferably 1 to 3) suitable substituent(s) as exemplified for those of "saturated 3 to 8-membered heteromonocyclic group containing 1 to 4 nitrogen atom(s)".

"Unsaturated 3 to 8-membered heteromonocyclic compound containing 1 to 4 nitrogen atom(s) having epoxy" is a heterocyclic compound corresponding to "unsaturated 3 to 8-membered heteromonocyclic group containing 1 to 4 nitrogen atom(s)" which has epoxy as its substituent and this "unsaturated 3 to 8-membered heteromonocyclic compound containing 1 to 4 nitrogen atom(s) having epoxy" may have one or more preferably 1 to 3) suitable substituent(s) as exemplified for those of "unsaturated 3 to 8-membered heteromonocyclic group containing 1 to 4 nitrogen atom(s)".

"Saturated 3 to 8-membered heteromonocyclic compound containing 1 to 4 oxygen atom(s) having epoxy" is a heterocyclic compound corresponding to "saturated 3 to 8-membered heteromonocyclic group containing 1 to 4 oxygen atom(s)" which has epoxy as its substituent and this "saturated 3 to 8-membered heteromonocyclic compound containing 1 to 4 oxygen atom(s) having epoxy" may have one or more (preferably 1 to 3) suitable substituent(s) as exemplified for those of "saturated 3 to 8-membered heteromonocyclic group containing 1 to 4 oxygen atom(s)".

"Saturated condensed heterocyclic compound containing 1 to 4 oxygen atom(s) having epoxy" is a heterocyclic compound corresponding to "saturated condensed heterocyclic group containing 1 to 4 oxygen atom(s)" which has epoxy as its substituent and this "saturated condensed heterocyclic compound containing 1 to 4 oxygen atom(s) having epoxy" may have one or more (preferably 1 to 3) suitable substituent(s) as exemplified for those of "saturated condensed heterocyclic group containing 1 to 4 oxygen atom(s)".

"Cyclo(lower)alkyl having oxo" is cyclo(lower)alkyl as explained before which has oxo as its substituent and this "cyclo(lower)alkyl having oxo" may have one or more (preferably 1 to 2) suitable substituent(s) as exemplified for those of "cyclo(lower)alkyl".

"Cyclo(lower)alkenyl having oxo" is cyclo(lower)alkenyl as explained before which has oxo as its substituent and this "cyclo(lower)alkenyl having oxo" may have one or more (preferably 1 to 2) suitable substituent(s) as exemplified for those of "cyclo(lower)alkenyl".

"Saturated 3 to 8-membered heteromonocyclic group containing 1 to 4 nitrogen atom(s) having oxo" is saturated 3 to 8-membered heteromonocyclic group containing 1 to 4 nitrogen atom(s) which has oxo as its substituent and this "saturated 3 to 8-membered heteromonocyclic group containing 1 to 4 nitrogen atom(s) having oxo" may have one or more (preferably 1 to 3) suitable substituent(s) as exemplified for those of "saturated 3 to 8-membered heteromonocyclic group containing 1 to 4 nitrogen atom(s)".

"Unsaturated 3 to 8-membered heteromonocyclic group. containing 1 to 4 nitrogen atom(s) having oxo" is unsaturated 3 to 8-membered heteromonocyclic group containing 1 to 4 nitrogen atom(s) which has oxo as its substituent and this "unsaturated 3 to 8-membered heteromonocyclic group containing 1 to 4 nitrogen atom(s) having oxo" may have one or more (preferably 1 to 3) suitable substituent(s) as exemplified for those of "unsaturated 3 to 8-membered heteromonocyclic group containing 1 to 4 nitrogen atom(s)".

"Saturated 3 to 8-membered heteromonocyclic group containing 1 to 4 oxygen atom(s) having oxo" is saturated 3 to 8-membered heteromonocyclic group containing 1 to 4 oxygen atom(s) which has oxo as its substituent and this "saturated 3 to 8-membered heteromonocyclic group containing 1 to 4 oxygen atom(s) having oxo" may have one or more (preferably 1 to 3) suitable substituent(s) as exemplified for those of "saturated 3 to 8-membered heteromonocyclic group containing 1 to 4 oxygen atom(s)".

"Saturated condensed heterocyclic group containing 1 to 4 oxygen atom(s) having oxo" is saturated condensed heterocyclic group containing 1 to 4 oxygen atom(s) which has oxo as its substituent and this "saturated condensed heterocyclic group containing 1 to 4 oxygen atom(s) having oxo" may have one or more (preferably 1 to 3) suitable substituent (s) as exemplified for those of "saturated condensed heterocyclic group containing 1 to 4 oxygen atom(s)".

"Cyclo(lower)alkyl having hydroxy" is cyclo(lower)alkyl as explained before which has hydroxy as its substituent and this "cyclo(lower)alkyl having hydroxy" may have one or more (preferably 1 to 2) suitable substituent(s) as exemplified for those of "cyclo(lower)alkyl".

"Cyclo(lower)alkenyl having hydroxy" is cyclo(lower) alkenyl as explained before which has hydroxy as its substituent and this "cyclo(lower)alkenyl having hydroxy" may have one or more (preferably 1 to 2) suitable substituent(s) as exemplified for those of "cyclo(lower)alkenyl".

"Saturated 3 to 8-membered heteromonocyclic group containing 1 to 4 nitrogen atom(s) having hydroxy" is saturated 3 to 8-membered heteromonocyclic group containing 1 to 4 nitrogen atom(s) which has hydroxy as its substituent and this "saturated 3 to 8-membered heteromonocyclic group containing 1 to 4 nitrogen atom(s) having hydroxy" may have one or more (preferably 1 to 3) suitable substituent(s) as exemplified for those of "saturated 3 to 8-membered heteromonocyclic group containing 1 to 4 nitrogen atom(s)".

"Unsaturated 3 to 8-membered heteromonocyclic group containing 1 to 4 nitrogen atom(s) having hydroxy" is unsaturated 3 to 8-membered heteromonocyclic group containing 1 to 4 nitrogen atom(s) which has hydroxy as its substituent and this "unsaturated 3 to 8-membered heteromonocyclic group containing 1 to 4 nitrogen atom(s) having hydroxy" may have one or more (preferably 1 to 3) suitable substituent(s) as exemplified for those of "unsaturated 3 to 8-membered heteromonocyclic group containing 1 to 4 nitrogen atom(s)".

"Saturated 3 to 8-membered heteromonocyclic group containing 1 to 4 oxygen atom(s) having hydroxy" is saturated 3 to 8-membered heteromonocyclic group containing 1 to 4 oxygen atom(s) which has hydroxy as its substituent and this "saturated 3 to 8-membered heteromonocyclic group containing 1 to 4 oxygen atom(s) having hydroxy" may have one or more (preferably 1 to 3) suitable substituent(s) as exemplified for those of "saturated 3 to 8-membered heteromonocyclic group containing 1 to 4 oxygen atom(s)".

"Saturated condensed heterocyclic group containing 1 to 4 oxygen atom(s) having hydroxy" is saturated condensed heterocyclic group containing 1 to 4 oxygen atom(s) which has hydroxy as its substituent and this "saturated condensed heterocyclic group containing 1 to 4oxygen atom(s) having hydroxy" may have one or more (preferably 1 to 3) suitable substituent(s) as exemplified for those of "saturated condensed heterocyclic group containing 1 to 4 oxygen atom(s)".

"Cyclo(lower)alkyl having lower alkylidene" is cyclo(lower)alkyl as explained before which has lower alkylidene as its substituent and this "cyclo(lower)alkyl having lower alkylidene" may have one or more (preferably 1 to 2) suitable substituent(s) as exemplified for those of "cyclo(lower)alkyl".

"Cyclo(lower)alkyl having acyl(lower)alkylidene" is cyclo(lower)alkyl as explained before which has acyl(lower)alkylidene as its substituent and this "cyclo(lower)alkyl having acyl(lower)alkylidene" may have one or more (preferably 1 to 2) suitable substituent(s) as exemplified far those of "cyclo(lower)alkyl".

"Cyclo(lower)alkyl having cyano(lower)alkylidene" is cyclo(lower)alkyl as explained before which has cyano(lower)alkylidene as its substituent and this "cyclo(lower)alkyl having cyano(lower)alkylidene" may have one or more (preferably 1 to 2) suitable substituent(s) as exemplified for those of "cyclo(lower)alkyl".

"Cyclo(lower)alkyl having heterocyclic(lower)alkylidene" is cyclo(lower)alkyl as explained before which has heterocyclic(lower)alkylidene as its substituent and this "cyclo(lower)alkyl having heterocyclic(lower)alkylidene" may have one or more (preferably 1 to 2) suitable substituent(s) as exemplified for hose of "cyclo(lower)alkyl".

"Cyclo(lower)alkenyl having lower alkylidene" is cyclo(lower)alkenyl as explained before which has lower alkylidene as its substituent and this "cyclo(lower)alkenyl having lower alkylidene" may have one or more (preferably 1 to 2) suitable substituent(s) as exemplified for those of "cyclo(lower)alkenyl".

"Cyclo(lower)alkenyl having acyl(lower)alkyl" is cyclo(lower)alkenyl as explained before which has acyl(lower)alkyl as its substituent and this "cyclo(lower)alkenyl having acyl(lower)alkyl" may have one or more (preferably 1 to 2) suitable substituent(s) as exemplified for those of "cyclo(lower)alkenyl".

"Cyclo(lower)alkenyl having acyl(lower)alkylidene" is cyclo(lower)alkenyl as explained before which has acyl(lower)alkylidene as its substituent and this "cyclo(lower)alkenyl having acyl(lower)alkylidene" may have one or more (preferably 1 to 2) suitable substituent(s) as exemplified for those of "cyclo(lower)alkenyl".

"Cyclo(lower)alkenyl having cyano(lower)alkylidene" is cyclo(lower)alkenyl as explained before which has cyano(lower)alkylidene as its substituent and this "cyclo(lower)alkenyl having cyano(lower)alkylidene" may have one or more (preferably 1 to 2) suitable substituent(s) as exemplified for those of "cyclo (lower) alkenyl".

"Cyclo(lower)alkenyl having heterocyclic(lower)alkylidene" is cyclo(lower)alkenyl as explained before which has heterocyclic(lower)alkylidene as its substituent and this "cyclo(lower)alkenyl having heterocyclic(lower)alkylidene" may have one or more (preferably 1 to 2) suitable substituent(s) as exemplified for those of "cyclo(lower)alkenyl".

"Cyclo(lower)alkyl having protected carboxy" is cyclo(lower)alkyl as explained before which has protected carboxy as its substituent and this "cyclo(lower)alkyl having protected carboxy" may have one or more (preferably 1 to 2) suitable substituent(s) as exemplified for those of "cyclo(lower)alkyl".

"Cyclo(lower)alkyl having protected carboxy(lower)alkyl" is cyclo(lower)alkyl as explained before which has protected carboxy(lower)alkyl as its substituent and this "cyclo(lower)alkyl having protected carboxy(lower)alkyl" may have one or more (preferably 1 to 2) suitable substituent(s) as exemplified for those of "cyclo(lower)alkyl".

"Cyclo(lower)alkyl having protected carboxy(lower)alkylidene" is cyclo(lower)alkyl as explained before which has protected carboxy(lower)alkylidene as its substituent and this "cyclo(lower)alkyl having protected carboxy(lower)alkylidene" may have one or more (preferably 1 to 2) suitable substituent(s) as exemplified for those of "cyclo(lower)alkyl".

"Cyclo(lower)alkyl having N-protected carboxy(lower)alkylcarbamoyl(lower)alkyl" is cyclo(lower)alkyl as explained before which has N-protected carboxy(lower)alkylcarbamoyl(lower)alkyl as its substituent and this "cyclo(lower)alkyl having N-protected carboxy(lower)alkylcarbamoyl(lower)alkyl" may have one or more (preferably 1 to 2) suitable substituent(s) as exemplified for those of "cyclo (lower) alkyl".

"Cyclo(lower)alkyl having N-lower alkyl-N-protected.carboxy(lower)alkylcarbamoyl(lower)alkyl" is cyclo(lower)alkyl as explained before which has N-lower alkyl-N-protected carboxy(lower)alkylcarbamoyl-(lower)alkyl as its substituent and this "cyclo(lower)alkyl having N-lower alkyl-N-protected carboxy(lower)alkylcarbamoyl(lower)alkyl" may have one or more (preferably 1 to 2) suitable substituent(s) as exemplified for those of "cyclo(lower)alkyl".

"Cyclo(lower)alkyl having protected carboxy(lower)alkoxyimino" is cyclo(lower)alkyl as explained before which has protected carboxy(lower)alkoxyimino as its substituent and this "cyclo(lower)alkyl having protected carboxy(lower)alkoxyimino" may have one or more (preferably 1 to 2) suitable substituent(s) as exemplified for those of "cyclo(lower)alkyl".

"Cyclo(lower)alkenyl having protected carboxy" is cyclo(lower)alkenyl as explained before which has protected carboxy as its substituent and this "cyclo(lower)alkenyl having protected carboxy" may have one or more (preferably 1 to 2) suitable substituent(s) as exemplified or those of "cyclo(lower)alkenyl".

"Cyclo(lower)alkenyl having protected carboxy(lower)alkyl" is cyclo(lower)alkenyl as explained before which has protected carboxy(lower)alkyl as its substituent and this "cyclo(lower)alkenyl having protected carboxy(lower)alkyl" may have one or more (preferably 1 to 2) suitable substituent(s) as exemplified for those of "cyclo(lower)alkenyl".

"Cyclo(lower)alkenyl having protected carboxy(lower)alkylidene" is cyclo(lower)alkenyl as explained before which has protected carboxy(lower)alkylidene as its substituent and this "cyclo(lower)alkenyl having protected carboxy(lower)alkylidene" may have one or more (preferably 1 to 2) suitable substituent(s) as exemplified for those of "cyclo(lower)alkenyl".

"Cyclo(lower)alkenyl having N-protected carboxy(lower)alkylcarbamoyl(lower)alkyl" is cyclo(lower)alkenyl as explained before which has N-protected carboxy(lower)alkylcarbamoyl(lower)alkyl as its substituent and this "cyclo(lower)alkenyl having N-protected carboxy(lower)alkylcarbamoyl(lower)alkyl" may have one or more (preferably 1 to 2) suitable substituent(s) as exemplified for those of "cyclo(lower)alkenyl".

"Cyclo(lower)alkenyl having N-lower alkyl-N-protected carboxy(lower)alkylcarbamoyl (lower) alkyl" is cyclo(lower)alkenyl as explained before which has N-lower alkyl-N-protected carboxy(lower)alkylcarbamoyl(lower) alkyl as its substituent and this "cyclo(lower)alkenyl having N-lower alkyl-N-protected carboxy(lower) alkylcarbamoyl(lower)alkyl" may have one or more (preferably 1 to 2) suitable substituent(s) as exemplified for those of "cyclo(lower)alkenyl".

"Cyclo(lower)alkenyl having protected carboxy(lower)alkoxyimino" is cyclo(lower)alkenyl as explained before which has protected carboxy(lower)alkoxyimino as its substituent and this "cyclo(lower)alkenyl having protected carboxy(lower)alkoxyimino" may have one or more (preferably 1 to 2) suitable substituent(s) as exemplified for those of "cyclo(lower)alkenyl".

"Saturated 3 to 8-membered heteromonocyclic group containing 1 to 4 nitrogen atom(s) having protected carboxy(lower)alkyl" is saturated 3 to 8-membered heteromonocyclic group containing 1 to 4 nitrogen atom(s) which has protected carboxy(lower)alkyl as its substituent and this "saturated 3 to 8-membered heteromonocyclic group containing 1 to 4 nitrogen atom(s) having protected carboxy(lower)alkyl" may have one or more (preferably 1 to 3) suitable substituent(s) as exemplified for those of "saturated 3 to 8-membered heteromonocyclic group containing 1 to 4 nitrogen atom(s)".

"Unsaturated 3 to 8-membered heteromonocyclic group containing 1 to 4 nitrogen atom(s) having protected carboxy(lower)alkyl" is unsaturated 3 to 8-membered heteromonocyclic group containing 1 to 4 nitrogen atom(s) which has protected carboxy(lower)alkyl as its substituent and this "unsaturated 3 to 8-membered heteromonocyclic group containing 1 to 4 nitrogen atom(s) having protected carboxy(lower)alkyl" may have one or more (preferably 1 to 3) suitable substituent(s) as exemplified for those of "unsaturated 3 to 8-membered heteromonocyclic group containing 1 to 4 nitrogen atom(s)".

"Saturated 3 to 8-membered heteromonocyclic group containing 1 to 4 oxygen atom(s) having protected carboxy(lower)alkyl" is saturated 3 to 8-membered heteromonocyclic group containing 1 to 4 oxygen atom(s) which has protected carboxy(lower)alkyl as its substituent and this "saturated 3 to 8-membered heteromonocyclic group containing 1 to 4 oxygen atom(s) having protected carboxy(lower)alkyl" may have one or more (preferably 1 to 3) suitable substituent(s) as exemplified for those of "saturated 3 to 8-membered heteromonocyclic group containing 1 to 4 oxygen atom(s)".

"Saturated condensed heterocyclic group containing 1 to 4 oxygen atom(s) having protected carboxy(lower)alkyl" is saturated condensed heterocyclic group containing 1 to 4 oxygen atom(s) which has protected carboxy(lower)alkyl as its substituent and this "saturated condensed heterocyclic group containing 1 to 4 oxygen atom(s) having protected carboxy(lower)alkyl" may have one or more (preferably 1 to 3) suitable substituent(s) as exemplified for those of "saturated condensed heterocyclic group containing 1 to 4 oxygen atom(s)".

"Cyclo(lower)alkyl having carboxy" is cyclo(lower)alkyl as explained before which has carboxy as its substituent and this "cyclo(lower)alkyl having carboxy" may have one or more (preferably 1 to 2) suitable substituent(s) as exemplified for those of "cyclo(lower)alkyl".

"Cyclo(lower)alkyl having carboxy(lower)alkyl" is cyclo(lower)alkyl as explained before which has carboxy(lower)alkyl as its substituent and this "cyclo(lower)alkyl having carboxy(lower)alkyl" may have one or more (preferably 1 to 2) suitable substituent(s) as exemplified for those of "cyclo(lower)alkyl".

"Cyclo(lower)alkyl having carboxy(lower)alkylidene" is cyclo(lower)alkyl as explained before which has carboxy(lower)alkylidene as its substituent and this "cyclo(lower)alkyl having carboxy(lower)alkylidene" may have one or more (preferably 1 to 2) suitable substituent(s) as exemplified for those of "cyclo(lower)alkyl".

"Cyclo(lower)alkyl having N-carboxy(lower)alkylcarbamoyl(lower)alkyl" is cyclo(lower)alkyl as explained before which has N-carboxy(lower)alkylcarbamoyl(lower)alkyl as its substituent and this "cyclo(lower)alkyl having N-carboxy(lower)alkylcarbamoyl(lower)alkyl" may have one or more (preferably 1 to 2) suitable substituent(s) as exemplified for those of "cyclo(lower)alkyl".

"Cyclo(lower)alkyl having N-lower alkyl-N-carboxy(lower)alkylcarbamoyl(lower)alkyl" is cyclo(lower)alkyl as explained before which has N-lower alkyl-N-carboxy(lower)alkylcarbamoyl(lower)alkyl as its substituent and this "cyclo(lower)alkyl having N-lower alkyl-N-carboxy(lower)alkylcarbamoyl(lower)alkyl" may have one or more (preferably 1 to 2) suitable substituent(s) as exemplified for those of "cyclo(lower)alkyl".

"Cyclo(lower)alkyl having carboxy(lower)alkoxyimino" is cyclo(lower)alkyl as explained before which has carboxy(lower)alkoxyimino as its substituent and this "cyclo(lower)alkyl having carboxy(lower)alkoxyimino" may have one or more (preferably 1 to 2) suitable substituent(s) as exemplified for those of "cyclo(lower)alkyl".

"Cyclo(lower)alkenyl having carboxy" is cyclo(lower)alkenyl as explained before which has carboxy as its substituent and this "cyclo(lower)alkenyl having carboxy" may have one or more (preferably 1 to 2) suitable substituent(s) as exemplified for those of "cyclo(lower)alkenyl".

"Cyclo(lower)alkenyl having carboxy(lower)alkyl" is cyclo(lower)alkenyl as explained before which has carboxy(lower)alkyl as its substituent and this "cyclo(lower)alkenyl having carboxy(lower)alkyl" may have. one or more (preferably 1 to 2) suitable substituent(s) as exemplified for those of "cyclo(lower)alkenyl".

"Cyclo(lower)alkenyl having carboxy(lower)alkylidene" is cyclo(lower)alkenyl as explained before which has carboxy(lower)alkylidene as its substituent and this "cyclo(lower)alkenyl having carboxy(lower)alkylidene" may have one or more (preferably 1 to 2) suitable substituent(s) as exemplified for those of "cyclo(lower)alkenyl".

"Cyclo(lower)alkenyl having N-carboxy(lower)alkylcarbamoyl(lower)alkyl" is cyclo(lower)alkenyl as explained before which has N-carboxy(lower)alkylcarbamoyl(lower)alkyl as its substituent and this "cyclo (lower)alkenyl having N-carboxy(lower)alkylcarbamoyl (lower)alkyl" may have one or more (preferably 1 to 2) suitable substituent(s) as exemplified for those of "cyclo (lower)alkenyl".

"Cyclo(lower) alkenyl having N-lower alkyl-N-carboxy (lower)alkylcarbamoyl(lower)alkyl" is cyclo(lower)alkenyl as explained before which has N-lower alkyl-N-carboxy (lower)alkylcarbamoyl(lower)alkyl as its substituent and this "cyclo(lower)alkenyl having N-lower alkyl-N-carboxy (lower)alkylcarbamoyl(lower)alkyl" may have one or more (preferably 1 to 2) suitable substituent(s) as exemplified for those of "cyclo(lower)alkenyl".

"Cyclo(lower)alkenyl having carboxy(lower) alkoxyimino" is cyclo(lower)alkenyl as explained before which has carboxy(lower)alkoxyimino as its substituent and this "cyclo(lower)alkenyl having carboxy(lower) alkoxyimino" may have one or more (preferably 1 to 2) suitable substituent(s) as exemplified for those of "cyclo (lower)alkenyl".

"Saturated 3 to 8-membered heteromonocyclic group containing 1 to 4 nitrogen atom(s) having carboxy(lower) alkyl" is saturated 3 to 8-membered heteromonocyclic group containing 1 to 4 nitrogen atom(s) which has carboxy(lower) alkyl as its substituent and this "saturated 3 to 8-membered heteromonocyclic group containing 1 to 4 nitrogen atom(s) having carboxy(lower)alkyl" may have one or more (preferably 1 to 3) suitable substituent(s) as exemplified for those of "saturated 3 to 8-membered heteromonocyclic group containing 1 to 4 nitrogen atom(s)".

"Unsaturated 3 to 8-membered heteromonocyclic group containing 1 to 4 nitrogen atom(s) having carboxy(lower) alkyl" is unsaturated 3 to 8-membered heteromonocyclic group containing 1 to 4 nitrogen atom(s) which has carboxy (lower)alkyl as its substituent and this "unsaturated 3 to 8-membered heteromonocyclic group containing 1 to 4 nitrogen atom(s) having carboxy(lower)alkyl" may have one or more (preferably 1 to 3) suitable substituent(s) as exemplified for those of "unsaturated 3 to 8-membered heteromonocyclic group containing 1 to 4 nitrogen atom(s)".

"Saturated 3 to 8-membered heteromonocyclic group containing 1 to 4 oxygen atom(s) having carboxy(lower) alkyl" is saturated 3 to 8-membered heteromonocyclic group containing 1 to 4 oxygen atom(s) which has carboxy(lower) alkyl as its substituent and this "saturated 3 to 8-membered heteromonocyclic group containing 1 to 4 oxygen atom(s) having carboxy(lower)alkyl" may have one or more (preferably 1 to 3) suitable substituent(s) as exemplified for those of "saturated 3 to 8-membered heteromonocyclic group containing 1 to 4 oxygen atom(s)".

"Saturated condensed heterocyclic group containing 1 to 4 oxygen atom(s) having carboxy(lower)alkyl" is saturated condensed heterocyclic group containing 1 to 4 oxygen atom(s) which has carboxy(lower)alkyl as its substituent and this "saturated condensed heterocyclic group containing 1 to 4 oxygen atom(s) having carboxy(lower)alkyl" may have one or more (preferably 1 to 3) suitable substituent(s) as exemplified for those of "saturated condensed heterocyclic group containing 1 to 4 oxygen atom(s)".

"Cyclo(lower)alkyl having carboxy(lower)alkyl" is cyclo (lower)alkyl as explained before which has carboxy(lower) alkyl as its substituent and this "cyclo(lower)alkyl having carboxy(lower)alkyl" may have one or more (preferably 1 to 2) suitable substituent(s) as exemplified for hose of "cyclo (lower)alkyl".

"Cyclo(lower)alkyl having carboxy(lower)alkylidene" is cyclo(lower)alkyl as explained before which has carboxy (lower)alkylidene as its substituent and this "cyclo(lower) alkyl having carboxy(lower)alkylidene" may have one or more (preferably 1 to 2) suitable substituent(s) as exemplified for those of "cyclo(lower)alkyl".

"Cyclo(lower)alkenyl having carboxy(lower)alkyl" is cyclo(lower)alkenyl as explained before which has carboxy (lower)alkyl as its substituent and this "cyclo(lower)alkenyl having carboxy(lower)alkyl" may have one or more (preferably 1 to 2) suitable substituent(s) as exemplified for those of "cyclo(lower)alkenyl".

"Cyclo(lower)alkenyl having carboxy(lower)alkylidene" is cyclo(lower)alkenyl as explained before which has carboxy(lower)alkylidene as its substituent and this "cyclo (lower)alkenyl having carboxy(lower)alkylidene" may have one or more (preferably 1 to 2) suitable substituent(s) as exemplified for those of "cyclo(lower)alkenyl".

"Cyclo(lower)alkyl having amidated carboxy(lower) alkyl" is cyclo(lower)alkyl as explained before which has amidated carboxy(lower)alkyl as its substituent and this "cyclo(lower)alkyl having amidated carboxy(lower)alkyl" may have one or more (preferably 1 to 2) suitable substituent (s) as exemplified for those of "cyclo(lower)alkyl".

"Cyclo(lower)alkyl having amidated carboxy(lower) alkylidene" is cyclo(lower)alkyl as explained before which has amidated carboxy(lower)alkylidene as its substituent and this "cyclo(lower)alkyl having amidated carboxy(lower) alkylidene" may have one or more (preferably 1 to 2) suitable substituent(s) as exemplified for those of "cyclo (lower)alkyl".

"Cyclo(lower)alkenyl having amidated carboxy(lower) alkyl" is cyclo(lower)alkenyl as explained before which has amidated carboxy(lower)alkyl as its substituent and this "cyclo(lower)alkenyl having amidated carboxy(lower) alkyl" may have one or more (preferably 1 to 2) suitable substituent(s) as exemplified for those of "cyclo(lower) alkenyl".

"Cyclo(lower)alkenyl having amidated carboxy(lower) alkylidene" is cyclo(lower)alkenyl as explained before which has amidated carboxy(lower)alkylidene as its substituent and this "cyclo(lower)alkenyl having amidated carboxy(lower)alkylidene" may have one or more (preferably 1 to 2) suitable substituent(s) as exemplified for those of "cyclo(lower)alkenyl".

Suitable "an acid residue" may include halogen (e.g. fluoro, chloro, bromo, iodo), acyloxy such as lower alkanoyloxy (e.g. acetoxy, propionyloxy, etc), sulfonyloxy (e.g. methylsulfonyloxy, p-tolylsulfonyloxy, etc), and the like.

The processes for the preparation of the object compound (I) or a salt thereof (Processes 1 to 8) are explained in detail in the following.

Process 1

The compound (I) or a salt thereof can be prepared by reacting the compound (II) or a salt thereof with the compound (III) or a salt thereof.

Suitable salt of the compound (II) can be referred to an acid addition salt as exemplified for the compound.

Suitable salt of the compound (III) can be referred to the ones as exemplified for the compound (I).

The present reaction may be carried out in a solvent such as water, phosphate buffer, acetone, chloroform, acetonitrile, nitrobenzene, toluene, methylene chloride, ethylene chloride, formamide, N,N-dimethylformamide, methanol, ethanol, sec-butanol, amyl alcohol, diethyl ether, dimethoxyethane, dioxane, tetrahydrofuran, dimethyl sulfoxide, or any other organic solvent which does not adversely affect the reaction, preferably in ones having strong polarities. Among the solvents, hydrophilic solvents may be used in a mixture with water. When the compound (III) is in liquid, it can also be used as a solvent.

The reaction is preferably conducted in the presence, of a base, for example, inorganic base such as alkali metal hydroxide, alkali metal alkoxide, alkali metal carbonate, alkali metal bicarbonate, alkali metal hydride, organic base such as benzyltrimethylammonium hydroxide trialkylamine, and the like.

The reaction temperature is not critical, and the reaction is usually carried out at ambient temperature, under warming or under heating.

The present reaction is preferably carried out in the presence of alkali metal halide [e.g. sodium iodide, potassium iodide, etc], alkali metal thiocyanate [e.g. sodium thiocyanate, potassium thiocyanate, etc] or the like.

Process 2

The compound (Ib) or a salt thereof can be prepared by subjecting the compound (Ia) or a salt thereof to reduction reaction.

Suitable salts of the compounds (Ia) and (Ib) can be referred to the ones as exemplified for the compound (I).

The reduction reaction of this process can be carried out according to a conventional reduction methods in this field or the art (e.g. chemical reduction, catalytic reduction, etc).

Process 3

The compound (Ib) or a salt thereof can be prepared by reacting the compound (II) or a salt thereof with the compound (IV).

The reaction of this process can be carried out according to a similar manner to that in Process 1.

Process 4

The compound (Ia) or a salt thereof can be prepared by subjecting the compound (Ib) or a salt thereof to oxidation reaction.

The oxidation reaction of this process can be carried out according to a conventional oxidation methods in this field of the art.

Process 5

The compound (Id) or a salt thereof can be prepared by subjecting the compound (Ic) or a salt thereof to so-called Wittig type reaction.

Suitable salt of the compounds (Ic) and (Id) can be referred to the ones as exemplified for the compound (I).

The reaction of this process can be carried out by reacting the compound (Ic) or a salt thereof with a so-called Wittig reagent as shown in the following formulae:

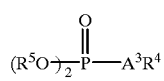 (VII)

[wherein $R^3$ is aryl or lower alkyl, each as mentioned above, $R^5$ is lower alkyl as mentioned above, $R^4$ is hydrogen; acyl as mentioned above; cyano; or heterocyclic group which may have one or more suitable substituent(s) [in which suitable "heterocyclic group" can be referred to the ones as exemplified before for "N-containing heterocyclic group", and this "heterocyclic group" may have one or more (preferably 1 to 4) suitable substituent(s) such as lower alkyl as mentioned above];

$A^2$ is lower alkylidene, and $A^3$ is lower alkyl as mentioned above].

The aforesaid Wittig reagents (VI) and (VII) can be prepared according to a usual manner.

The reaction of this process can be carried out in the presence of base such as alkali metal hydride (e.g. sodium hydride, potassium hydride, etc), alkali metal lower alkoxide (e.g. potassium t-butoxide, etc) or the like in case c; using Wittig reagent (VII).

The reaction is usually carried out in a conventional solvent such as diethyl ether, tetrahydrofuran, methylene chloride, benzene, toluene, N,N-dimethylformamide or any other solvent which does not adversely influence the reaction.

The reaction temperature is not critical and the reaction can be carried out under cooling, at room temperature, under warming or under heating.

The reaction condition can be determined according to the kind of the compound (Ic) and the Wittig reagent to be used.

Process 6

The compound (If) or a salt thereof can be prepared by subjecting the compound (Ie) or a salt thereof to elimination reaction of carboxy protective group.

Suitable salts of the compounds (Ie) and (If) can be referred to the ones as exemplified for the compound (I).

This reaction is carried out in accordance with a conventional method such as hydrolysis, or the like.

The hydrolysis is preferably carried out in the presence of a base or an acid including Lewis acid. Suitable base may include an inorganic base and an organic base such as an alkali metal [e.g. sodium, potassium, etc], an alkaline earth metal [e.g. magnesium, calcium, etc], the hydroxide or carbonate or bicarbonate. thereof, trialkylamine [e.g. trimethylamine, triethylamine, etc], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc] and an inorganic acid [e.g. hydrochloric acid, hydrobromic acid, sulfuric acid, hydrogen chloride, hydrogen bromide, etc]. The elimination using Lewis acid such as trihaloacetic acid [e.g. trichloroacetic acid, trifluoroacetic acid, etc] or the like is preferably carried out in the presence of cation trapping agents [e.g. anisole, phenol, etc].

The reaction s usually carried out in a solvent such as water, an alcohol [e.g. methanol, ethanol, etc], methylene chloride, tetrahydrofuran, dioxane, a mixture thereof or any other solvent which does not adversely influence the reaction. A liquid base or acid can be also used as the solvent.

The reaction temperature is not critical and the reaction is usually carried out under cooling to heating.

Process 7

The compound (I) or a salt thereof can be prepared by subjecting the compound (V) or a salt thereof to cyclization reaction.

Suitable salt of the compound (V) can be referred to acid addition salts as exemplified for the compound (I).

The cyclization reaction of this process can be carried out, for example, by reacting the compound (V) or a salt thereof with glyoxalic acid or its reactive derivative or a salt thereof and the compound of the formula:

 (VIII)

(wherein $R^2$ is as defined above) or a salt thereof.

Suitable salt of glyoxalic acid can be referred to a salt with a base as exemplified for the compound (I).

Suitable salt of the compound (VIII) can be referred to an acid addition salt as exemplified for the compound (I).

Suitable reactive derivative of glyoxalic acid may be the ones conventionally used in this field of the art such as an activated ester thereof.

The reaction can be carried out in the presence or absence of a solvent.

The reaction temperature is not critical and the reaction is usually carried out under warming to heating.

Process 8

The compound (Ih) or a salt thereof can be prepared by subjecting the compound (Ig) or its reactive derivative at the carboxy group or a salt thereof to amidation reaction.

Suitable salts of the compounds (Ig) and (Ih) can be referred to the ones as exemplified for the compound (I).

This reaction can be carried out by reacting the compound (Ig) or its reactive derivative at the carboxy group or a salt thereof with an amidation reagent.

This amidation reagent is the "amine compound" or its reactive derivative at the amino group or a salt thereof corresponding to the object amide, and the suitable examples thereof may include ammonia; lower alkylamine; higher alkylamine; N,N-di(lower)alkylamine; N-lower alkyl-N-ar(lower)alkylamine; N-carboxy(lower)alkylamine; N-protected carboxy(lower)alkylamine; N-lower alkyl-N-carboxy(lower)alkylamine; N-lower alkyl-N-protected carboxy(lower)alkylamine; N-hydroxy(lower)alkylamine; a compound of the formula:

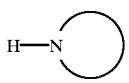

(wherein a group of the formula:

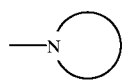

is as defined above); and the like.

Suitable salt of "amine compound" can be referred to the ones as exemplified for the compound (I).

Suitable reactive derivative at the carboxy group of the compound (Ig) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous. acid, sulfurous acid, thiosulfuric acid, sulfuric acid, sulfonic acid [e.g. methanesulfonic acid, etc], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc] or aromatic carboxylic acid [e.g. benzoic acid, etc]; a symmetrical acid anhydride; an activated amide with imidazole, 4-substituted imidazole, dimethylpyrazole, triazole, tetrazole or 1-hydroxy-1H-benzotriazole; or an activated ester [e.g., cyanomethyl ester, methoxymethyl ester, dimethyliminomethyl [(CH$_3$)$_2$N=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc] or an ester. with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc], and the like. These reactive derivatives can optionally be selected from them according to the kind of the compound (Ig) to be used.

Suitable reactive derivative at the amino group of "amine compound" may include Schiff's base type imino or its tautomeric enamine type isomer formed by the reaction of "amine compound" with a carbonyl compound such as aldehyde, ketone or the like; a silyl derivative formed by the reaction of "amine compound" with a silyl compound such as bis(trimethylsilyl)acetamide, mono(trimethylsilyl)acetamide, bis(trimethylsilyl)urea or the like; a derivative formed by reaction of "amine compound" with phosphorus trichloride or phosgene, and the like.

The reaction is usually carried out in a conventional solvent such as water, alcohol [e.g. methanol, ethanol, etc], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (Ig) is used in a free acid form or its salt form, the reaction is preferably carried out in the presence of a conventional condensing agent such as N,N'-dicyclohexylcarbodiimide; or the like.

The reaction may also be carried out in the presence of an inorganic or organic base such as an alkali metal carbonate, alkali metal bicarbonate, tri(lower)alkylamine (e.g. triethylamine, etc), pyridine, N-(lower)alkylmorpholine, N,N-di(lower)alkylbenzylamine, or the like.

The reaction temperature is not critical, and the reaction is usually carried out under cooling to heating.

The object compound (I) of the present invention is an adenosine antagonist and possesses the various pharmacological actions as stated before.

In order to show this usefulness of the compound (I) of the present invention, the pharmacological test result of the representative compound of the present invention is shown in the following.

Test 1. Effect on Cisplatin-induced Renal Failure

[I] Test Method

Male JCL:SD strain rats aged 9 weeks weighing 280–300 g received cisplatin (4.5 mg/kg) intraperitoneally. Normal rats were injected with an equal amount of saline instead of cisplatin. The effect of repeated intravenous administration of the test compound (0.1 mg/kg, twice a day) on cisplatin induced renal failure was investigated in rats. Cisplatin was given at the same time of the first dose of the test compound (for the test group) or vehicle (saline) (for the control group), and the test compound or vehicle was given for 3 days. The plasma creatinine concentrations were measured in all rats on the 8th day.

[II] Test Compound

3-[2-(2-Carboxymethyl-1-cycloheptenyl)-3-oxo-2,3-dihydropyridazin-6-yl]-2-phenylpyrazolo[1,5-a]-pyridine

[III] Test Results

|  | serum creatinine (mg/dl) |
| --- | --- |
| control group | 4.76 ±1.26 |

-continued

|  | serum creatinine (mg/dl) |
| --- | --- |
| test group | 1.32** 10.32 |

** p < 0.01 vs control group (each value was expressed as mean ± standard error)

Test 2. Effect on Cisplatin-induced Renal Failure

[I] Test Method

Male JCL:SD strain rats aged 9 weeks weighing 280–300 g received cisplatin (4.5 mg/kg) intraperitoneally. Normal rats were injected with an equal amount of saline instead of cisplatin. The effect of chronic intravenous administration of the test compound (0.1 mg/kg, twice a day) on cisplatin induced renal failure was investigated in rats. Cisplatin was given 60 minutes after the first dose of the test compound (for the test group) or vehicle (saline) (for the control group), and the test compound or vehicle was given for 8 days. The plasma creatinine concentrations were measured in all rats on the 8th day.

[II] Test Compound
3-[2-(2-Carboxymethyl-1-cyclohexenyl)-3-oxo-2,3-dihydropyridazin-6-yl]-2-phenylpyrazolo[1,5-a]-pyridine

[III] Test Results

|  | serum creatinine (mg/dl) |
| --- | --- |
| control group | 3.60 ±1.07 |
| test group | 1.10* ±0.45 |

*P < 0.05 vs control group (each value was expressed as mean ± standard error)

The pharmaceutical composition of this invention can be used in the form of a pharmaceutical preparation, for example, in solid, semisolid or liquid form, which contains the pyrazolopyridine compound (I) or a pharmaceutically acceptable salt thereof, as an active ingredient in a mixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation. The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used. The pyrazolopyridine compound (I) or a pharmaceutically acceptable salt thereof is/are included in the pharmaceutical composition in an amount sufficient to produce the desired aforesaid pharmaceutical effect upon the process or condition of diseases.

For applying the composition to human being or animals, it is preferable to apply it by intravenous, intramuscular, pulmonary, or oral administration, or insufflation. While the dosage of therapeutically effective amount of the pyrazolopyridine compound (I) varies from and also depends upon the age and condition of each individual patient to be treated, in the case of intravenous administration, a daily dose of 0.01–100 mg of the pyrazolopyridine compound (I) per kg weight of human being or animals, in the case of intramuscular administration, a daily dose of 0.1–100 mg of the pyrazolopyridine compound (I) per kg weight of human being or animals, in case of oral administration, a daily dose of 0.5–100 mg of the pyrazolopyridine compound (I) per kg weight of human being or animals generally given for the prevention and/or treatment of aforesaid diseases.

The following Preparations and Examples are given for the purpose of illustrating the present invention in more detail.

Preparation 1

To a mixture of 3,6-dichloropyridazine (5.0 g), bis(triphenylphosphine)palladium chloride (98% purity; 0.24 g), copper iodide (95% purity; 67 mg), tetra-n-butylammonium iodide (0.12 g), triethylamine (9.4 ml), and N,N-dimethylformamide (34 ml), was added a solution of phenylacetylene (5.5 ml) in N,N-dimethylformamide (17 ml) dropwise over a period of an hour. After the addition was completed, the mixture was allowed to stand at ambient temperature for 48 hours. The reaction mixture was concentrated in vacuo, and the residue was partitioned between dichloromethane and water. The organic layer was separated, washed with water and brine, dried over anhydrous magnesium sulfate, and concentrated in vacuo. The residue was subjected to column chromatography on silica gel (gradient elution, 10:1 n-hexane-dichloromethane to dichloromethane to 10:1 dichloromethane-ethyl acetate) to give 6-chloro-3-(2-phenylethynyl)pyridazine (3.2 g) and 3,6-bis(2-phenylethynyl)pyridazine (1.0 g). Some fractions containing the mixture thereof were subjected to flash column chromatography on silica gel (gradient elution, 10:1 n-hexane-dichloromethane to 25:1 dichloromethane-ethyl acetate to ethyl acetate) gave an additional product of 6-chloro-3-(2-phenylethynyl)pyridazine (0.50 g) and 3,6-bis(2-phenylethynyl)pyridazine (0.50 g).

1) 6-Chloro-(3-2-phenylethynyl)pyridazine: an analytical sample was recrystallized from diisopropyl ether. mp: 112–114° C.; IR (Nujol): 3050, 2220, 1560 cm$^{-1}$; NMR (CDCl$_3$, δ): 7.3–7.7 (7H, m); EIMS (m/z): 216 (M$^+$), 214 (M$^+$), 188, 186, 126 (base); Analysis Calcd. for C$_{12}$H$_7$ClN$_2$: C, 67.15, H, 3.29, N, 13.05; Found : C, 67.12, H, 3.31, N, 12.97.

2) 3,6-Bis(2-phenylethynyl)pyridazine: an analytical sample was recrystallized from ethyl acetate. mp: 180–182° C.; IR (Nujol): 2220, 1600, 1570 cm$^{-1}$; NMR (CDCl$_3$, δ): 7.3–7.7 (12H, m); EIMS (m/z): 280 (M$^+$), 252, 126 (base); Analysis Calcd. for C$_{20}$H$_{12}$N$_2$: C, 85.69, H, 4.31, N, 9.99; Found: C, 85.82, H, 4.30, N, 9.53.

Preparation 2

To a two-phase mixture of 6-chloro-3-(2-phenylethynyl)pyridazine (2.3 g), N-aminopyridinium iodide (90% purity; 5.3 g), benzyltrimethylammonium chloride (0.2.0 g), dichloromethane (23 ml), and water (23 ml) was added sodium hydroxide (3.4 g) in one portion. After stirring at ambient temperature overnight, the reaction mixture was treated with concentrated hydrochloric acid followed by dilution with dichloromethane and water. The organic layer was separated, and the aqueous layer was extracted once with dichloromethane. The combined organic layers were washed with water and brine, dried over anhydrous magnesium sulfate, and concentrated in vacuo. The residue was purified by column chromatography on silica gel (elution with 25:1 dichloromethane-ethyl acetate) to give 3-(3-chloropyridazin-6-yl)-2-phenylpyrazolo[1,5-a]pyridine (0.92 g).

mp: 206–206° C.; IR (Nujol): 1620, 1580 cm$^{-1}$; NMR (CDCl$_3$, δ): 6.9–7.0 (1H, m), 7.1–7.7 (8H, m), 6.4–6.6 (2H, m); EIMS (m/z): 308 (M$^+$), 307, 306 (M$^+$), 305 (base); Analysis Calcd. for C$_{17}$H$_{11}$ClN$_4$: C, 66.56, H, 3.61, N, 18.26; Found: C, 66.73, H, 3.58, N, 18.24.

Preparation 3

A 4:1 mixture of 6-chloro-3-(2-phenylethynyl)pyridazine and 3,6-bis(2-phenylethynyl)pyridazine (10.2 g) was stirred in a two-phase mixture of N-aminopyridinium iodide (90% purity; 11 g), benzyltrimethylammonium chloride (1.4 g), sodium hydroxide (5.9 g), dichloromethane (51 ml) and water (51 ml) at ambient temperature for an hour. The reaction mixture was diluted with dichloromethane and water. The organic layer was separated, and the aqueous layer was extracted once with dichloromethane. The combined organic layer was washed with water and brine, dried over anhydrous magnesium sulfate, and concentrated in vacuo. The residue was subjected to column chromatography on silica gel (elution with 25:1 dichloromethane-ethyl acetate) to give 3-(3-chloropyridazin-6-yl)-2-phenylpyrazolo[1,5-a]pyridine (0.72 g) and 3-[3-(2-phenylethynyl)pyridazin-6-yl]-2-phenylpyrazolo[1,5-a]pyridine (0.5 g). Some fractions containing the mixture thereof were subjected to flash column chromatography on silica gel (elution with 50:1 dichloromethane-ethyl acetate) gave an additional product of 3-(3-chloropyridazin-6-yl)-2-phenylpyrazolo[1,5-a]pyridine (0.34 g) and 3-[3-(2-phenylethynyl)pyridazin-6-yl]-2-phenylpyrazolo[1,5-a]pyridine (0.50 g).

3-[3-(2-Phenylethynyl)pyridazin-6-yl]-2-phenylpyrazolo[1,5-a]pyridine (an analytical sample was recrystallized from ethyl acetate.)

mp: 196–198° C.; NMR (CDCl$_3$, δ): 6.9–7.0 (1H, m), 7.1–7.7 (13H, m), 8.4–8.6 (2H, m); EIMS (m/z): 373, 372 (M$^+$), 371 (base), 343, 218; Analysis Calcd. for C$_{25}$H$_{16}$N$_4$: C, 80.63, H, 4.33, N, 15.04; Found: C, 80.78, H, 4.42, N, 15.06.

Preparation 4

4-Aminobutyric acid (7.5 g) was dissolved in a mixture of tetrahydrofuran (80 ml) and water (80 ml), which was cooled at 0 to 5° C. in an ice bath. To a resulting mixture was added dropwise benzyloxycarbonyl chloride (10.4 ml) with maintaining the pH from pH 8.0 to 9.0 with 30% aqueous sodium hydroxide solution at 0 to 5° C. The reaction mixture was washed with ethyl acetate (300 ml) and aqueous layer was separated, which was adjusted to pH 1.0 with 6N-aqueous hydrochloric acid and extracted with ethyl acetate (300 ml). Organic layer was separated, washed with brine (100 ml×2) and dried over magnesium sulfate. Evaporation of the solvent gave a residue, which was dissolved in methanol (200 ml) and added conc. sulfic acid (1 ml). The resulting solution was refluxed for 3 hours. Evaporation of the solvent gave a residue, which was dissolved In ethyl acetate (300 ml), washed in turn with water (100 ml), saturated sodium hydrogen carbonate in water (100 ml×3) and brine (100 ml×2), and dried over magnesium sulfate. Solvent was removed under reduced pressure to give methyl 4-(benzyloxycarbonylamino)butyrate (14.65 g).

NMR (CDCl$_3$, δ): 1.76–1.90 (2H, m), 2.36 (2H, t, J=7.2 Hz), 3.23 (2H, m), 3.66 (3H, s), 4.97 (1H, br s), 5.09 (2H, s), 7.29–7.37 (5H, m); (+)-APCI/MS: 252 (M$^+$+1).

Preparation 5

Ethyl 3-aminopropionate hydrochloride (10 g) was dissolved in a mixture of tetrahydrofuran (100 ml) and water, which was cooled at 0 to 5° C. in an ice bath and adjusted to pH 8.2 with 30% aqueous sodium hydroxide solution. To a resulting solution was added with care benzyloxycarbonyl chloride (10.3 ml), with maintaining the pH from pH 8.0 to 9.0 with 30% aqueous sodium hydroxide solution at 0 to 5° C. The reaction mixture was extracted with ethyl acetate (300 ml) and organic layer was separated, which was washed two times with saturated sodium chloride in water and dried over magnesium sulfate. Solvent was removed under reduced pressure to give ethyl 3-(benzyloxycarbonylamino)-propionate (15.3 g).

NMR (DMSO-d$_6$, δ): 1.17 (3H, t, J=7.1 Hz), 2.45 (2H, t, J=6.8 Hz), 3.19–3.29 (2H, m), 4.05 (2H, q, J=7.1 Hz), 5.01 (2H, s), 7.29–7.41 (5H, m); (+)-APCI/MS: 252 (M$^+$+1).

Preparation 6

To a suspension of sodium hydride (1.92 g, 60% in Oil) in a mixture of tetrahydrofuran (200 ml) and N,N-dimethylformamide (50 ml) was added dropwise ethyl 3-(benzyloxycarbonylamino)propionate (10 g) at 30° C. under nitrogen atmosphere, which was stirred for 30 minutes. To the reaction mixture was added methyl iodide (3 ml) and stirred for additional 6 hours. To the resulting mixture was added carefully water (5 ml), which was poured into a mixture of ethyl acetate (500 ml), n-hexane (150 ml) and water (100 ml). Organic layer was separated, washed n turn with water (100 ml×3), 1N-aqueous hydrochloric acid (100 ml), brine (100 ml), saturated sodium hydrogen carbonate in water (100 ml) and brine (100 ml×2), and dried over magnesium sulfate. Evaporation of the solvent gave a residue, which was chromatographed on silica gel (250 ml) eluting In turn with n-hexane, 10%, 50% ethyl acetate in n-hexane to give ethyl 3-(N-benzyloxycarbonyl-N-methylamino)propionate (8.32 g).

NMR (CDCl$_3$, δ): 1.24 (3H, t, J=7.1 Hz), 2.45–2.70 (2H, m), 2.58 (3H, s), 3.58 (2H, t, J=7.0 Hz), 4.12 (2H, q, J=7.1 Hz), 5.13 (2H, s), 7.28–7.38 (5H, m).

Preparation 7

A mixture of ethyl 3-(N-benzyloxycarbonyl-N-methylamino)propionate (8 g), 10% palladium on carbon (1.6 g, 50% wet), conc.-hydrochloric acid (5.1 ml) in methanol (160 ml) was stirred for 5 hours at room+temperature under hydrogen atmosphere. Catalyst was removed by filtration and mother liquor was concentrated in reduced pressure to give ethyl 3-(methylamino)propionate hydrochloride (4.31 g).

NMR (DMSO-d$_6$, δ): 1.21 (3H, t, J=7.1 Hz), 2.70–2.83 (2H, m), 3.00–3.20 (2H, m), 4.10 (2H, q), 9.12 (1H, br s).

Preparation 8

Methyl 4-aminobutyrate hydrochloride was obtained in substantially the same manner as that of Preparation 7.

NMR (DMSO-d$_6$, δ): 1.77–1.92 (2H, m), 2.46 (2H, t, J=7.5 Hz), 2.72–2.85 (2H, m), 3.61 (3H, s), 8.28 (2H, br s); (+)-APCI/MS: 118 (M$^+$+1-HCl).

Preparation 9

To a solution of 1,3-cyclohexanediol (cis and trans mixture, 25 g) and imidazole (8.8 g) in a mixture of dichloromethane (150 ml) and tetrahydrofuran (150 ml) was added dropwise a solution of tert-butyldimethylsilyl chloride (16.2 g) in a mixture of dichloromethane (40 ml) and tetrahydrofuran (40 ml) at 0° C. A reaction mixture was allowed to warm to ambient temperature and stirred overnight. Insoluble material was removed by filtration and mother liquor was concentrated under reduced pressure to give residue, which was dissolved in ethyl acetate (300 ml) and washed in turn with 1N aqueous hydrochloric acid (100 ml), brine (100 ml), saturated sodium hydrogen carbonate in water (100 ml), and saturated sodium chloride in water, and dried over magnesium sulfate. Evaporation of the solvent gave a residue, which was chromatographed on silica gel (500 ml) eluting in turn with 10% and 20% ethyl acetate in n-hexane to give 3-(tert-butyldimethylsilyl)oxy-1-cyclohexanol (cis and. trans mixture) (12.52 g).

FT IR (Nujol): 3361.3, 1465.6, 1365.4 cm$^{-1}$; NMR (CDCl$_3$, δ): 0.08 (6H, s), 0.88, 0.90 (9H (1:2.3), 2×s), 1.20–2.10 (8H, m), 3.75–4.20(2H, m); (+)-APCI/MS: 231 (M$^+$+1).

Preparation 10

To a solution of 3-(tert-butyldimethylsilyl)oxy-1-cyclohexanol (12.5 g) and triethylamine (9.8 ml) in dichloromethane (200 ml) was added dropwise methylsulfonyl-chloride (4.6 ml) at 5° C. under nitrogen atmosphere. A reaction mixture was allowed to warm to ambient temperature and stirred or 2 hours. Insoluble material was removed by filtration and mother liquor was concentrated under reduced pressure to give residue, which was dissolved in ethyl acetate (200 ml) and washed in turn with 1N-aqueous hydrochloric acid (50 ml×2), saturated sodium hydrogen carbonate in water (50 ml×2) and saturated sodium chloride in water (50 ml×2), and dried over magnesium sulfate. Evaporation of the solvent gave a residue, which was chromatographed on silica gel (300 ml) eluting with 10% ethyl acetate in n-hexane to give 3-(tert-butyldimethylsilyl)oxy-1-(methylsulfonyloxy)-cyclohexane(cis and trans mixture, 16.0 g).

FT IR (Nujol): 1467.6, 1357.6 cm$^{-1}$; NMR (CDCl$_3$, δ): 0.06 (6H, s), 0.88, 0.89 (9H (2:1), 2×s), 1.15–2.30 (8H, m), 2.93, 2.95 (3H (1:2), 2×s), 3.45–3.63, 4.00–4.15 (1H (2:1), 2×m), 4.40–4.63, 4.90–5.05 (1H (2:1), 2×m); (+)-APCI/MS: 309 (M$^+$+1).

Preparation 11

A solution of 3-(tert-butyldimethylsilyl)oxy-1-(methylsulfonyloxy)cyclohexane (15.9 g) and sodium iodide (8.5 g) in N,N-dimethylformamide (80 ml) was heated at 100° C. for 3 hours with stirring. After cooled to ambient temperature, a reaction mixture was poured into a mixture of ethyl acetate (250 ml) and n-hexane (150 ml), and insoluble material was removed by filtration. Mother liquor was washed in turn with water (100 ml×3), 5% sodium thiosulfate in water (50 ml), and saturated sodium chloride in water (100 ml×2), and dried over magnesium sulfate. Evaporation of the solvent gave a residue, which was chromatographed on silica gel (300 ml) eluting with 10% ethyl acetate in n-hexane to give 3-(tert-butyldimethylsilyl)oxy-1-iodocyclohexane (cis and trans mixture).

FT IR (Nujol): 1461.8, 1373.1 cm$^{-1}$; NMR (CDCl$_3$, δ): 0.05, 0.07 (6H (1.2:1), 2×s), 0.87, 0.89 (9H (1:2.3), 2×s), 1.20–2.65 (8H, m), 3.40–4.10 (1H, m), 4.60–4.75, 5.45–5.75 (1H (1:2.7), 2×m); (+)-APCI/MS: 341 (M$^+$+1).

Preparation 12

To a solution of 1,2,3,6-tetrahydropyridine (10 g) in tetrahydrofuran (100 ml) was added di-tert-butyl dicarbonate (25.2 g) and catalytic amount of 4-dimethylaminopyridine at 0° C. A reaction mixture was allowed to warm to ambient temperature and stirred for 15 hours. Evaporation of the solvent gave a residue, which was dissolved in ethyl acetate (300 ml), washed in turn with 1N-aqueous hydrochloric acid (100 ml), saturated sodium chloride in water (100 ml), saturated sodium hydrogen carbonate in water (100 ml) and saturated sodium chloride in water (100 ml), which was dried over magnesium sulfate. Solvent was removed under reduced pressure to give 1-tert-butoxycarbonyl-1,2,3,6-tetrahydropyridine (19.9 g).

FT IR (Neat): 1704.8 cm$^{-1}$; NMR (CDCl$_3$, δ): 1.47 (9H, s), 2.13 (2H, br s), 3.49 (2H, t, J=5.7 Hz), 3.88 (2H, t, J=2.5 Hz), 5.60–5.90 (2H, m).

Preparation 13

To a solution of 1-tert-butoxycarbonyl-1,2,3,6-tetrahydropyridine (18.9 g) in dichloromethane (400 ml). was added in turn sodium hydrogen carbonate (11.3 g) and m-chloroperoxybenzoic acid (23.4 g) with care at 0° C., and which was stirred for 2 hours. Insoluble material was removed by filtration, mother liquor was washed saturated sodium chloride in water (100 ml) and dried over magnesium sulfate. Evaporation of the solvent gave a residue, which was dissolved in n-hexane (300 ml) and insoluble material was removed by filtration. Mother liquor was concentrated in vacuo, the remainings were dissolved in ethyl acetate (300 ml) and washed in turn with saturated sodium hydrogen carbonate in water (100 ml×5) and saturated sodium chloride in water (100 ml×2), which was dried over magnesium sulfate. Evaporation of the solvent gave a residue, which was chromatographed on silica gel (350 ml) eluting in turn with 10%, 20% and 30% ethyl acetate in n-hexane. Tractions, containing desired product, were collected and concentrated in vacuo to give 1-tert-butoxycarbonyl-3,4-epoxypiperidine (13.7 g).

NMR (CDCl$_3$, δ): 1.45 (9H, s), 1.75–2.10 (2H, m), 3.00–4.00 (6H, m).

Preparation 14

A mixture of 1-hydroxy-5-oxo- 5,6,7,8-tetrahydronaphthalene (10 g), potassium carbonate (9.4 g), methyl bromoacetate (6.2 ml) in acetonitrile (250 ml) was refluxed with stirring for 3.5 hours. The mixture was filtered off and the filtrate was evaporated in vacuo. The residue was partitioned between ethyl acetate and water. The separated organic layer was wasted with 1N-hydrochloric acid, 1N-sodium hydroxide, brine, dried over magnesium sulfate and evaporated in vacuo. The residue was suspended in n-hexane and then the solid was collected by filtration to give 1-methoxycarbonylmethoxy-5-oxo-5,6,7,8-tetrahydronaphthalene (13.90 g).

mp: 82–83° C.; IR (Nujol): 1755, 1670, 1590, 1570 cm$^{-1}$; NMR (CDCl$_3$, δ): 2.04–2.19 (2H, m), 2.64 (2H, t, J=6.1 Hz), 2.99 (2H, t, J=6.1 Hz), 3.81 (3H, s), 4.69 (2H, s), 6.89 (1H, d, J=8.1 Hz), 7.20–7.28 (1H, m), 7.60 (1H, d, J=7.9 Hz); (+)-APCI/MS: 235 (M$^+$+1). Analysis Calcd. for C$_{13}$H$_{14}$O$_4$: C, 66.66, H, 6.02; Found: C, 66.99, H, 6.16.

Preparation 15

To a solution of 1-methoxycarbonylmethoxy-5-oxo-5,6,7,8-tetrahydronaphthalene (0.5 g) in dry dichloromethane (3 ml) was added bromine (0.14 ml) at 0° C. The mixture was warmed up to room temperature, stirred for 2 hours. The mixture was washed with an aqueous saturated sodium bicarbonate, dried over magnesium sulfate and evaporated in vacuo. The residue was chromatographed on silica gel (30 ml) using a mixture of dichloromethane-n-hexane. The desired fractions were collected and evaporated in vacuo to give 1-methoxycarbonylmethoxy-5-oxo-6-bromo- 5,6,7,8-tetrahydronaphthalene (0.41 g). The crude crystal (50 mg) was recrystallized from ethyl acetate-n-hexane to give 31 mg as a white crystal.

mp: 76–77° C.; IR (Nujol): 1755, 1680, 1590, 1575 cm$^{-1}$; NMR (CDCl$_3$, δ): 2.49 (2H, dd, J=5.8, 10.3 Hz), 3.08–3.15 (2H, m), 3.82 (3H, s), 4.69–4.74 (1H, ml, 4.71 (2H, s), 6.94 (1H, d, J=8.0 Hz), 7.25–7.33 (1H, m), 7.75 (1H, d, J=8.0 Hz); (+)-APCI/MS: 315 (M$^+$+2); Analysis Calcd. for C$_{13}$H$_{13}$BrO$_4$: C, 49.86, H, 4.18; Found C, 49.79, H, 4.14.

EXAMPLE 1

A mixture of 3-(3-oxo-2,3-dihydropyridazin-6-yl)-2-phenylpyrazolo[1,5-a]pyridine (14.44 g) and cyclohexyl bromide (18.5 ml) and a 40%-methanol solution of benzyl-trimethylammoniumhydroxide (61.5 ml) in dimethoxy-ethane (140 ml) was heated at 70° C. for 60 hours with stirring. The mixture was evaporated under reduced pressure. The residue was partitioned between dilute aqueous hydrochloric acid and ethyl acetate and then the insoluble starting material was filtered off. The separated organic layer was washed with an aqueous solution of sodium bicarbonate, dried over magnesium sulfate, and evaporated under reduced pressure. The residue was purified by column chromatography on silica gel (600 ml) using a mixture of dichloromethane and methanol. The desired fractions were collected and evaporated under reduced pressure. The residue was dissolved in 100 ml of a mixture of dichloromethane and ethanol (1:1) and then the mixture was evaporated under reduced pressure to give about 15 ml solution. The resultant solution was diluted with ethanol (10 ml). The resulting yellow crystals were collected by filtration to give 3-(2-cyclohexyl-3-oxo-2,3-dihydropyridazin-6-yl)-2-phenylpyrazolo[1,5-a]pyridine (5.93 g).

mp: 115–117° C.; IR (Nujol): 1655, 1585 cm$^{-1}$; NMR (DMSO-d$_6$, δ): 1.20–1.85 (10H, m), 4.70–4.90 (1H, m), 6.87 (1H, d, J=9.6 Hz), 7.08 (1H, dt, J=1.3 Hz, 7.0 Hz), 7.15 (1H, d, J=9.6 Hz), 7.30–7.61 (6H, m), 7.88 (1H, d, J=9 Hz), 8.80 (1H, d, J=7 Hz); EIMS (m/z): (M$^+$)=370; Analysis Calcd. for C$_{23}$H$_{22}$N$_4$O, 1/4 EtOH: C, 73.90, H, 6.20, N, 14.67; Found: C, 74.06, H, 6.51, N, 14.44.

EXAMPLE 2

To a solution of 3-(3-oxo-2,3-dihydropyridazin-6-yl)-2-phenylpyrazolo[1,5-a]pyridine (6.96 g) in 100 ml of N,N-dimethylformamide was added sodium hydride (60% dispersion in mineral oil, 1.06 g) at 5–10° C. The mixture was starred for 30 minutes at 5° C., then to this was added dropwise a solution of 2-chlorocyclohexanone (4.81 g) in 10 ml of N,N-dimethylformamide at 5° C. over a period of 10 minutes. The mixture was allowed to stir at room temperature for 1 hour and then heated to 120° C. for 8.5 hours. The reaction mixture was poured. into ice-water (300 ml) and the mixture was extracted with ethyl acetate (100 ml×2). The combined extracts were washed with water (100 ml) and brine (50 ml), dried over magnesium sulfate, and concentrated in vacuo. The crude materials were purified by column chromatography on silica gel (200 g) eluted with a mixture of toluene and ethyl acetate (10:1) to give two compounds; the less polar compound, pale yellow crystals of 3-[3-(2-oxocyclohexyl)oxy-pyridazin-6-yl]-2-phenylpyrazolo[1,5-a]pyridine (3.76 g) and the more polar compound, ale yellow crystals of 3-[2-(2-oxocyclohexyl)-3-oxo-2,3-dihydropyridazin-6-yl]-2-phenylpyrazolo[1,5-a]pyridine (2.35 g).

3-[3-(2-Oxocyclohexyl)oxypyridazin-6-yl]-2-phenylpyrazolo[1,5-a]pyridine mp: 214 to 216° C. (EtOH-EtOAc); IR (Nujol): 1725, 1620, 1600 cm$^{-1}$; NMR (CDCl$_3$, δ): 2.00–2.21 (5H, m), 2.26–2.63 (3H, m), 5.98 (1H, dd, J=11.8 Hz, 6.4 Hz), 6.90 (1H, d, J=6.3 Hz), 6.89 (1H, t, J=7.0 Hz), 7.19 (1H, d, J=9.3 Hz), 7.27 (1H, t, J=7.0 Hz), 7.42–7.46 (3H, m), 7.58–7.62 (2H, m), 8.27(1H, d, J=7.0 Hz), 8.52 (1H, d, J=7.0 Hz); Analysis Calcd. for C$_{23}$H$_{20}$N$_4$O$_2$: C, 71.86, H, 5.24, N, 14.57; Found: C, 71.51, H, 5.20, N, 14.48.

3-[2-(2-oxocyclohexyl)-3-oxo-2,3-dihydropyridazin-6-yl]-2-phenylpyrazolo[1,5-a]pyridine mp: 166–168° C. (EtOAc-IPE); IR (Nujol): 1720, 1660, 1585, 1520 cm$^{-1}$; NMR (CDCl$_3$, δ): 1.65–2.26 (4H, m), 2.34–2.73 (4H, m), 5.79 (1H, dd, J=11.7 Hz, 7.1 Hz), 6.179 (1H, d, J=9.7 Hz), 6.88 (1H, t, J=6.9 Hz), 7.03 (1H, d, J=9.7 Hz), 7.28 (1H, t, J=6.9 Hz), 7.43–7.48 (3H, m), 7.61–7.66 (2H, m), 7.88 (2H, d, J=6.9 Hz), 8.51 (1H, d, J=6.9 Hz); Analysis Calcd. for C$_{23}$H$_{20}$N$_4$O$_2$: C, 71.86, H, 5.24, N, 14.57; Found: C, 71.71, H, 5.12, N, 14.40.

EXAMPLE 3

3-[2-(2-Oxocyclopentyl)-3-oxo- 2,3-dihydropyridazin-6-yl]-2-phenylpyrazolo[1,5-a]pyridine was obtained according to a similar manner to that of Example 2.

mp: 167–168° C. (EtOAc-IPE); IR (Nujol): 1740, 1660, 1630, 1590, 1520 cm$^{-1}$; NMR (CDCl$_3$, δ): 1.86–2.12 (1H, m), 2.00–2.68 (5H, m), 5.36 (1H, dd, J=11.0 Hz, 8.5 Hz), 6.77 (1H, d, J=9.7 Hz), 6.90 (1H, t, J=7.0 Hz), 7.01 (1H, d, J=9.7 Hz), 7.29 (1H, t, J=8.0 Hz), 7.44–7.49 (3H, m), 7.59–7.64 (2H, m), 7.85 (1H, d, J=8.0 Hz), 8.51 (1H, d, J=7.0 Hz); Analysis Calcd. for C$_{22}$H$_{18}$N$_4$O: C, 71.34, H, 4.90, N, 15.13; Found: C, 70.92, H, 4.79, N, 14.97.

EXAMPLE 4

To a suspension of 3-[2-(2-oxocyclohexyl)-3-oxo-2,3-dihydropyridazin-6-yl]-2-phenylpyrazolo[1,5-a]pyridine (679 mg) in 14 ml of tetrahydrofuran was added lithium tri-tert-butoxyaluminohydride (676 mg) at 5° C. The reaction mixture was allowed to stir at 5–10° C. for 45 minutes, then the solvent was removed in vacuo. To the residue was added 20 ml ice-water. Then, the mixture was acidified with 1N hydrochloric acid and extracted with dichloromethane (25 ml×2). The combined extracts were washed with water (20 ml) and brine (20 ml), dried over sodium sulfate, and concentrated in vacuo. The residue was purified by column chromatography on silica gel (30 g) eluted with a mixture of dichloromethane and ethyl acetate (10:3) to give pale yellow crystals of cis-3-[2-(2-hydroxycyclohexyl)-3-oxo-2,3-dihydropyridazin-6-yl]-2-phenylpyrazolo[1,5-a]pyridine (677.4 mg).

mp: 195–197° C. (EtOAc-IPE); IR (Nujol): 3400, 1650, 1580, 1525 cm$^{-1}$; NMR (CDCl$_3$+D$_2$O, δ): 1.48–2.05 (7H, m), 2.18–2.39 (1H, m), 4.37 (1H, br s), 4.99 (1H, dm, J=10.7 Hz), 6.82 (1H, d, J=9.6 Hz), 6.96 (1H, t, J=6.9 Hz), 7.05 (1H, d, J=9.6 Hz), 7.36 (1H, 5, t, J=8.0 Hz), 7.44–7.47 (3H, m), 7.57–7.62 (2H, m), 7.89 (1H, d, J=8.0 Hz), 8.54 (1H, d, J=6.9 Hz); Analysis Calcd. for C$_{23}$H$_{22}$N$_4$O$_2$.1H$_2$O: C, 68.05, H, 5.98, N, 13.85; Found: C, 67.76, H, 6.11, N, 13.66.

EXAMPLE 5

To a solution of 3-(3-oxo-2,3-dihydropyridazin-6-yl)-2-phenylpyrazolo[1,5-a]pyridine (1.58 g) in 80 ml of N,N-dimethylformamide was added sodium hydride (60% dispersion in Mineral oil, 242 mg) at 5° C. After being stirred for 15 minutes at 5° C., the mixture was treated with epoxycyclohexane (1.62 g) and heated to 127° C. for 4.5 hours. The reaction mixture was poured into ice-water (200 ml), and the mixture was extracted with ethyl acetate (100 ml, 50 ml). The combined extracts were washed with water (50 ml) and brine (50 ml), dried over sodium sulfate, and concentrated in vacuo. The crude materials were purified by column chromatography on silica gel (40 g). The fractions containing minor cis isomer eluted with a mixture of dichloromethane and ethyl acetate (10:1–10:2) were collected, and the solvent was removed in vacuo to give cis-3-[2-(2-hydroxycyclohexyl)-3-oxo-2,3-dihydropyridazin-6-yl]-2-phenylpyrazolo(1,5-a pyridine (65.1 mg). The physical data for this compound were idendical with those of the authentic sample prepared by the method described in Example 4.

On the other hand, the fractions containing major trans isomer eluted with a mixture of dichloromethane and methanol (10:1) were collected and the solvent was removed in vacuo to give pale yellow crystals of trans-3-[2-(2-hydroxycyclohexyl)-3-oxo-2,3-dihydropyridazin-6-yl]-2-phenylpyrazolo[1,5-a]-pyridine (1.48 g).

mp: 229–230° C. (EtOH-EtOAc); IR (Nujol): 3370, 1650, 1580, 1520, 1495 cm$^{-1}$; NMR CDCl$_3$+D$_2$O, δ): 1.19–2.62 (3H, m), 1.73-2.23 (5H, m), 3.96 (1H, td, J=10.0 Hz, 4.3 Hz), 4.94 (1H, td, J=10.0 Hz, 4.3 Hz), 6.78 (1H, d, J=9.6 Hz), 6.91 (1H, t, J=7.0 Hz), 7.02 (1H, d, J=9.6 Hz), 7.31 (1H, t, J=8.0 Hz), 7.42–7.47 (3H, m), 7.57–7.63 (2H, m), 7.93 (1H, d, J=8.0 Hz), 8.53 (1H, d, J=7.0 Hz); Analysis Calcd. for C$_{23}$H$_{22}$N$_4$O$_2$: C, 71.48, H, 5.74, N, 14.50; Found: C, 71.62, H, 5.71, N, 14.45.

EXAMPLE 6

To a solution of trans-3-[2-(2-hydroxycyclohexyl)-3-oxo-2,3-dihydropyridazin-6-yl]-2-phenylpyrazolo[1,5-a]-pyridine (157 ng) in 20 ml of dichloromethane was added pyridium dichromate (307 mg) and molecular sieves 4A (144 mg) at 50° C. The reaction mixture was allowed to stir at room temperature for 28.5 hours. Insoluble material was filtered off using celite and the filtrate was washed with 1N hydrochloric acid (10 ml), saturated aqueous sodium bicarbonate (10 ml), and brine (10 ml), dried over sodium sulfate, and concentrated in vacuo. The crude material was purified by column chromatography on silica gel (2 g) eluted with a mixture of dichloromethaneand ethyl acetate (4:1) to give 3-[2-(2-oxocyclohexyl)-3-oxo-2,3-dihydropyridazin-6-yl]-2-phenylpyrazolo[1,5-a]pyridine (116.5 mg). The nmr spectrum for this compound was identical with that of the authentic sample prepared by the method described in Example 2.

EXAMPLE 7

To a solution of triethyl phosphonoacetate (414 mg) in 10 ml of toluene was added sodium hydride (60% dispersion in mineral oil, 74 mg) at 5° C. To the mixture was added 3-[2-(2-oxocyclohexyl)-3-oxo-2,3-dihydropyridazin-6-yl]-2-phenylpyrazolo[1,5-a]pyridine. After being warmed up to room temperature, the reaction mixture was heated to 100° C. for 3 hours. Toluene was removed in vacuo and the residue was partitioned between water (30 ml) and dichloromethane (30 ml). After an additional extraction with dichloromethane (20 ml), the combined extracts were washed with saturated aqueous sodium bicarbonate (20 ml) and brine (30 ml), dried over sodium sulfate, and concentrated in vacuo. The residue was dissolved in 10 ml of methanol. To this was added 1N aqueous sodium hydroxide solution (4 ml) and the mixture was stirred at room temperature for 20 hours and 45 minutes. 1N aqueous sodium hydroxide solution (1 ml) was added to the mixture again, and the mixture was allowed to stir for additional 17 hours. The solvent was removed in vacuo and the residue was partitioned between water and ethyl acetate. The aqueous layer was then acidified with 1N hydrochloric acid and the mixture was extracted with dichloromethane (20 ml×2). The combined extracts were washed with brine (10 ml), dried over sodium sulfate, and concentrated in vacuo. The residue was purified by column chromatography on silica gel (merck 270–400 mesH, 25 g) eluted with a mixture of dichloromethane and ethyl acetate (1:1) to give following two compounds.

(a) 3-[2-(2-Carboxymethylenecyclohexyl)-3-oxo- 2,3-dihydropyridazin-6-yl]-2-phenylpyrazolo[1,5-a]-pyridine (E or Z isomer) (58.9 mg after recrystallization from ethyl acetate)

mp: 200–241° C.; IR (Nujol): 1700, 1640, 1575 cm$^{-1}$; NMR (CDCl$_3$, δ): 1.40–2.22 (7H, m), 4.07 (1H, d, J=14.1 Hz), 5.16 (1H, s), 5.66 (1H, dd, J=10.5 Hz, 3.5 Hz), 6.82 (1H, d, J=9.6 Hz), 6.91 (1H, t, J=7.0 Hz), 7.05 (1H, d, J=9.6 Hz), 7.31 (1H, t, J=8.0 Hz), 7.44–7.48 (3H, m), 7.58–7.63 (2H, m), 7.90 (1H, d, J=8.0 Hz), 8.54 (1H, d, J=7.0 Hz); (+)-APCI/MS: 427 (M$^+$+1).

(b) 3-[2-(2-Carboxymethyl-1-cyclohexenyl)-3-oxo-2,3-dihydropyridazin-6-yl]-2-phenylpyrazolo[1,5-a]-pyridine (156 mg, after recrystallization from a mixture of ethyl acetate and diisopropyl ether)

mp: 194–195° C.; IR (Nujol): 1710, 1630, 1565, 1520 cm$^{-1}$; NMR (CDCl$_3$, δ): 1.66–2.03 (4H, m), 2.07–2.66 (4H, m), 2.91 (1H, d, J=14.0 Hz), 3.15 (1H, d, J=14.0 Hz), 6.91 (1H, d, J=9.6 Hz), 6.94 (1H, t, J=7.0 Hz), 7.15 (1H, d, J=9.6 Hz), 7.36 (1H, t, J=8.0 Hz), 7.94 (1H, d, J=8.0 Hz), 8.56 (1H, d, J=7.0 Hz); (+)-APCI/MS: 427 (M$^+$+1); Analysis Calcd. for C$_{25}$H$_{22}$N$_4$O$_3$: C, 70.41, H, 5.20, N, 13.14; Found: C, 70.29, H, 5.21, N, 13.05.

The following compounds (Examples 8 and 9) were obtained according to a similar manner to that of Example 5.

EXAMPLE 8

3-[2-{(1R*,2R*,4S*)-2-Hydroxy-4-methoxycarbonyl-cyclohexyl}-3-oxo-2,3-dihydropyridazin-6-yl]-2-phenylpyrazolo[1,5-a]pyridine mp: 169–172° C. (EtOAc); IR (Nujol): 3380, 1720, 1650, 1580, 1530 cm$^{-1}$; NMR (CDCl$_3$, δ): 1.59–2.25 (7H, m), 2.50 (2H, m), 3.00 (1H, br s), 3.71 (3H, s), 4.1 (1H, m), 4.97 (1H, dt, J=4.1 Hz, 11.0 Hz), 6.78 (1H, d, J=9.6 Hz), 6.95 (1H, dt, J=1.2 Hz, 6.9 Hz), 7.05 (1H, d, J=9.6 Hz), 7.31 (1H, t, J=8.9 Hz), 7;27–7.36 (3H, m), 7.57–7.87 (2H, m), 7.89 (1H, d, J=8.9 Hz), 8.54 (1H, d, J=6.9 Hz); (+)-APCI/MS: 445 (M$^+$+1); Analysis Calcd. for C$_{25}$H$_{24}$N$_4$O$_4$.1H$_2$O: C, 64.92, H, 5.66, N, 12.11; Found: C, 64.68, H, 5.54, N, 11.81.

EXAMPLE 9 trans-3-[2-(2-Hydroxycycloheptyl)-3-oxo-2,3-dihydropyridazin.-6-yl]-2-phenylpyrazolo[1,5-a]pyridine mp: 181–182° C. (EtOAc); IR (Nujol): 3360, 1650, 1590, 1530 cm$^{-1}$; NMR (CDCl$_3$, δ): 1.40–2.10 (10H, m), 2.96 (1H, d, J=5.10 Hz), 4.05–4.20 (1H, m), 5.12 (1H, dt, J=3.5 Hz, 8.9 Hz), 6.80 (1H, d, J=9.62 Hz), 6.92 (1H, dt, J=1.40 Hz, 6.95 Hz), 7.04 (1H, d, J=9.62 Hz), 7.32 (1H, dt, J=1.40 Hz, 6.8 Hz), 7.42–7.49 (3H, m), 7.57–7.64 (2H, m), 7.93 (1H, dd, J=1.40 Hz, 8.94 Hz), 8.53 (1H, dd, J=1.40 Hz, 6.95 Hz); Analysis Calcd. for C$_{24}$H$_{24}$N$_4$O$_2$.1/4H$_2$O: C, 71.18, H, 6.10, N, 13.83; Found: C, 71.35, H, 6.06, N, 13.98.

The following compounds (Examples 10 and 11) were obtained according to a similar manner to that of Example 6.

EXAMPLE 10 cis-3-[2-(4-Methoxycarbonyl-2-oxocyclohexyl)-3-oxo-2,3-dihydropyridazin-6-yl]-2-phenylpyrazolo[1,5-a]pyridine mp: 164–165° C.; IR (Nujol): 1725, 1660, 1590 cm$^{-1}$; NMR (CDCl$_3$, δ): 2.05–2.21 (1H, m), 2.40–2.53 (3H, m), 2.78–2.90 (3H, m), 3.76 (3H, S), 5.76 (1H, dd, J=7.3 Hz, 6.5 Hz), 6.80 (1H, d, J=9.6 Hz), 6.90 (1H, dt, J=1.4 Hz, 6.9 Hz), 7.05 (1H, d, J=9.6 Hz), 7.28 (1H, t, J=8.0 Hz), 7.44–7.47 (3H, m), 7.60–7.65 (2H, m), 7.84 (1H, d, J=8.0 Hz), 8.51 (1H, d, J=6.9 Hz); (+)-APCI/MS: 443 (M$^+$+1); Analysis Calcd. for C$_{25}$H$_{22}$N$_4$O$_4$.1/2H$_2$O: C, 66.51, H, 5.13, N, 12.41; Found: C, 66.24, H, 4.98, N, 12.01.

EXAMPLE 11

3-[2-(2-Oxocycloheptyl)-3-oxo-2,3-dihydropyridazin-6-yl]-2-phenylpyrazolo[1,5-a]pyridine mp: 112–114° C. (IPE); IR (Nujol): 1710, 1660, 1630, 1590, 1530 cm$^{-1}$; NMR (CDCl$_3$, δ): 1.44–2.30 (8H, m), 2.56–2.72 (1H, m), 2.78–2.95 (1H, m), 5.72 (1H, dd, J=4.0 Hz, 9.4 Hz), 6.76 (1H, d, J=9.7 Hz), 6.89 (1H, dt, J=1.1 Hz, 6.9 Hz), 7.03 (1H, d, J=9.7 Hz), 7.28 (1H, dt, J=1.1 Hz, 6.9 Hz), 7.42–7.49 (3H, m), 7.57–7.88 (2H, m), 7.90 (1H, dd, J=1.1 Hz, 7.8 Hz), 8.50 (1H, dd, J=1.1 Hz, 6.9 Hz); Analysis Calcd. for C$_{24}$H$_{22}$N$_4$O$_2$.H$_2$O: C, 69.22, H, 5.81, N, 13.45; Found: C, 69.60, H, 5.37, N, 13.39.

EXAMPLE 12

The following two compounds were obtained by reacting 3-[2-(2-oxocyclooentyl)-3-oxo-2,3-dihydropyridazin-6-yl]-2-phenylpyrazolo[1,5-a]pyridine with triethylphosphonoacetate according to a similar manner to that of Example 7.

(1) 3-[2-(2-Ethoxycarbonylmethyl-1-cyclopentenyl)-3-oxo-2,3-dihydropyridazin-6-yl]-2-phenylpyrazolo[1,5-a]-pyridine NMR (CDCl$_3$, δ): 1.195 (3H, t, J=7.1 Hz), 2.047–2.300 (2H, m), 2.400–3.000 (4H, m), 3.000–3.157 (2H, m), 4.056 (2H, q, J=7.20 Hz), 6.722 (1H, d, J=9.67 Hz), 6.751–7.034 (1H, m), 7.009 (1H, d, J=9.67 Hz), 7.265–7.316 (1H, m), 7.443–7.655 (3H, m), 7.955–8.018 (2H, m), 7.996 (1H, d, J=8.95 Hz), 8.524 (1H, d, J=6.96 Hz); (+)-APCI MS: 441 (M$^+$+1);

(2) 3-[2-(2-Ethoxycarbonylmethylenecyclopentyl)-3-oxo-2,3-dihydropyridazin-6-yl]-2-phenylpyrazolo[1,5-a]-pyridine (E or Z isomer)

NMR (CDCl$_3$, δ): 1.261 (3H, t, J=7.1 Hz), 2.000–2.400 (4H, m), 2.800–3.250 (2H, m), 4.176 (2H, q, J=7.15 Hz), 5.615–5.651 (1H, m), 6.096 (1H, m), 6.784 (1H, d, J=9.66 Hz), 6.899 (1H, t, J=6.87 Hz), 7.010 (1H, d, J=9.66 Hz), 7.198–7.283 (1H, m), 7.447–7.493 (3H, m), 7.586–7.635 (2 Hz, m), 7.836 (1H, d, J=8.92 Hz), 8.509 (1H, d, J=6.94 Hz); (+)-APCI MS: 441 (M$^+$+1).

EXAMPLE 13

A mixture of cis-3-[2-(4-methoxycarbonyl-2-oxocyclohexyl)-3-oxo-2,3-dihydropyridazin-6-yl]-2-phenylpyrazolo[1,5-a]pyridine (80 mg) and 1N aqueous sodium hydroxide (2 ml) in methanol (4 ml) was heated at 50° C. for 4 hours. The solution was acidified with 1N aqueous hydrochloric acid and the mixture was extracted with ethyl acetate. The organic layer was washed with brine, dried over magnesium sulfate, and evaporated in vacuo. The residue was triturated with diethyl ether to give cis-3-[2-(4-carboxy-2-oxocyclohexyl)-3-oxo-2,3-dihydropyridazin-6-yl]-2-phenylpyrazolo[1,5-a]pyridine (57 mg).

mp: 186–188° C.; IR (Nujol): 1725, 1700, 1640, 1570 cm$^{-1}$; (+)-APCI/MS: 429 (M$^+$+1); Analysis Calcd. for C$_{24}$H$_{20}$N$_4$O$_4$.3/4H$_2$O: C, 65.22, H, 4.90, N, 12.67; Found: C, 65.33, H, 4.99, N, 12.35.

The following compounds (Examples 14 and 15) were obtained according to a similar manner to that of Example 13.

EXAMPLE 14

3-[2-(2-Carboxymethyl-1-cyclopentenyl)-3-oxo-2,3-dihydropyridazin-6-yl]-2-phenylpyrazolo[1,5-a]pyridine IR (Nujol): 1730, 1700, 1650, 1635, 1570 cm$^{-1}$; NMR (DMSO-d$_6$, δ): 1.80–2.20 (2H, m), 2.30–2.80 (4H, m), 2.88 (2H, s), 6.864 (1H, d, J=9.67 Hz), 6.975 (1H, d, J=9.67 Hz), 7.000–7.200 (1H, m), 7.300–7.615 (6H, m), 7.954 (1H, d, J=8.93 Hz), 8.789 (1H, d, J=6.93 Hz); (+)-APCI MS: 413 (M$^+$+1).

EXAMPLE 15

3-[2-(2-Carboxymethylenecyclopentyl)-3-oxo-2,3-dihydropyridazin-6-yl]-2-phenylpyrazolo[1,5-a]pyridine (E or Z isomer)

IR (Nujol): 1710, 1630, 1565, 1525 cm$^{-1}$; NMR (DMSO-d$_6$, δ): 1.900–2.500 (4H, m), 2.794 and 3.063 (2H, ABq, J=16.3 Hz), 5.944 (1H, br s), 6.106 (1H, m), 6.746 (1H, d, J=9.66 Hz), 7.035–7.116 (1H, m), 7.059 (1H, d, J=9.66 Hz), 7.371–7.626 (6H, m), 7.870 (1H, d, J=8.88 Hz), 8.808 (1H, d, J=6.92 Hz), 12.140 (1H, s); (+)-APCI MS: 413 (M$^+$+1).

EXAMPLE 16 cis-3-[2-(5-Ethoxycarbonyl-2-oxocyclohexyl)-3-oxo-2,3-dihydropyridazin-6-yl]-2-phenylpyrazolo[1,5-a]pyridine was obtained according to a similar manner to that of Example 2.

mp: 160–162° C. (Et$_2$O) IR (Nujol): 1720, 1660, 1590, 1520 cm$^{-1}$; NMR (CDCl$_3$, δ): 1.29 (3H, t, J=7.14 Hz), 2.99 (1H, ddd, J=5.50 Hz, 12.85 Hz, 18.30 Hz), 2.35–2.85 (4H, m), 3.0–3.20 (1H, m), 5.86 (1H, t, J=8.50 Hz), 6.78 (1H, d, J=9.70 Hz), 6.90 (1H, dt, J=1.3 Hz, 6.90 Hz), 7.15 (1H, d, J=9.70 Hz), 2.22–7.33 (1H, m), 7.42–7.49 (3H, m), 7.60–7.66 (2H, m), 7.87 (1H, d, J=8.92 Hz), 8.51 (1H, d, J=6.90 Hz); (+)-APCI/MS: 457 (M$^+$+1); Analysis Calcd. for C$_{26}$H$_{24}$N$_4$O$_4$: C, 68.41, H, 5.30, N, 12.27; Found C, 68.65, H, 5.36, N, 12.16.

EXAMPLE 17 cis-3-[2-(5-Carboxy-2-oxocyclohexyl)-3-oxo-2,3-dihydropyridazin-6-yl]-2-phenylpyrazolo[1,5-a]pyridine was obtained according to a similar manner to that of Example 13.

mp: 155–165° C. (H$_2$O); IR (Nujol): 1720, 1660, 1590, 1530 cm$^{-1}$; NMR (DMSO-d$_6$, δ): 1.60–1.90 (1H, m), 2.20–2.60 (4H, m), 2.70–2.90 (1H, m), 3.10–3.30 (1H, m), 5.70–5.90 (1H, m), 6.92 (1H, d, J=6.70 Hz), 7.07 (1H, t, J=6.90 Hz), 7.17 (1H, d, J=6.70 Hz), 7.35–7.70 (6H, m), 7.79 (1H, d, J=8.90 Hz), 8.83 (1H, d, J=6.90 Hz), 12.58 (1H, s); (+)-APCI/MS: 429 (M$^+$+1); Analysis Calcd. for C$_{24}$H$_{20}$N$_4$O$_4$. H$_2$O: C, 64.57, H, 4.97, N, 12.55; Found: C, 64.85, H, 4.60, N, 12.55.

EXAMPLE 18

The following two compounds were obtained by reacting 3-[2-(2-oxocycloheptyl)-3-oxo-2,3-dihydropyridazin-6-yl]-2-phenylpyrazolo[1,5-a]pyridine with t-butyl 2-(diethoxyphosphoryl)acetate according to a similar manner to that of Example 7.

(1) 3-[2-(2-t-Butoxycarbonylmethyl)-1-cycloheptenyl)-3-oxo-2,3-dihydropyridazin-6-yl]-2-phenylpyrazolo[1,5-a]pyridine (oil)

IR (Nujol): 1705, 1650, 1630, 1590, 1520 cm$^{-1}$; NMR (CDCl$_3$, δ): 1.28 (9H, s), 1.27–1.47 (2H, m), 1.60–2.0 (5H, m), 2.35–2.80 (3H, m), 2.90 (2H, s), 6.76 (1H, d, J=9.7 Hz), 6.89 (1H, t, J=6.7 Hz), 7.00 (1H, d, J=9.7 Hz), 7.14–7.34 (2H, m), 7.44–7.50 (3H, m), 7.60–7.64 (2H, m), 8.03 (1H, d, J=7.9 Hz), 8.50 (1H, d, J=6.0 Hz); (+)-APCI/MS: 497 (M$^+$+1); Analysis Calcd. for C$_{29}$H$_{32}$N$_4$O$_3$.1/2H$_2$O.0.7 toluene: C, 72.96, H, 6.97, N, 10.04; Found: C, 72.85, H, 6.78, N, 9.58.

(2) 3-[2-(2-t-Butoxycarbonylmethylenecycloheptyl)-3-oxo-2,3-dihydropyridazin-6-yl]-2-phenylpyrazolo[1,5-a]pyridine (oil)

IR (Nujol): 1700, 1650, 1585, 1520 cm$^{-1}$; NMR (CDCl$_3$, δ): 1.03–1.63 (3H, m), 1.47 (9H, s), 1.70–2.36 (5H, m), 2.67 (1H, t, J=10.0 Hz), 3.31–3.42 (1H, m), 5.71 (1H, s), 5.76 (1H, dd, J=5.6 Hz, 10.2 Hz), 6.77 (1H, d, J=9.6 Hz), 6.90 (1H, t, J=5.7 Hz), 7.00 (1H, d, J=9.6 Hz), 7.10–7.32 (2H, m), 7.19–7.32 (3H, m), 7.58–7.64 (2H, m), 7.86 (1H, d, J=9.0 Hz), 8.52 (1H, d, J=7.0 Hz); (+)-APCI/MS: 497 (M$^+$+1); Analysis Calcd. for C$_{29}$H$_{32}$N$_4$O$_3$.H$_2$O.1/2 toluene: C, 71.88, H, 6.98, N, 10.21; Found: C, 72.24, H, 6.84, N, 10.51.

EXAMPLE 19

To a solution of 3-[2-(2-t-butoxycarbonylmethyl-1-cycloheptenyl)-3-oxo-2,3-dihydropyridazin-6-yl]-2-phenylpyrazolo[1,5-a]pyridine (0.15 g) in dry dichloromethane (0.5 ml) at room temperature was added trifluoroacetic acid (0.46 ml). After stirring for one day at room temperature, the solution was partitioned between ethyl acetate and a saturated aqueous sodium bicarbonate. The separated aqueous layer was acidified with 1N-hydrochloric acid to pH 3 and extracted with ethyl acetate. The separated organic layer was washed with brine, dried over magnesium sulfate, and evaporated in vacuo. The residue was recrystallized from ethanol—water to give 3-[2-(2-carboxymethyl-1-cycloheptenyl)-3-oxo-2,3-dihydropyridazin-6-yl]-2-phenylpyrazolo[1,5-a]-pyridine (0.083 g).

mp: 171–172° C. (EtOH-H$_2$O); IR (Nujol): 1720, 1640, 1570, 1520 cm$^{-1}$; NMR (DMSO-d$_6$, δ): 1.40–1.85 (6H, m), 2.25–2.50 (4H, m), 2.85 (2H, s), 6.89 (1H, d, J=9.7 Hz), 7.00–7.11 (2H, m), 7.30–7.70 (6H, m), 7.88 (1H, d, J=8.6 Hz), 8.80 (1H, d, J=6.9 Hz); (+)-APCI/MS: 441 (M$^+$+1); Analysis Calcd. for C$_{25}$H$_{24}$N$_4$O$_3$: C, 70.89, H, 5.49, N, 12.72; Found: C, 70.84, H, 5.42, N, 12.62.

The following compounds (Examples 20 to 30) were obtained according to a similar manner to that of Example 2.

EXAMPLE 20

3-[2-(4-Ethoxycarbonylcyclohexyl)-3-oxo-2,3-dihydropyridazin-6-yl]-2-phenylpyrazolo[5-a]pyridine (cis and trans mixture).

mp: 156–160° C. (EtOAc-IPE); IR (Nujol): 1718, 1650, 1625, 1580, 1525 cm$^{-1}$; NMR (CDCl$_3$, δ): (cis and trans mixture) 1.22 (3H, m), 1.64–2.74 (9H, m), 4.11–4.24 (2H, m), 5.03–5.14 (1H, m), 6.70–6.79 (1H, m), 6.89–7.03 (2H, m), 7.29–7.37 (1H, m), 7.43–7.47 (3H, m), 7.58–7.63 (2H, m), 7.92 and 8.08 (2H ratio 1.59:1, d, J=8.9 Hz), 8.50–8.55 (1H, m); Analysis Calcd. for C$_{26}$H$_{26}$N$_4$O$_3$: C, 70.57, H, 5.92, N, 12.66; Found: C, 70.46, H, 5.97, N, 12.47.

EXAMPLE 21

3-[2-(4,4-Ethylenedioxycyclohexyl)-3-oxo-2,3-dihydropyridazin-6-yl]-2-phenylpyrazolo[1,5-a]pyridine mp: 189–190° C. (EtOAc-EtOH); IR (Nujol): 1650, 1580 cm$^{-1}$; NMR (CDCl$_3$, δ): 1.54–1.91 (5H, m), 2.05–2.18 (3H, m), 3.93–4.07 (4H, m), 5.28–5.38 (1H, m), 6.76 (1H, d, J=9.6 Hz), 6.92 (1H, t, J=7.0 Hz), 6.99 (1H, d, J=9.6 Hz), 7.33 (1H, t, J=8.0 Hz), 7.43–7.48 (3H, m), 7.58–7.63 (2H, m), 7.92 (1H, d, j=8.0 Hz), 8.53 (1H, d, J=7.0 Hz); Analysis Calcd. for C$_{25}$H$_{24}$N$_4$O$_3$: C, 70.08, H, 5.65, N, 13.08; Found: C, 69.89, H, 5.50, N, 12.98; (+)-APCI/MS: 429 (M$^+$+1).

EXAMPLE 22 trans-3-[2-(3-Methoxycarbonylcyclohexyl)-3-oxo-2,3-dihydropyrdazin-6-yl]-2-phenylpyrazolo[1,5-a]-pyridine IR (CH$_2$Cl$_2$): 1725, 1660, 1590, 1530 cm$^{-1}$; NMR (CDCl$_3$, δ): 1.26–2.22 (7H, m), 2.36 (1H, dm, J=13.0 Hz), 2.99 (1H, t, J=Ca.4 Hz), 3.76 (3H, s), 5.10–5.30 (1H, m), 6.76 (1H, d, J=9.6 Hz), 6.91 (1H, td, J=7.0 Hz, 1.4 Hz), 7.01 (1H, d, J=9.6 Hz), 7.31 (1H, dd, J=8.9 Hz, 7.0 Hz), 7.43–7.46 (3H, m), 7.58–7.63 (2H, m), 7.90 (1H, d, J=8.9 Hz), 8.53 (1H, d, J=7.0 Hz); (+)-APCI/MS: 429 (M$^+$+1); Analysis Calcd. for C$_{25}$H$_{24}$N$_4$O$_3$.1/2H$_2$O: C, 68.63, H, 5.75, N, 12.82; Found: C, 68.77, H, 6.02, N, 12.10.

EXAMPLE 23

3-[2-(2-Oxopyrrolidin-3-yl)-3-oxo-2,3-dihydropyridazin-6-yl]-2-phenylpyrazolo[1,5-a]pyridine mp: 133–134° C. (dec.) (Et$_2$O); IR (Nujol): 1720, 1710, 1665, 1655, 1630, 1570, 1520 cm$^{-1}$; NMR (DMSO-d$_6$, δ): 2.10–2.40 (2H, m), 5.67 (1H, t, J=9.0 Hz), 6.91 (1H, d, J=9.7 Hz), 7.06–7.10 (2H, m), 7.41 (1H, dd, J=8.9, 7.0 Hz), 7.37–7.51 (3H, m), 7.59–7.62 (2H, m), 7.93 (1H, d, J=8.9 Hz), 8.20 (1H, s), 8.83 (1H, d, J=7.0 Hz); (+)-APCI/MS: 372 (M$^+$+1).

EXAMPLE 24

3-[2-(2,6-Dioxocyclohexyl)-3-oxo-2,3-dihydropyridazin-6-yl]-2-phenylpyrazolo[1,5-a]pyridine IR (Nujol): 1670, 1650, 1630, 1600, 1560 cm$^{-1}$; NMR (CDCl$_3$, δ): 2.00–2.80 (6H, m), 5.30 (1H, s), 6.86 (1H, d, J=9.7 Hz), 6.84–6.89 (1H, m), 7.11 (1H, d, J=9.7 Hz), 7.27–7.37 (1H, m), 7.45–7.62 (3H, m), 7.62–7.67 (2H, m), 8.16 (1H, d, J=8.9 Hz), 8.51 (1H, d, J=6.9 Hz); (+)-APCI/MS: 399 (M$^+$+1).

EXAMPLE 25

3-[2-(2-Oxo-2,3,4,5-tetrahydrofuran-3-yl)-3-oxo-2,3-dihydropyridazin-6-yl]-2-phenylpyrazolo[1,5-a]pyridine mp: 179–180° C. (Et$_2$O); IR (Nujol): 1780, 1665, 1625, 1585, 1530 cm$^{-1}$; NMR (DMSO-d$_6$, δ): 2.50–2.90 (2H, m), 4.35–4.55 (2H, m), 5.95 (1H, t, J=9.5 Hz), 6.97 (1H, d, J=9.7 Hz), 7.05–7.16 (2H, m), 7.41–7.53 (4H, m), 7.58–7.64 (2H, m), 7.88 (1H, d, J=8.9 Hz), 8.84 (1H, d, J=6.9 Hz); (+)-APCI/MS: 373 (M$^+$+1).

EXAMPLE 26

3-[2-(2-Oxopiperidin-3-yl)-3-oxo-2,3-dihydropyridazin-6-yl]-2-phenylpyrazolo[1,5-a]pyridine mp: 140–145° C. (dec.) (Et$_2$O); IR (Nujol): 1670, 1660, 1655, 1630, 1580, 1570, 1530 cm$^{-1}$; NMR (DMSO-d$_6$, δ): 1.89–1.99 (2H, m), 2.08–2.25 (2H, m), 3.21 (2H, m), 5.41 (1H, t, J=8.3 Hz), 6.90 (1H, d, J=9.7 Hz), 7.04–7.12 (2H, m), 7.37–7.53 (4H, m), 7.58–7.63 (2H, m), 7.90 (1H, d, J=9.0 Hz), 8.82 (1H, d, J=6.9 Hz); (+)-APCI/MS: 386 (M$^+$+1).

EXAMPLE 27

3-[2-(1,3-Dipropyl-2,4-dioxo-1,2,3,4-tetrahydropyrimidin-6-yl)-3-oxo-2,3-dihydropyridazin-6-yl]-2-phenylpyrazolo[1,5-a]pyridine mp: 155.3° C. (Et$_2$O); IR (Nujol): 1705, 1665, 1630, 1600, 1525 cm$^{-1}$; NMR (CDCl$_3$, δ): 0.85 (3H, t, J=7.4 Hz), 1.01 (3H, t, J=7.4 Hz), 1.60–1.83 (4H, m), 3.53 (1H, quintet, J=7.4 Hz), 3.81–4.01 (3H, m), 5.93 (1H, s), 6.83 (1H, d, J=9.9 Hz), 6.99 (1H, t, J=6.9 Hz), 7.14 (1H, d, J=9.9 Hz), 7.39 (1H, t, J=6.9 Hz), 7.49–7.59 (5H, m), 7.93 (1H, d, J=8.9 Hz), 8.56 (1H, d, J=6.9 Hz); (+)-APCI/MS: 483 (M$^+$+1); Analysis Calcd. for $C_{27}H_{26}N_6O_3$: C, 66.20, H, 5.43, N, 17.42; Found: C, 66.73, H, 5.31, N, 17.26.

EXAMPLE 28

3-[2-(2,4-Dioxo-1-methoxycarbonylmethyl-3-propyl-1,2,3,4-tetrahydropyrimidin-6-yl)-3-oxo-2,3-dihydropyridazin-6-yl]-2-phenylpyrazolo[1,5-a]pyridine mp: 143–145° C. (Et$_2$O); IR (Nujol): 1720,. 1700, 1680, 1660, 1590, 1520 cm$^{-1}$; NMR (CDCl$_3$, δ): 1.00 (3H, t, J=7.5 Hz), 1.75 (2H, hept, J=7.5 Hz), 3.55 (3H, s), 3.98 (2H, t, J=7.5 Hz), 6.02 (1H, s), 6.78 (1H, d, J=9.9 Hz), 6.98 (1H, dt, J=1.3, 6.9 Hz), 7.13 (1H, d, J=9.9 Hz), 7.36–7.44 (1H, m), 7.49–7.64 (5H, m), 8.05 (1H, d, J=8.9 Hz), 8.54 (1H, d, J=6.9 Hz); Analysis Calcd. for $C_{27}H_{24}N_6O_5$: C, 63.27, H, 4.72, N, 16.40; Found: C, 62.99, H, 4.58, N, 16.20; (+)-APCI/MS: 513 (M$^+$+1).

EXAMPLE 29

3-[2-(2,4-Dioxo-3-methoxycarbonylmethyl-1-propyl-1,2,3,4-tetrahydropyrimidin-6-yl)-3-oxo-2,3-dihydropyridazin-6-yl]-2-phenylpyrazolo[1,5-a]pyridine.

mp: 191–195° C. (AcOEt-hexane); IR (Nujol): 1750, 1710, 1670, 1600, 1520 cm$^{-1}$; NMR (CDCl$_3$, δ): 0.84 (3H, t, J=7.5 Hz), 1.57–1.80 (2H, m), 3.40–3.69 (1H, m), 3.81 (3H, s), 3.70–4.03 (1H, m), 4.73 (1H, d, J=14.0 Hz), 4.83 (1H, d, J=14.0 Hz), 5.99 (1H, s), 6.82 (1H, d, J=9.9 Hz), 7.00 (1H, dt, J=1.4, 6.9 Hz), 7.15 (1H, d, J=9.9 Hz), 7.42 (1H, dt, J=1.0, 6.9 Hz), 7.49–7.63 (5H, m), 7.98 (1H, d, J=8.9 Hz), 8.57 (1H, d, J=6.9 Hz); (+)-APCI/MS: 513 (M$^+$+1); Analysis Calcd. for $C_{27}H_{24}N_6O_5$: C, 63.27, H, 4.72, N, 16.40; Found: C, 62.98, H, 4.66, N, 15.96.

EXAMPLE 30 trans-3-[2-(6-Hydroxy-2-methoxy-5,6,7,8-tetrahydro-5-naphthyl)-3-oxo-2,3-dihydropyridazin-6-yl]-2-phenylpyrazolo[1,5-a]pyridine mp: 146–150° C. (EtOH); IR (Nujol): 1645, 1575 cm$^{-1}$; NMR (CDCl$_3$, δ): 1.98–2.11 (2H, m), 2.23–2.31 (1H, m), 2.93–2.99 (2H, m), 3.48 (1H, d, J=4.5 Hz), 3.83 (3H, s), 4.31–4.47 (1H, m), 6.31 (1H, d, J=6.9 Hz), 6.72–7.01 (7H, m), 7.43–7.60 (5H, m), 8.41 (1H, d, J=6.7 Hz); (+)-APCI/MS: 465 (M$^+$+1).

EXAMPLE 31

To a solution of 3-(3-oxo-2,3-dihydropyridazin-6-yl)-2-phenylpyrazolo[1,5-a]pyridine (271 mg) in N,N-dimethylformamide (6 ml) was added potassium tert-butoxide (111 mg) and 18-crown-6 (24.8 mg) at 5° C. To this solution was added a solution of (E)-1-methylsulfonyloxy-2-methoxycarbonylmethylenecyclohexane (467 mg) in N,N-dimethylformamide (2 ml) was added dropwise. The reaction mixture was stirred at room temperature for 1 hour and then heated at 110 to 125° C. for 7 hours. The reaction mixture was poured into ice water (30 ml) and extracted with ethyl acetate (20 ml×2). The combined extracts were washed with water (20 ml) and brine (20 ml), dried over anhydrous magnesium sulfate, and evaporated in vacuo. The crude material was purified by column chromatography on SiO$_2$ using a mixture of dichloromethane and ethyl acetate (20:1) as an eluant to give colorless crystals of (E)-3-[2-(2-methoxycarbonylmethylenecyclohexyl)-3-oxo-2,3-dihydropyridazin-6-yl]-2-phenylpyrazolo[1,5-a]pyridine (191.4 mg).

mp: 156–157° C. (EtOAc); IR (Nujol): 1700, 1670, 1640, 1595, 1520 cm$^{-1}$; NMR (CDCl$_3$, δ): 1.40–2.43 (7H, m), 3.64 (3H, s), 4.10 (1H, brd d, J=12.9 Hz), 5.14 (1H, s), 5.65 (1H, ddp J=11.9, 3.3 Hz), 6.81 (1H, d, J=9.7 Hz), 6.91 (1H, td, J=6.9, 1.0 Hz), 7.05 (1H, d, J=9.7 Hz), 7.29 (1H, dd, J=9.0, 6.9 Hz), 7.45–7.48 (3H, m), 7.60–7.64 (2H, m), 7.91 (1H, d, J=9.0 Hz), 8.53 (1H, d, J=6.9 Hz); Analysis Calcd. for $C_{26}H_{24}N_4O_3$: C, 70.89, H, 5.49, N, 12.72; Found: C, 70.54, H, 5.52, N, 12.67.

EXAMPLE 32

The following compound was obtained according to a similar manner c that of Example 31.

trans-3-[2-(3-Methoxycarbonylmethylcyclopentyl)-3-oxo-2,3-dihydropyridazin-6-yl]-2-phenylpyrazolo[1,5-a]pyridine mp: 105–107° C. (IPE-EtOAc); IR (Nujol): 1730, 1655, 1630, 1590, 1525 cm$^{-1}$; NMR (CDCl$_3$, δ): 1.30–1.46 (1H, m), 1.74–2.52 (7H, m), 2.63–2.81 (1H, m), 3.69 (3H, s), 5.60–5.73 (1H, m), 6.7.3 (1H, d, J=9.6 Hz), 6.92 (1H, td, J=7.0 Hz, 1.3 Hz), 7.00 (1H, d, J=9.6 Hz), 7.37 (1H, ddd, J=9.0, 7.0, 1.0 Hz), 7.43–7.48 (3H, m), 7.58–7.63 (2H, m), 8.01 (1H, d, J=9.0 Hz), 8.53 (1H, d, J=7.0 Hz); (+)-APCI/MS: 429 (M$^+$+1); Analysis Calcd. for $C_{25}H_{24}N_4O_3$: C, 70.08, H, 5.65, N, 13.08; Found: C, 69.67, H, 5.48, N, 12.99.

EXAMPLE 33

To a suspension of 3-(3-oxo-2,3-dihydropyridazin-6-yl)-2-phenylpyrazolo[1,5-a]pyridine (1.23 g) in N,N-dimethylformamide (30 ml) was added potassium tert-butoxide (502 mg) at 5° C. After 5 minutes, to this was added 18-crown-6 (113 mg) and a solution of trans-2-(2-methylsulfonyloxycyclohexyl)acetic acid ethyl ester (2.25 g) in N,N-dimethyl formamide (10 ml). The reaction mixture was warmed up to room temperature and then heated at 110°–130° C. for 6 hours and 45 minutes with stirring. The reaction mixture was poured into ice-water (200 ml). and extracted with ethyl acetate (50 ml). After an additional extraction with ethyl acetate (50 ml), the combined extracts were washed with water (50 ml) and brine (50 ml), dried over anhydrous magnesium sulfate, and evaporated in vacuo. The crude material, which was cis and trans mixture, was separated by silica gel column chromatography sing a mixture of toluene and ethyl acetate (10:1–10:2) as an eluant.

(1) The less polar isomer (trans isomer):

trans-3-[2-(2-Ethoxycarbonylmethylcyclohexyl)-3-oxo-2,3-dihydropyridazin-6-yl]-2-phenylpyrazolo[1,5-a]pyridine (58.4 mg) (colorless crystals)

mp: 172–173° C. (EtOAc); IR (Nujol): 1720, 1650, 1625, 1580, 1520 cm$^{-1}$; NMR (CDCl$_3$, δ): 1.18 (3H, t, J=7.1 Hz), 1.32–2.35 (10H, m), 2.47–2.70 (1H, m), 3.98–4.10 (2H, m), 4.91 (1H, td, J=10.0, 4.1 Hz), 6.72 (1H, d, J=9.7 Hz), 6.92 (1H, td, J=6.9, 1.4 Hz), 6.95 (1H, d, J=9.7 Hz), 7.36 (1H, dd, J=8.9, 6.9 Hz), 7.43–7.47 (3H, m), 7.60–7.65 (2H, m), 8.08 (1H, d, J=8.9 Hz), 8.53 (1H, d, J=6.9 Hz); Analysis Calcd. for $C_{27}H_{28}N_4O_3.0.2H_2O$: C, 70.47, H, 6.16, N, 12.18; Found: C, 70.36, H, 6.07, N, 11.93.

(2) The more polar compound (cis isomer):

cis-3-[2-(2-Ethoxycarbonylmethylcyclohexyl)-3-oxo-2,3-dihydropyridazin-6-yl]-2-phenylpyrazolo[1,5-a]pyridine (130 mg) (colorless crystals)

mp: 151–152° C. (EtOAc-IPE); IR (Nujol): 1715, 1640, 1625, 1590, 1525 cm$^{-1}$; NMR (CDCl$_3$, δ): 1.10 (3H, t, J=7.1 Hz), 1.41–2.55 (10 H, m), 2.95–3.03 (1H, m), 3.83–4.13 (2H, m), 5.15 (1H, dt, J=12.0, 4.0 Hz), 6.75 (1H, d, J=9.6

Hz), 6.91 (1H, td, J=6.9, 1.3 Hz), 7.00 (1H, d, J=9.6 Hz), 7.32 (1H, ddd, J=9.0, 6.9, 1.3 Hz), 7.43–7.48 (3H, m), 7.57–7.62 (2H, m), 7.94 (1H, d, J=9.0 Hz), 8.53 (1H, d, J=6.9 Hz); Analysis Calcd. for $C_{27}H_{28}N_4O_3 \cdot 0.2H_2O$: C, 70.47, H, 6.16, N, 12.18; Found: C, 70.36, H, 6.22, N, 12.07.

EXAMPLE 34

A solution of 3-(3-oxo-2,3-dihydropyridazin-6-yl)-2-phenylpyrazolo[1,5-a]pyridine (870 mg), 1-(tert-butyldimethylsilyl)oxy-3-iodocyclohexane (1.5 g), potassium tert-butoxide (472 mg) and 18-crown-6 (80mg) in N,N-dimethylformamide (10 ml) was stirred for 2 hours at room temperature. A reaction mixture was diluted with a mixture of ethyl acetate (150 ml) and n-hexane (50 ml), which was washed in turn with water (50-ml), 1N-aqueous sodium hydroxide solution (50 ml×3) and saturated sodium chloride in water (50 ml×2), and dried over magnesium sulfate. Evaporation of the solvent gave a residue, which was chromatographed on silica gel (80 ml) eluting in-turn with 25%, 33% and 50% ethyl acetate in dichloromethane to give 3-[2-{3-(tert-butyldimethylsilyloxy)cyclohexyl}-3-oxo-2,3-dihydropyridazin-6-yl]-2-phenylpyrazolo[1,5-a]-pyridine (0.23 g).

FT IR (KBr): 1664.3, 1591.0, 1531.2 cm$^{-1}$; NMR (CDCl$_3$, δ): 0.09 (6H, s), 0.90 (9H, s), 1.20–2.30 (8H, m), 3.70–3.90 (1H, m), 4.95–5.20 (1H, m), 6.76 (1H, d, J=9.6 Hz), 6.80–7.00 (1H, m), 7.00 (1H, d, J=9.6 Hz), 7.28–7.40 (1H, m), 7.40–7.70 (5H, m), 7.98 (1H, d, J=9.0 Hz), 8.54 (1H, d, J=6.9 Hz); (+)-APCI/MS: 501 (M$^+$+1).

EXAMPLE 35

A mixture of 3-(3-oxo-2,3-dihydropyridazin-6-yl)-2-phenylpyrazolo[1,5-a]pyridine (2.25 g), 1-methyl-1,2-epoxycyclohexane (1.31 g), benzyltrimethylammonium chloride (178 mg), 1N aqueous sodium hydroxide (7.8 ml), water (17 ml), and toluene was heated to reflux for 8 hours and 20 minutes. After the reaction mixture was cooled to room temperature, the precipitates were collected by filtration, washed with water, and dried. The crude material was purified by column chromatography on silica gel (CH$_2$Cl$_2$:EtOAc=10:2) to give colorless crystals of 3-[2-{(1R*,2R*)-2-hydroxy-2-methylcyclohexyl}-3-oxo-2,3-dihydropyridazin-6-yl]-2-phenylpyrazolo[1,5-a]-pyridine (189 mg).

mp: 197–198° C. (EtOAc); IR (Nujol): 3280, 1640, 1570, 1520 cm$^{-1}$; NMR (CDCl$_3$, δ): 1.24 (3H, s), 1.37–2.38 (8H, m), 2.96 (1H, brd s, OH), 5.13 (1H, dd, J=12.4, 3.5 Hz), 6.82 (1H, d, J=9.6 Hz), 6.93 (1H, t, J=6.9 Hz), 7.04 (1H, d, J=9.6 Hz), 7.33 (1H, dd, J=8.9, 6.9 Hz), 7.45–7.48 (3H, m), 7.56–7.61 (2H, m), 7.95 (1H, d, J=8.9 Hz), 8.56 (1H, d, J=6.9 Hz); Analysis Calcd. for $C_{24}H_{24}N_4O_2$: C, 71.98, H, 6.04, N, 13.99; Found: C, 72.16, H, 6.19, N, 14.17.

EXAMPLE 36

The following compound was obtained according to a similar manner to that of Example 35 from 3-(3-oxo-2,3-dihydropyridazin-6-yl)-2-phenylpyrazolo[1,5-a]pyridine and methyl 2-(2.,3-epoxycyclohexyl)acetate.

3-[2-(2-oxoperhydrobenzo[b]furan-7-yl)-3-oxo-2,3-dihydropyridazin-6-yl]-2-phenylpyrazolo[1,5-a]pyridine IR (Nujol): 1775, 1665, 1635, 1600, 1535 cm$^{-1}$; NMR (CDCl$_3$, δ): 1.62–2.10 (6H, m), 2.45–2.69 (2H, m), 2.83–3.08 (1H, m), 5.00–5.20 (2H, m), 6.81 (1H, d, J=9.6 Hz), 6.92 (1H, t, J=6.9 Hz), 7.05 (1H, d, J=9.6 Hz), 7.32 (1H, dd, J=9.0, 6.9 Hz), 7.44–7.47 (3H, m), 7.59–7.61 (2H, m), 7.84 (1H, d, J=9.0 Hz), 8.83 (1H, d, J=6.9 Hz).

EXAMPLE 37

(1) Sodium hydroxide (1.3 g), 3-(3-oxo-2,3-dihydropyridazin-6-yl)-2-phenylpyrazolo[1,5-a]pyridine (9.34 g) and benzyltriethylammonium chloride (740 mg) was dissolved in a mixture of toluene (100 ml) and water (100 ml), which was added 1-tert-butoxycarbonyl-3,4-epoxypiperidine (11.62 g) and refluxed for 9.5 hours.

To a reaction mixture was added ethyl acetate (500 ml) and organic layer was separated, which was washed in turn with 1N-aqueous sodium hydroxide solution (100 ml×2) and. saturated sodium chloride in water (100 ml×2), and dried over magnesium sulfate. Evaporation of the solvent gave a residue, which was chromatographed on silica gel eluting in turn with 50% dichloromethane in ethyl acetate and ethyl acetate to give the intermediate [a mixture of 3-[2-(1-tert-butoxycarbonyl-4-hydroxypiperidin-3-yl)-3-oxo-2,3-dihydropyridazin-6-yl]-2-phenylpyrazolo[1,5-a] pyridine and 3-[-2-(1-tert-butoxycarbonyl-3-hydroxypiperidin-4-yl)-3-oxo-2,3-dihydropyridazin-6-yl)-2-phenylpyrazolo[1,5-a]-pyridine].

(2) Next oxidation reaction was carried out as follows.

To a solution of oxalyl chloride (2.66 ml) in dichloromethane (100 ml) was added dropwise in turn with dimethyl sulfoxide (4.5 ml), a solution of the intermediate obtained above (9.9 g) in dichloromethane (50 ml) and triethylamine (14.2 ml) at −70° C. under nitrogen atmosphere. A reaction mixture was allowed to warm to room temperature and poured into ethyl acetate (600 ml), which was washed in turn with water (200 ml), 1N-aqueous hydrochloric acid (100 ml×3), brine (100 ml), saturated sodium hydrogen carbonate in water (100 ml) and brine (100 ml), and dried over magnesium sulfate. Evaporation of the solvent gave a residue, which was chromatographed on silica gel (270–400 mesh, 600 ml) eluting with a mixture of dichloromethane, chloroform and ethyl acetate (5:5:1) to give 3-[2-(1-tert-butoxycarbonyl-4-oxopiperidin-3-yl)-3-oxo-2,3-dihydropyridazin-6-yl]-2-phenylpyrazolo[1,5-a]-pyridine (2.18 g) and 3-[2-(1-tert-butoxycarbonyl-3-oxopiperidin-4-yl)-3-oxo-2,3-dihydropyridazin-6-yl]-2-phenylpyrazolo[1,5-a]pyridine (4.58 g).

(a) 3-[2-(1-tert-Butoxycarbonyl-4-oxopiperidin-3-yl)-3-oxo-2,3-dihydropyridazin-6-yl]-2-phenylpyrazolo-[1,5-a]pyridine Rf: 0.2 (CH$_2$Cl$_2$:CHCl$_3$:EtOAc=5:5:1); FT IR (KBr): 1727.9, 1699.0, 1666.2, 1637.3, 1592.9, 1529.3 cm$^{-1}$; NMR (CDCl$_3$, δ): 1.52 (9H, s), 2.60–2.80 (2H, m), 3.18–3.28 (1H, m), 3.60–3.80 (1H, m), 4.35–4.80 (2H, m), 5.55–5.70 (1H, m), 6.81 (1H, d, J=9.7 Hz), 6.88–6.96 (1H, m), 7.06 (1H, d, J=9.7 Hz), 7.26–7.35 (1H, m), 7.40–7.50 (3H, m), 7.60–7.70 (2H, m), 7.83 (1H, d, J=9.0 Hz), 8.55 (1H, d, J=7.0 Hz); (+)-APCI/MS: 486 (M$^+$+1).

(b) 3-[2-(1-tert-Butoxycarbonyl-3-oxopiperidin-4-yl)-3-oxo-2,3-dihydropyridazin-6-yl]-2-phenylpyrazolo-[1,5-a]pyridine Rf: 0.09 (CH$_2$Cl$_2$:CHCl$_3$:EtOAc=5:5:1); FT IR (KBr): 1737.5, 1697.1, 1666.2, 1591.0, 1529.3 cm$^{-1}$; NMR (CDCl$_3$, δ): 1.48 (9H, s), 2.20–2.80 (2H, m), 3.40–3.65 (1H, m), 4.0–4.4 (1H, m), 4.08 (1H, d, J=17.8 Hz), 4.48 (1H, d, J=17.8 Hz), 5.79 (1H, dd, J=6.1, 12.3 Hz), 6.80 (1H, d, J=9.7 Hz), 6.91 (1H, t, J=6.8 Hz), 7.05 (1H, d, J=9.7 Hz), 7.26–7.50 (1H, m), 7.40–7.50 (3H, m), 7.59–7.65 (2H, m), 7.81 (1H, d, J=8.9 Hz), 8.53 (1H, d, J=6.9 Hz); (+)-APCI/MS: 486 (M$^+$+1).

EXAMPLE 38

A mixture of cis-3-[2-(2-ethoxycarbonylmethyl-cyclohexyl)-3-oxo-2,3-dihydropyridazin-6-yl]-2- phenylpyrazolo[1,5-a]pyridine (89.7 mg), 1N aqueous sodium hydroxide (1 ml), and dioxane (4 ml) was stirred at room temperature for 5 hours and at 70° C. for 4 hours. Dioxane was removed in vacuo. The remaining aqueous solution was diluted with water and extracted with ethyl acetate (10 ml). The aqueous layer was acidified with 1N hydrochloric acid and extracted with dichloromethane (10 ml×2). The combined extracts were washed with brine (10 ml), dried over anhydrous magnesium sulfate, and evaporated in vacuo to give colorless crystals of cis-3-[2-(2-carboxymethylcyclohexyl)-3-oxo-2,3-dihydropyridazin-6-yl]-2-phenylpyrazolo[1,5-a]pyridine (71.4 mg).

mp: 252–253° C. (EtOAc); IR (Nujol): 1720, 1630, 1560, 1520 cm$^{-1}$; NMR (CDCl$_3$, δ): 1.36–2.57 (10 H, m), 2.81–3.01 (1H, m), 5.11 (1H, dt, J=11.2 Hz, 4.0 Hz), 6.76 (1H, d, J=9.6 Hz), 6.90 (1H, t, J=7.0 Hz), 6.99 (1H, d, J=9.6 Hz), 7.32 (1H, dd, J=8.9, 7.0 Hz), 7.04–7.44 (3H, m), 7.55–7.57 (2H, m), 7.90 (1H, d, J=8.9 Hz), 8.53 (1H, d, J=7.0 Hz).

The following compounds (Examples 39 to 42) were obtained according to a similar manner to that of Example 38.

EXAMPLE 39 trans-3-[2-(2-Carboxymethylcyclohexyl)-3-oxo-2,3-dihydropyridazin-6-yl]-2-phenylpyrazolo[1,5-a]pyridine mp: 238–240° C. (EtOAc); IR (Nujol): 1720, 1635, 1567, 1530 cm$^{-1}$; NMR (CDCl$_3$, δ): 1.22–2.62 (11H, m), 4.92 (1H, td, J=10 Hz, 4.0 Hz), 6.77 (1H, d, J=9.6 Hz), 6.90 (1H, t, J=6.9 Hz), 6.99 (1H, d, J=9.6 Hz), 7.31 (1H, dd, J=8.9, 6.9 Hz), 7.43–7.46 (3H, m), 7.56–7.59 (2H, m), 8.03 (1H, d, J=8.9 Hz), 8.52 (1H, d, J=6.9 Hz).

EXAMPLE 40 trans-3-[2-(3-Carboxymethylcyclopentyl)-3-oxo-2,3-dihydropyridazin-6-yl]-2-phenylpyrazolo[1,5-a]pyridine mp: 212–213° C. (EtOHc); IR (Nujol): 1723, 1635, 1570, 1520 cm$^{-1}$; NMR (CDCl$_3$, δ): 1.33–1.47 (1H, m), 1.77–2.80 (8H, m), 5.62–5.75 (1H, m), 6.76 (1H, d, J=9.6 Hz), 6.88 (1H, td, J=6.9, 1.3 Hz), 7.00 (1H, d, J=9.6 Hz), 7.31 (1H, dd, J=8.9, 6.9 Hz), 7.43–7.46 (3H, m), 7.56–7.61 (2H, m), 7.97 (1H, d, J=8.9 Hz), 8.52 (1H, d, J=6.9 Hz); (+)-APCI/MS: 415 (M$^+$+1); Analysis Calcd. for C$_{24}$H$_{22}$N$_4$O$_3$: C, 69.55, H, 5.35, N, 13.52; Found: C, 69.32, H, 5.40, N, 13.21.

EXAMPLE 41 trans-3-(2-(3-Carboxycyclohexyl)-3-oxo-2,3-dihydropyridazin-6-yl]-2-phenylpyrazolo[1,5-a]pyridine mp: 218–222° C.; IR (Nujol): 1720, 1660, 1580, 1530 cm$^{-1}$; NMR (DMSO-d$_6$, δ): 1.47–2.07 (8H, m), 2.80–2.90 (1H, m), 4.92–5.06 (1H, m), 6.88 (1H, d, J=9.6 Hz), 7.07 (1H, t, J=6.9 Hz), 7.16 (1H, d, J=9.6 Hz), 7.42–7.49 (4H, m), 7.56–7.59 (2H, m), 7.88 (1H, d, J=8.9 Hz), 8.82 (1H, d, J=6.9 Hz); (+)-APCI/MS: 415 (M$^+$+1); Analysis Calcd. for C$_{24}$H$_{22}$N$_4$O$_3$.1/2H$_2$O: C, 68.07, H, 5.47, N, 13.23; Found: C, 68.29, H, 5.42, N, 13.29.

EXAMPLE 42

3-[2-(1-Carboxymethyl-2-oxo-pyrrolidin-3-yl)-3-oxo-2,3-dihydropyridazin-6-yl]-2-phenylpyrazolo[1,5-a]pyridine mp: 250–251° C. (Et$_2$O); IR (Nujol): 1735, 1730, 1710, 1650, 1570, 1530 cm$^{-1}$; NMR (DMSO-d$_6$, δ): 2.10–2.70 (2H, m), 3.45–3.60 (2H, m), 4.01–4.07 (2H, m), 5.81 (1H, t, J=10.0 Hz), 6.91 (1H, d, J=9.7 Hz), 7.04–7.20 (2H, m), 7.30–7.70 (6H, m), 7.89 (1H, d, J=9.0 Hz), 8.81 (1H, d, J=6.5 Hz); (+)-APCI/MS: 430 (M$^+$+1).

EXAMPLE 43

To a solution of 3-[2-{2-(N-ethoxycarbonylmethyl-N-methylcarbamoyl)methyl-1-cyclohexenyl}-3-oxo-2,3-dihydropyridazin-6-yl]-2-phenylpyrazolo[1,5-a]pyridine (710 mg) in a mixture of dioxane (7 ml) and water (4 ml) was added 1N-aqueous sodium hydroxide solution (3.4 ml), which was stirred for two hours at room temperature. The reaction mixture was poured into ethyl acetate (100 ml) and aqueous layer was collected, which was adjusted to pH 1.5 with 6N-aqueous hydrochloric acid and extracted with ethyl acetate (100 ml×2). Organic layers were combined, washed in turn with water (50 ml×3) and brine (50 mil×2), and dried over magnesium sulfate. Evaporation of the solvent gave a residue, which was chromatographed on silica gel (80 ml) eluting in turn with dichloromethane, 5%, 10%, 15% methanol in dichloromethane. Fractions containing desired product were collected. Evaporation of the solvent gave a residue, which was recrystallized from a mixture of dichloromethane and n-hexane to give 3-[2-{2-(N-carboxymethyl-N-methylcarbamoyl)methyl-1-cyclohexenyl}-3-oxo-2,3-dihydropyridazin-6-yl]-2-phenylpyrazolo[1,5-a]pyridine (300 mg).

mp: 135–138° C.; FT IR (KBr) 1729.8, 1656.6, 1585.2, 1529.3 cm$^{-1}$; NMR (DMSOd$_6$, δ): 1.60–1.85 (4H, m), 2.05–2.40 (4H, m), 2.70–3.00 (5H, m), 3.80–3.90 (2H, m), 6.83–7.12 (3H, m), 7.35–7.65 (6H, m), 7.85–7.96(1H, m), 8.81 (1H, d, J=6.9 Hz); (+)-APCI/MS: 498 (M$^+$+1).

The following compounds (Examples 44 to 49) were obtained according to a similar manner to that of Example 43.

EXAMPLE 44

3-[2-{2-(3-(N-Carboxymethylcarbamoyl)propyl)-1-cyclohexenyl}-3-oxo-2,3-dihydropyridazin-6-yl]-2-phenylpyrazolo[1,5-a]pyridine IR (Film) 3350, 1720, 1640, 1580, 1520 cm$^{-1}$; NMR (CDCl$_3$, δ): 1.50–2.60 (14H, m), 4.01 (2H, d, J=4.7 Hz), 6.90 (1H, d, J=9.6 Hz), 6.92 (1H, t, J=6.7 Hz), 7.09 (1H, t, J=4.7 Hz), 7.11 (1H, d, J=9.6 Hz), 7.33 (1H, t, J=6.7 Hz), 7.44–7.50 (3H, m), 7.57–7.62 (2H, m), 7.89 (1H, d, J=9.0 Hz), 8.55 (1H, d, J=6.9 Hz); (+)-APCI/MS: 512 (M$^+$+1).

EXAMPLE 45

3-(2-{2-(N-(2-Carboxyethyl)-N-methylcarbamoyl)methyl-1-cyclohexenyl}-3-oxo-2,3-dihydropyridazin-6-yl]-2-phenylpyrazolo[1,5-a]pyridine mp: 38.8–140.0° C. (CH$_2$Cl$_2$—n-hexane); FT IR (KBr): 1720.2, 1660.4, 1633.4, 1587.1, 1529.3 cm$^{-1}$; NMR (DMSC-d$_6$, δ): 1.60–1.85 (4H, m), 2.05–2.40 (6H, m), 2.60–3.20 (7H, m), 6.82–6.91 (1H, m), 7.00–7.11 (2H, m), 7.40–7.65 (6H, m), 7.85–7.95 (1H, m), 8.80 (1H, d, J=6.8 Hz); (+)-APCI/MS: 512 (M$^+$+1); Analysis Calcd. for C$_{29}$H$_{29}$N$_5$O$_4$.2H$_2$O : C, 63.61, H, 6.07, N, 12.79; Found: C, 63.75, H, 5.83, N, 12.47.

EXAMPLE 46

3-[2-(2-(N-(3-Carboxypropyl)carbamoyl)methyl-1-cyclohexenyl)-3-oxo-2,3-dihydropyridazin-6-yl]-2-phenylpyrazolo[1,5-a]pyridine mp: 92.5–93.0° C.; FT IR (KBr): 1726.0, 1658.5, 1585.2, 1529.3 cm$^{-1}$; NMR (DMSO-d$_6$, δ): 1.43–1.85 (6H, m), 2.09–2.35 (6H, m), 2.65–3.10 (4H, m), 6.95 (1H, d, J=9.7 Hz), 7.04–7.11 (1H, m), 7.15 (1H, d, J=9.7 Hz), 7.35–7.70 (7H, m), 7.91 (1H, d, J=8.8 Hz), 8.82 (1H, d, J=6.8 Hz); (+)-APCI/MS: 512 (M$^+$+1).

EXAMPLE 47

(1) cis-3-[2-(4-Carboxycyclohexyl)-3-oxo-2,3-dihydropyridazin-6-yl]-2-phenylpyrazolo[1,5-a]pyridine mp: 296–298° C. (EtOH); IR (Nujol): 1710, 1645, 1575 cm$^{-1}$; NMR (DMSO-d$_6$, δ): 1.58–2.02 (6H, m), 2.15 (2H, d, J=11.5 Hz), 2.65 (1H, brd s), 4.88 (1H, m), 6.84 (1H, d, J=9.6 Hz), 7.04 (1H, d, J=9.6 Hz), 7.09 (1H, :, J=8.0 Hz), 7.42–7.89 (6H, m), 7.91 (1H, d, J=8.0 Hz), 8.83 (1H, d, J=7.0 Hz); (+)-APCI/MS: 415 (M$^+$+1); Analysis Calcd. for C$_{24}$H$_{22}$N$_4$O$_3$: C, 69.55, H, 5.35, N, 13.52; Found: C, 69.04, H, 5.14, N, 13.38.

(2) trans-3-[2-(4-Carboxycyclohexyl)-3-oxo-2,3-dihydropyrdazin-6-yl]-2-phenylpyrazolo[1,5-a]pyridine mp: 193–395° C. (EtOH); IR (Nujol): 1700, 1660, 1590, 1530 cm$^{-1}$; NMR (DMSO-d$_6$, δ): 1.20–2.05 (8H, m), 2.22 (1H, t, J=10.5 Hz), 4.80 (1H, m), 6.88 (1H, d, J=9.6 Hz), 7.09 (1H, d, J=6.9 Hz), 7.14 (1H, d, J=9.6 Hz), 7.43–7.59 (6H, m), 7.90 (1H, d, J=8.9 Hz), 8.83 (1H, d, J=6.9 Hz); (+)-APCI/MS: 415 (M$^+$+1); Analysis Calcd. for C$_{24}$H$_{22}$N$_4$O$_3$: C, 69.55, H, 5.35, N, 13.52; Found: C, 69.48, H, 5.25, N, 13.65.

EXAMPLE 48

3-[2-(3-Carboxymethyl-2,4-dioxo-1-propyl-1,2,3,4-tetrahydropyrimidin-6-yl)-3-oxo-2,3-dihydropyridazin-6-yl]-2-phenylpyrazolo[1,5-a]pyridine mp: decomposed at −250° C. (EtOH); IR (Nujol): 1660, 1620, 1590, 1515 cm$^{-1}$; NMR (DMSO-d$_6$, δ): 0.76 (3H, t, J=7.5 Hz), 1.52(2H, hept, J=7.5 Hz), 3.35–3.54 (1H, m), 3.63–3.87 (1H, m), 4.23 (2H, s), 6.20 (1H, s), 7.07–7.14 (1H, m), 7.09 (1H, d, J=9.9 Hz), 7.26 (1H, d, J=9.9 Hz), 7.46–7.53 (4H, m), 7.62–7.66 (2H, m), 7.89 (1H, d, J=8.9 Hz), 8.85 (1H, d, J=6.9 Hz); (+)-APCI/MS: 499 (M$^+$+1); Analysis Calcd. for C$_{26}$H$_{22}$N$_6$O$_5$.2.5H$_2$O: C, 57.45, H, 5.01, N, 15.46; Found: C, 57.02, H, 4.53, N, 15.31.

EXAMPLE 49

3-[2-(1-Carboxymethyl-2,4-dioxo-3-propyl-1,2,3,4-tetrahydropyrimidin-6-yl)-3-oxo-2,3-dihydropyridazin-6-yl]-2-phenylpyrazolo[1,5-a]pyridine mp: decomposed at −234° C. (IPE); IR (Nujol): 1700, 1670, 1630, 1595, 1520 cm$^{-1}$; NMR (DMSO-d$_6$, δ): 0.90 (3H, t, J=7.3 Hz), 1.50–1.70 (2H, m), 3.64 (1H, d, J=17.5 Hz), 3.82 (2H, t, J=7.3 Hz), 4.47 (1H d, J=17.5 Hz), 6.13 (1H, s), 6.97 (1H, d, J=9.8 Hz), 7.06 (1H, t, J=6.9 Hz), 7.10 (1H, d, J=9.8 Hz), 7.37 (1H, t, J=6.9 Hz), 4.82–7.51 (3H, m), 7.65–7.69 (2H, m), 8.31 (1H, d, J=8.9 Hz), 8.79 (1H, d, J=6.9 Hz); (+)-APCI/MS: 499 (M$^+$+1); Analysis Calcd. for C$_{26}$H$_{22}$N$_6$O$_5$.2.7H$_2$O: C, 57.08, H, 5.04, N, 15.36; Found: C, 57.07, H, 4.53, N, 14.80.

EXAMPLE 50

To a solution of (+)-cis-3-[2-(2-ethoxycarbonylmethyl-2-hydroxycyclohexyl)-3-oxo-2,3-dihydropyridazin-6-yl]-2-phenylpyrazolo[1,5-a]pyridine (600 ml) in a mixture of dioxane (7 ml), methanol (2 ml) and water (4 ml) was added 1N-aqueous sodium hydroxide. solution (2.8 ml), which was stirred for two hours at room temperature. The reaction mixture was poured into ethyl acetate (100 ml) and aqueous layer was collected, which was adjusted to pH 2.3 with 6N-aqueous hydrochloric acid and extracted with ethyl acetate (60 ml). Organic layer was separated, washed with water (30 ml) and dried over magnesium sulfate. Evaporation of the solvent gave a residue, which was recrystallized from a mixture of ethyl acetate and diisopropyl ether to give (±)-cis-3-[2-(2-carboxymethyl-2-hydroxycyclohexyl)-3-oxo-2,3-dihydropyridazin-6-yl]-2-phenylpyrazolo[1,5-a]pyridine (392 mg).

mp: 219–220° C.; FT IR (KBr): 1720.2, 1643.1, 1577.5, 1529.3 cm$^{-1}$; NMR (DMSO-d$_6$, δ): 1.30–1.95 (7H, m), 2.20–2.45(1H, m), 2.34 (2H, s), 4.90–5.05 (1H, m), 6.88 (1H, d, J=9.7 Hz), 7.05–7.15 (2H, m), 7.40–7.65 (6H, m), 8.14 (1H, d, J=8.9 Hz.), 8.83 (1H, d, J=6.9 Hz); (+)-APCI/MS: 445 (M$^+$+1); Analysis Calcd. for C$_{25}$H$_{24}$N$_4$O$_4$.1/2H$_2$O: C, 66.21, H, 5.56, N, 12.35; Found: C, 66.46, H, 5.57, N, 12.15.

EXAMPLE 51

The following compound was obtained according to a similar manner to that of Example 50.

3-[2-(4-Carboxymethylenecyclohexyl)-3-oxo-2,3-dihydropyridazin-6-yl]-2-phenylpyrazolo[1,5-a]pyridine mp: 188–190° C. (EtOH-EtOAc); IR (Nujol): 1705, 1635, 1560 cm$^{-1}$; NMR (CDCl$_3$, δ): 1.68–2.40 (8H, m), 5.70 (1H, s), 5.79 (1H, brd s), 6.78 (1H, d, J=9.6 Hz), 6.84 (1H, t, J=6.9 Hz), 7.00 (1H, d, J=9.6 Hz), 7.28 (1H, dd, J=8.9 Hz, 6.9 Hz), 7.44–7.47 (3H, m), 7.56–7.61 (2H, m), 8.05 (1H, d, J=8.9 Hz), 8.49 (1H, d, J=6.9 Hz); Analysis Calcd. for C$_{25}$H$_{22}$N$_4$O$_3$.1/2H$_2$O: C, 68.95, H, 5.32, N, 12.87; Found: C, 69.11, H, 5.20, N, 12.63.

EXAMPLE 52

A mixture of 3-[2-{2-(2-benzyloxycarbonylethyl)-1-cyclohexenyl}-3-oxo-2,3-dihydropyridazin-6-yl]-2-phenylpyrazolo[1,5-a]pyridine (74 mg) and 1N-sodium hydroxide (0.28 ml) in tetrahydrofuran (4 ml) was refluxed with stirring for 5 hours. The mixture was evaporated under reduced pressure. The residue was dissolved in water. The aqueous layer was washed with ethyl acetate, acidified with 1N-hydrochloric acid and extracted with ethyl acetate. The extract was washed with brine, dried over magnesium sulfate and evaporated under reduced pressure. The residue was recrystallized from ethanol-water to give 3-[2-{2-(2-carboxyethyl)-1-cyclohexenyl}-3-oxo-2,3-dihydropyridazin-6-yl]-2-phenylpyrazolo[1,5-a]-pyridine (54 mg).

mp: 184–185° C.; IR (Nujol): 1695, 1655, 1625, 1585, 1520 cm$^{-1}$; NMR (DMSO-d$_6$, δ): 1.55–1.81 (4H, m), 2.00–2.35 (8H, m), 6.91 (1H, d, J=9.7 Hz), 7.07 (1H, dt, J=1.3, 6.9 Hz), 7.14 (1H, d, J=9.7 Hz), 7.20–7.70 (6H, m), 7.79 (1H, d, J=8.9 Hz), 8.82 (1H, d, J=6.9 Hz), 12.06 (1H, s); (+)-APCI/MS: 441 (M$^+$+1); Analysis Calcd. for C$_{26}$H$_{24}$N$_4$O$_3$: C, 70.89, H, 5.49, N, 12.72; Founds: C, 70.57, H, 5.60, N, 12.42.

EXAMPLE 53

3-[2-{2-(3-Carboxypropyl)-1-cyclohexenyl}-3-oxo-2,3-dihydropyridazin-6-yl]-2-phenylpyrazolo[1,5-a]pyridine was obtained in a similar manner to that of Example 52.

mp: 145–147° C. (AcOEt-n-hexane); IR (Nujol): 1700, 1655, 1585, 1510 cm$^{-1}$; NMR (DMSO-d$_6$, δ): 1.20–1.90 (8H, m), 2.00–2.50 (6H, m), 6.90 (1H, d, J=9.7 Hz), 7.07 (1H, t, J=6.9 Hz), 7.13 (1H, d, J=9.7 Hz), 7.38–7.65 (6H, m), 7.80 (1H, d, J=8.8 Hz), 8.82 (1H, d, J=6.9 Hz), 11.92 (1H, s) (+)-APCI/MS: 455 (M$^+$+1); Analysis Calcd. for C$_{27}$H$_{26}$N$_4$O$_3$: C, 71.35, H, 5.77, N, 12.33; found: C, 70.93, H, 5.76, N, 12.23.

EXAMPLE 54

To a solution of (Z)-3-[2-(2-tert-butoxycarbonylmethylenecyclohexyl)-3-oxo-2,3-dihydropyridazin-6-yl]-2-phenylpyrazolo[1,5-a]pyridine (206 mg) in dichloromethane (0.4 ml) was added trifluoroacetic acid (487 mg). The solution was stirred for 2 hours. The solvent was evaporated in vacuo. The residue was partitioned between 1N aqueous sodium hydroxide and ethyl acetate. The aqueous layer was acidified with 1N hydrochloric acid and the mixture was extracted with dichloromethane. The dichloromethane extract was washed with water (×3) and brine, dried over anhydrous magnesium sulfate, and evaporated in vacuo to give 143 mg of crystals, which was purified by preparative thin layer silica gel chromatography using a mixture of dichloromethane and methanol (10:1) as an eluant to give pale yellow crystals of (Z)-3-[2-(2-carboxymethylenecyclohexyl)-3-oxo-2,3-dihydropyridazin-6-yl]-2-phenylpyrazolo[1,5-a]pyridine (118 mg).

mp: 213–215° C. (dec.) (EtOAc); IR (Nujol): 1695, 1630, 1560, 1520 cm$^{-1}$; NMR (CDCl$_3$, δ): 1.41–1.70 (2H, m), 1.80–2.60 (6H, m), 5.85–6.19 (2H, m), 6.93 (2H, t, J=6.2 Hz), 7.17–7.34 (2H, m), 7.43–7.46 (3H, m), 7.55–7.56 (2H, m), 7.80 (1H, d, J=8.8 Hz), 8.56 (1H, d, J=6.9 Hz); Analysis Calcd. for $C_{25}H_{22}N_4O_3 \cdot 1/2H_2O$: C, 68.95, H, 5.32, N, 12.86; Found: C, 69.19, H, 5.12, N, 12.70.

The following compounds (Examples 55 to 57) were obtained according to a similar manner to that of Example 54.

EXAMPLE 55

3-[2-{2-(N-Carboxymethylcarbamoyl)methyl-1-cyclohexenyl}-3-oxo-2,3-dihydropyridazin-6-yl]-2-phenylpyrazolo[1,5-a]pyridine mp: 190–192° C. (EtOAc); IR (Nujol): 3280, 1727, 1675, 1650, 1580, 1530 cm$^{-1}$; NMR (CDCl$_3$, δ): 1.72–2.63 (8H, m), 2.79 (1H, d, J=14.9 Hz), 3.15 (1H, d, J=14.9 Hz), 3.96 (2H, t, J=5.7 Hz), 6.92 (1H, td, J=7.0, 1.3 Hz), 6.94 (1H, d, J=9.7 Hz), 7.11 (1H, d, J=9.7 Hz), 7.35 (1H, dd, J=8.9, 7.0 Hz), 7.45–7.50 (3H, m), 7.57–7.63 (2H, m), 7.72 (1H, t, J=5.8 Hz), 7.88 (1H, d, J=8.9 Hz), 8.55 (1H, d, J=7.0 Hz); Analysis Calcd. for $C_{27}H_{25}N_5O_4$: C, 67.07, H, 5.21, N, 14.48; Found: C, 66.80, H, 5.38, N, 14.10.

EXAMPLE 56

3-[2-{2-(N-(2-Carboxyethyl)carbamoyl)methyl}-1-cyclohexenyl]-3-oxo-2,3-dihydropyridazin-6-yl]-2-phenylpyrazolo[1,5-a]pyridine mp: 183–184° C. (EtOAc); IR (Nujol): 3275, 1720, 1670, 1650, 1580, 1530 cm$^{-1}$; NMR (CDCl$_3$, δ): 1.69–2.01 (4H, m), 2.09–2.48 (4H, m), 2.54 (2H, t, J=6.5 Hz), 2.74 (1H, d, J=15.0 Hz), 3.09 (1H, d, J=15.0 Hz), 3.41–3.52 (2H, m), 6.89 (1H, d, J=9.7 Hz), 6.93 (1H, td, J=7.0, 1.3 Hz), 7.11 (1H, d, J=9.7 Hz), 7.34 (1H, dd, J=8.9, 7.0 Hz), 7.45–7.50 (3H, m), 7.57–7.64 (3H, m), 7.88 (1H, d, J=8.9 Hz), 8.55 (1H, d, J=7.0 Hz); Analysis Calcd. for $C_{28}H_{27}N_5O_4$: C, 67.59, H, 5.47, N, 14.08; Found: C, 67.25, H, 5.57, N, 13.77.

EXAMPLE 57

3-[2-(2-Carboxymethoxyiminocyclohexyl)-3-oxo-2,3-dihydropyridazin-6-yl]-2-phenylpyrazolo[1,5-a]pyridine mp: 208° C. (dec.) (Et$_2$O); IR (Nujol): 1703, 1635, 1567, 1539 cm$^{-1}$; NMR (DMSO-d$_6$, δ): 1.32–2.22 (7H, m), 3.19 (1H, d, J=14.2 Hz), 4.38 (2H, s), 5.57 (1H, dd, J=10.8, 5.0 Hz), 6.85 (1H, d, J=9.6 Hz), 7.04 (1H, d, J=9.6 Hz), 7.07 (1H, t, J=6.9 Hz), 7.39–7.49 (3H, m), 7.56–7.59 (2H, m), 7.80 (1H, d, J=8.9 Hz), 8.81 (1H, d, J=6.9 Hz), 12.6 (1H, brd s); (+)-APCI/MS: 458 (M$^+$+1); Analysis Calcd. for $C_{25}H_{23}N_5O_4 \cdot 0.2H_2O$: C, 65.12, H, 5.12, N, 15.19; found: C, 65.26, H, 5.30, N, 14.69.

EXAMPLE 58

To a solution of 3-[2-(2-tert-butoxycarbonylmethyl-1-cyclohexenyl)-3-oxo-2,3-dihydropyridazin-6-yl]-2-phenylpyrazolo[1,5-a]pyridine (248 g) in dichloromethane (500 ml) was added dropwise trifluoroacetic acid (396 ml) at 5° C. After addition, a reaction mixture was allowed to warm to ambient temperature, and stirred for 20 hours. Solvent was removed by distillation and toluene azeotrope (500 ml×2). A residue was dissolved in a mixture of 1N-aqueous sodium hydroxide solution (3.5 l) and water (0.5 l), which was washed with ethyl acetate (600 ml). Aqueous layer was added dichloromethane (2 l) and the pH was adjusted to pH 3.5 with 2N-aqueous hydrochloric acid. Organic layer was separated and aqueous layer was reextracted with dichloromethane (1 l). Organic layer was combined, which was washed with water (1 l×2) and dried over magnesium sulfate. Evaporation of the solvent gave a crude solid, which was recrystallized from 85% aqueous ethanol (1.25 l) and collected by filtration to give 3-[2-(2-carboxymethyl-1-cyclohexenyl)-3-oxo-2,3-dihydropyridazin-6-yl]-2-phenylpyrazolo[1,5-a]pyridine (152.2 g). Mother liquor was concentrated to give crude solid, which was recrystallized in the similar manner to give the second crystal of the object compound (27.63 g).

mp: 218.0–219.0° C.; FT IR (KBr): 1724.0, 1639.2, 1579.4, 1531.2 cm$^{-1}$; NMR (CDCl$_3$, δ): 1.70–2.00 (4H, m), 2.20–2.70 (4H, m), 2.91 (1H, d, J=14.0 Hz), 3.18 (1H, d, J=14.0 Hz), 6.89–7.00 (2H, m), 7.17 (1H, d, J=9.6 Hz), 7.30–7.61 (6H, m), 7.94 (1H, d, J=9.0 Hz), 8.55 (1H, d, J=6.9 Hz), 12.16 (1H, s); (+)-APCI/MS: 427 (M$^+$+1).

EXAMPLE 59

3-[2-(2-Carboxymethyl-2-cyclohexen-1-yl)-3-oxo-2,3-dihydropyridazin-6-yl]-2-phenylpyrazolo[1,5-a]pyridine was obtained in substantially the same manner as that of Example 58.

mp: 164.0–166.0° C.; FT IR (KBr): 2931.3, 1720.2, 1641.1, 1571.7, 1529.3 cm$^{-1}$; NMR (DMSO-d$_6$, δ): 1.50–2.20 (6H, m), 2.77 (2H, ABq, J=15.9, 15.8 Hz), 5.67 (1H, br s), 5.97 (1H, s), 6.86 (1H, d, J=9.6 Hz), 7.03–7.11 (2H, m), 7.38–7.63 (6H, m), 7.93 (1H, d, J=8.9 Hz), 8.81 (1H, d, J=6.9 Hz), 12.13 (1H, br s); (+)-APCI/MS: 427 (M$^+$+1); Analysis Calcd. for $C_{25}H_{22}N_4O_3$: C, 70.41, H, 5.20, N, 13.14; Found: C, 70.58, H, 5.27, N, 13.51.

EXAMPLE 60

(E)-3-[2-{2-Carboxymethylenecyclohexyl}-3-oxo-2,3-dihydropyridazin-6-yl]-2-phenylpyrazolo[1,5-a]pyridine was obtained in substantially the same manner as that of Example 58.

mp: 250–253° C. FT IR (KBr): 2950.6, 1714.4, 1650.8, 1595.2, 1527.3 cm$^{-1}$; NMR (DMSO-d$_6$, δ): 1.20–2.20 (7H, m), 3.80–4.00 (1H, m), 4.93 (1H, s), 5.40–5.51 (1H, m), 6.98 (1H, d, J=9.7 Hz), 7.04–7.11 (1H, m), 7.21 (1H, d, J=9.7 Hz), 7.40–7.63 (6H, m), 7.85 (1H, d, J=8.9 Hz), 8.84 (1H, d, J=6.9 Hz), 12.21 (1H, br s) (+)-APCI/MS: 427 (M$^+$+1); Analysis Calcd. for $C_{25}H_{22}N_4O_3$: C, 70.41, H, 5.20, N, 13.14; Found: C, 70.18, H, 5.02, N, 13.51.

EXAMPLE 61

3-[2-(2-Carboxymethyl-1-cyclohexenyl)-3-oxo-2,3-dihydropyridazin-6-yl]-2-phenylpyrazolo[1,5-a]pyridine (16.74 g) was dissolved in 0.1N aqueous sodium hydroxide solution (393 ml). After the solution was filtered, the filtrate was evaporated to dryness under reduced pressure. The residue was recrystallized from a mixture of acetone and water (10:1) to give yellow crystals of sodium salt of 3-[2-(2-carboxymethyl-1-cyclohexenyl)-3-oxo-2,3-dihydropyridazin-6-yl]-2-phenylpyrazolo[1,5-a]pyridine (13.23 g).

mp: 192–193° C.; IR (Nujol): 1640, 1600, 1515 cm$^{-1}$; NMR (D$_2$O, δ): 1.43–1.96 (8H, m), 2.35 (1H, d, J=16.1 Hz), 2.43 (1H, d, J=16.1 Hz), 6.42 (1H, d, J=9.6 Hz), 6.54 (1H, d, J=9.6 Hz), 6.56 (1H, t, J=6.9 Hz), 6.87–7.16 (6H, m), 7.23 (1H, d, J=8.9 Hz), 7.87 (1H, d, J=6.9 Hz).

EXAMPLE 62

3-[2-(2-Carboxymethyl-1-cyclohexenyl)-3-oxo-2,3-dihydropyridazin-6-yl]-2-phenylpyrazolo[1,5-a]pyridine (1.11 g) was dissolved in a mixture of 0.1N aqueous sodium hydroxide solution (35 ml) and ethanol (10 ml). The pH of the solution was adjusted to pH 4.8 with 1N aqueous hydrochloric acid at 13 to 15° C. with stirring. The pale yellow crystals were collected by filtration, washed with water, and dried under reduced pressure to give 3-[2-(2-carboxymethyl-1-cyclohexenyl)-3-oxo-2,3-dihydropyridazin-6-yl]-2-phenylpyrazolo[1,5-a]pyridine type A crystals (1.03 g).

mp: 209–210° C.; FT IR (KBr) 2935, 2837, 1722, 1639, 1576, 1529, 1487, 1468, 1417, 1348, 1309, 1188, 1144, 1012, 922, 849, 750, 700, 619, 573 cm$^{-1}$.

EXAMPLE 63

3-[2-(2-Carboxymethyl-1-cyclohexenyl)-3-oxo-2,3-dihydropyridazin-6-yl]-2-phenylpyrazolo[1,5-a]pyridine (1.32 g) was dissolved in boiling 80% aqueous ethanol (26 ml). The solution was stirred at ambient temperature for 3 hours and then cooled in an ice-water bath with stirring for 2 hours. The colorless crystals were collected by filtration, washed with 80% aqueous ethanol, and dried under reduced pressure to give colorless crystals of 3-[2-(2-carboxymethyl-1-cyclohexenyl)-3-oxo-2,3-dihydropyridazin-6-yl]-2-phenylpyrazolo[1,5-a]pyridine type B crystals (1.19 g).

mp: 218.5–219.5° C.; FT IR (KBr): 2937, 1724, 1639, 1579, 1531, 1470, 1421, 1348, 1315, 1265, 1234, 1190, 1147, 1016, 860, 760, 702, 669, 617, 567 cm$^{-1}$.

EXAMPLE 64

(E)-3-[2-(2-Carboxymethylenecyclohexyl)-3-oxo-2,3-dihydropyridazin-6-yl]-2-phenylpyrazolo[1,5-a]pyridine (36.8 mg) was suspended in dichloromethane and the mixture was cooled in an ice bath. To this was added thionyl chloride (0.1 ml). After the reaction mixture was stirred at room temperature for 4 hours, the solvent was evaporated in vacuo. The residue was dissolved in methanol (2 ml), and stirred at room temperature for 10 minutes. Methanol was evaporated in vacuo and the residue was partitioned between dichloromethane (10 ml) and saturated aqueous sodium bicarbonate. After an additional extraction with dichloromethane (10 ml), the combined extracts were washed with brine (10 ml), dried over anhydrous magnesium sulfate, and evaporated in vacuo. The oily residue was crystallized from ethyl acetate to give colorless crystals of (E)-3-[2-(2-methoxycarbonylmethylenecyclohexyl)-3-oxo-2,3-dihydropyridazin-6-yl]-2-phenylpyrazolo[1,5-a]pyridine (36.3 mg). The spectroscopic data for this compound were identical to those for the authentic sample obtained in Example 31.

EXAMPLE 65

A solution of 3-[2-(2-carboxymethyl-1-cyclohexenyl)-3-oxo-2,3-dihydropyridazin-6-yl]-2-phenylpyrazolo[1,5-a]-pyridine (222 mg) and N,N-dimethylformamide (1 drop) in dichloromethane (4 ml) was cooled in an ice bath (5° C). To this was added dropwise oxalyl chloride (99 mg). After the mixture was stirred at 5° C. for 20 minutes and at room. temperature for additional 2 hours, volatile materials were removed in vacuo to give the acid chloride. On the other hand, glycine tert-butyl ester hydrochloride (95.8 mg) and triethylamine (158 mg) was dissolved in dichloromethane (5 ml) and the solution was cooled in an ice bath (5° C.). To this was added a solution of the above acid chloride in dichloromethane (2 ml). The reaction mixture was stirred at room temperature for 5.5 hours. The reaction mixture was sequentially washed with 1N hydrochloric acid (5 ml), saturated aqueous sodium bicarbonate (8 ml), and brine (5 ml), dried over anhydrous magnesium sulfate, and evaporated in vacuo. The crude material was purified by column chromatography on silica. gel using a mixture of dichloromethane and ethyl acetate. (10:1) as an eluant to give 3-[2-{2-(N-(tert-butoxycarbonylmethyl)carbamoyl)methyl-1-cyclohexenyl}-3-oxo-2,3-dihydropyridazin-6-yl]-2-phenylpyrazolo[1,5-a]-pyridine (152.9 mg)

IR (CH$_2$Cl$_2$): 3280, 1735, 1650, 1585, 1525 cm$^{-1}$; NMR (CDCl$_3$, δ): 1.44 (9H, s), 1.75–1.92 (4H, m), 2.11–2.52 (4H, m), 2.78 (1H, d, J=14.7 Hz), 3.16 (1H, d, J=14.7 Hz), 3.74 (1H, dd, J=17.6, 5.5 Hz), 3.91 (1H, dd, J=17.6, 6.0 Hz), 6.84 (1H, d, J=9.7 Hz), 6.93 (1H, td, J=6.9, 1.4 Hz), 7.10 (1H, d, J=9.7 Hz), 7.32 (1H, ddd, J=8.9, 6.9, 1.1 Hz), 7.46–7.51 (3H, m), 7.60–7.68 (3H, m), 7.88 (1H, d, J=8.9 Hz) (+)-APCI/MS: 540 (M$^+$+1).

EXAMPLE 66

To a suspension of 3-[2-(2-carboxymethyl)-1-cyclohexenyl)-3-oxo-2,3-dihydropyridazin-6-yl]-2-phenylpyrazolo[1,5-a]pyridine (0.20 g) in dry dichloromethane (4 ml) at room temperature was added thionyl chloride (0.046 ml). After stirring for 2 hours and 30 minutes, the mixture was evaporated under reduced pressure. The residue was dissolved in tetrahydrofuran-acetonitrile (1:1, 4 ml), and a solution of 10%-trimethylsilyldiazomethane in hexane was added at 0° C. The mixture was stirred at 0° C. for 3 hours, then evaporated under reduced pressure. Benzyl alcohol (1 ml) and 2,4,6-trimethylpyridine (1 ml) were added to the residue. The mixture was stirred at 180–185° C. for 7 minutes. Ethyl acetate was added to the mixture. The mixture was washed with 10% aqueous citric acid, water, and brine. After the mixture had been dried over magnesium sulfate, the solvent and excess benzyl alcohol were evaporated in reduced pressure. The residue was chromatographed on silica gel (20 ml) using a mixture of dichloromethane-methanol (100:1). The desired fractions were collected and evaporated under reduced pressure. The residue was recrystallized from diethyl ether to give 3-[2-{2-(2-benzyloxycarbonylethyl)-1-cyclohexenyl}-3-oxo-2,3-dihydropyridazin-6-yl]-2-phenylpyrazolo[1,5-a]pyridine (73 mg).

mp: 111–113° C.; IR (Nujol): 1735, 1710, 1670, 1630, 1595, 1530 cm$^{-1}$; NMR (CDCl$_3$, δ): 1.65–2.00 (4H, m), 2.10–2.60 (8H, m), 5.02 (2H, s), 6.76 (1H, d, J=9.7 Hz), 6.88

(1H, dt, J=1.4, 6.9 Hz), 7.00 (1H, d, J=9.7 Hz), 7.20–7.30 (6H, m), 7.43–7.47 (3H, m), 7.60–7.66 (2H, m), 7.89 (1H, d, J=8.9 Hz), 8.50 (1H, d, J=6.9 Hz); (+)-APCI/MS: 531 (M$^+$+1); Analysis Calcd. for $C_{33}H_{30}N_4O_3 \cdot 1/2H_2O$: C, 73.45, H, 5.79, N, 10.38; Found: C, 73.67, H, 5.68, N, 10.45.

EXAMPLE 67

3-[2-{2-(3-Benzyloxycarbonylpropyl)-1-cyclohexenyl}-3-oxo-2,3-dihydropyridazin-6-yl]-2-phenylpyrazolo[1,5-a]pyridine was contained in a similar manner to that of Example 66.

IR (Nujol): 1720, 1660, 1590, 1520 cm$^{-1}$; NMR (CDCl$_3$, δ): 1.67–2.60 (14H, m), 5.00 (2H, s), 6.76 (1H, d, J=9.6 Hz), 6.87 (1H, t, J=6.9 Hz), 7.00 (1H, d, J=9.6 Hz), 7.20–7.37 (6H, m), 7.40–7.50 (3H, m), 7.61–7.67 (2H, m), 7.90 (1H, d, J=9.0 Hz), 8.50 (1H, d, J=6.4 Hz); (+)-APCI/MS: 545 (M$^+$+1).

EXAMPLE 68

To a solution of 3-[2-(2-carboxymethyl-1-cyclohexenyl)-3-oxo-2,3-dihydropyridazin-6-yl]-2-phenylpyrazolo[1,5-a]pyridine (1.5 g) in a mixture of tetrahydrofuran (20 ml) and dichloromethane (20 ml) was added in turn with 1-hydroxybenzotriazole (563 mg), 1-ethyl-3-(3-dimethylaminopropyl)carbodiimide (950 µl) and sarcosine ethyl ester hydrochloride (640 mg) at room temperature. The reaction mixture was stirred for two hours, which was poured into ethyl acetate (300 ml), washed in turn with water (30 ml×2), saturated sodium hydrogen carbonate in water (50 ml) and brine (50 ml×2), and dried over magnesium sulfate. Evaporation of the solvent gave a residue, which was chromatographed on silica gel (200 ml) eluting with ethyl acetate. Fractions containing desired product were collected. Evaporation of the solvent gave a residue, which was recrystallized from a mixture of ethyl acetate and n-hexane to give 3-[2-{2-(N-ethoxycarbonylmethyl-N-methylcarbamoyl)methyl-1-cyclohexenyl}-3-oxo-2,3-dihydropyridazin-6-yl]-2-phenylpyrazolo[1,5-a]pyridine (1.12 g).

mp: 56–60° C.; FT IR (KBr) 1743.3, 1670.1, 1639.2, 1591.0, 1527.3 cm$^{-1}$; NMR (DMSO-d$_6$, δ): 0.96–1.67 (3H, m), 1.60–1.85 (4H, m), 2.05–2.40 (4H, m), 2.70–3.00 (5H, m), 3.90–4.10 (4H, m), 6.80–7.13 (3H, m), 7.35–7.63 (6H, m), 7.89 (1H, d, J=8.9 Hz), 8.81 (1H, d, J=6.9 Hz); (+)-APCI/MS: 526 (M$^+$+1); Analysis Calcd. for $C_{30}H_{31}N_5O_4$: C, 68.55, H, 5.94, N, 13.32; Found: C, 68.32, H, 6.06, N, 12.86.

The following compounds (Examples 69 to 86) were obtained according to a similar manner to that of Example 68.

EXAMPLE 69

3-[2-(2-Carbamoylmethyl-1-cyclohexenyl)-3-oxo-2,3-dihydropyridazin-6-yl]-2-phenylpyrazolo[1,5-a]pyridine mp: 204.0–205.0° C. (CH$_2$Cl$_2$-n-hexane); FT IR (KBr): 1672.0, 1658.5, 1589.1, 1527.3 cm$^{-1}$; NMR (DMSO-d$_6$, δ): 1.60–1.85 (4H, m), 2.05–2.40(4H, m), 2.71 (2H, ABq, J=14.7, 20.7 Hz), 6.96 (1H, d, J=9.7 Hz), 7.04–7.18 (2H, m), 7.38–7.70 (6H, m), 7.92 (1H, d, J=8.9 Hz), 8.82 (1H, d, J=6.9 Hz); (+)-APCI/MS: 426 (M$^+$+1); Analysis Calcd. for $C_{25}H_{23}N_5O_2 \cdot 1/2H_2O$: C, 69.11, H, 5.57, N, 16.12; Found: C, 69.49, H, 5.41, N, 15.83.

EXAMPLE 70

3-[2-{2-(3-Carbamoylpropyl)-1-cyclohexenyl}-3-oxo-2,3-dihydropyridazin-6-yl]-2-phenylpyrazolo[1,5-a]pyridine IR (Film): 3320, 3200, 3050, 1660, 1590, 1525 cm$^{-1}$; NMR (CDCl$_3$, δ): 1.60–2.60 (14H, m), 5.43 (1H, s), 6.77 (1H, s), 6.80 (1H, d, J=9.7 Hz), 6.92 (1H, t, J=6.8 Hz), 7.09 (1H, d, J=9.7 Hz), 7.32 (1H, t, J=6.8 Hz), 7.45–7.64 (5H, m), 7.87 (1H, d, J=8.9 Hz), 8.53 (1H, d, J=6.5 Hz); (+)-APCI/MS: 454 (M$^+$+1).

EXAMPLE 71

3-[2-{2-(N,N-Dimethylcarbamoyl)methyl-1-cyclohexenyl}-3-oxo-2,3-dihydropyridazin-6-yl]-2-phenylpyrazolo[1,5-a]pyridine mp: 80.0–81.0° C. (CH$_2$Cl$_2$-n-hexane); FT IR (KBr) 1666.2, 1639.2, 1591.0, 1527.3 cm$^{-1}$; NMR (DMSO-D$_6$, δ): 1.60–1.85 (4H, m), 2.05–2.40 (4H, m), 2.69 (3H, s), 2.80 (3H, s), 2.93 (2H, s), 6.89 (1H, d, J=9.7 Hz), 7.00–7.11 (2H, m), 7.37–7.66 (6H, m), 7.90 (1H, d, J=8.9 Hz), 8.81 (1H, d, J=6.9 Hz); (+)-APCI/MS: 454 (M$^+$+1); Analysis Calcd. for $C_{27}H_{27}N_5O_2 \cdot 1/2H_2O$: C, 70.11, H, 6.10, N, 15.14; Found: C, 70.00, H, 6.17, N, 14.98.

EXAMPLE 72

3-[2-{2-(N-(2-Ethoxycarbonylethyl)-N-methylcarbamoyl)methyl-1-cyclohexenyl}-3-oxo-2,3-dihydropyridazin-6-yl]-2-phenylpyrazolo[1,5-a]pyridine FT IR (KBr): 1735.6, 1666.2, 1645.0, 1592.9, 1529.3 cm$^{-1}$; NMR (DMSO-d$_6$, δ): 0.95–1.16 (3H, m), 1.55–1.80 (4H, m), 2.10–2.50 (6H, m), 2.65–3.20 (7H, m), 3.80–4.05 (2H, m), 6.88 (1H, d, J=9.7 Hz), 7.00–7.12 (2H, m), 7.30–7.65 (6H, m), 7.90 (1H, d, J=8.9 Hz), 8.81 (1H, d, J=6.9 Hz); (+)-APCI/MS: 540 (M$^+$+1).

EXAMPLE 73

3-[2-{2-(N-(3-Methoxycarbonylpropyl)carbamoyl)methyl-1-cyclohexenyl}-3-oxo-2,3-dihydropyridazin-6-yl]-2-phenylpyrazolo[1,5-a]pyridine FT IR (KBr): 1735.6, 1668.1, 1589.1, 1529.3 cm$^{-1}$; NMR (DMSO-d$_6$, δ): 1.45–1.85 (6H, m), 2.16–2.35 (6H, m), 2.65–3.10 (4H, m), 3.53 (3H, s), 6.95 (1H, d, J=9.7 Hz), 7.03–7.12 (1H, m), 7.15 (1H, d, J=9.7 Hz), 7.35–7.67 (7H, m), 7.91 (1H, d, J=8.9 Hz), 8.82 (1H, d, J=6.9 Hz); (+)-APCI/MS: 526 (M$^+$+1).

EXAMPLE 74

3-[2-{2-(N-(2-Hydroxyethyl)carbamoyl)methyl-1-cyclohexenyl}-3-oxo-2,3-dihydropyridazin-6-yl]-2-phenylpyrazolo[1,5-a]pyridine FT IR (KBr): 3315.0, 1656.6, 1585.2, 1529.3 cm$^{-1}$; NMR (CDCl$_3$, δ): 1.75–2.00 (4H, m), 2.10–2.50 (4H, m), 2.60–2.80 (1H, m), 3.10–3.30 (2H, m), 3.50–3.90 (4H, m), 6.83 (1H, d, J=9.7 Hz), 6.90–7.00 (1H, m), 7.14 (1H, d, J=9.7 Hz), 7.30–7.40 (1H, m), 7.45–7.70 (6H, m), 7.87 (1H, d, J=8.9 Hz), 8.54 (1H, d, J=6.9 Hz); (+)-APCI/MS: 470 (M$^+$+1).

EXAMPLE 75

3-[2-{2-(N-(2-(tert-Butoxycarbonyl)ethyl)carbamoyl)-methyl)-1-cyclohexenyl}-3-oxo-2,3-dihydropyridazin-6-yl]-2-phenylpyrazolo[1,5-a]pyridine IR (CH$_2$Cl$_2$): 3280, 1720, 1655, 1585, 1525 cm$^{-1}$; NMR (CDCl$_3$, δ): 1.45 (9H, s), 1.75–1.96 (4H, m), 2.15–2.30 (2H, m), 2.43 (4H, t, J=6.9 Hz), 2.71 (1H, d, J=14.7 Hz), 3.09 (1H, d, J=14.7 Hz), 3.35–3.49 (2H, m), 6.82 (1H, d, J=9.7 Hz), 6.93 (1H, td, J=7.0, 1.3 Hz), 7.09 (1H, d, J=9.7 Hz), 7.32 (1H, dd, J=8.9, 7.0 Hz), 7.46–7.49 (4H, m), 7.60–7.65

(2H, m), 7.87 (1H, d, J=8.9 Hz), 8.53 (1H, d, J=7.0 Hz); (+)-APCI/MS: 554 (M⁺+1).

EXAMPLE 76

3-[2-{2-(N-Methylcarbamoyl)methyl-1-cyclohexenyl}-3-oxo-2,3-dihydropyridazin-6-yl]-2-phenylpyrazolo[1,5-a]pyridine FT IR (KBr): 1658.5, 1587.1, 1529.3 cm$^{-1}$; NMR (CDCl$_3$, δ): 1.80–2.00 (4H, m), 2.15–2.50 (4H, m), 2.60–2.70 (1H, m), 2.74 (3H, d, J=4.7 Hz), 3.12 (1H, d, J=14.8 Hz), 6.84 (1H, d, J=9.6 Hz), 6.90–7.00 (1H, m), 7.11 (1H, d, J=9.6 Hz), 7.29–7.65 (6H, m), 7.86 (1H, d, J=9.0 Hz), 8.54 (1H, d, J=6.9 Hz); (+)-APCI/MS: 440 (M⁺+1).

EXAMPLE 77

3-[2-{2-(3-(N-Methylcarbamoyl)propyl)-1-cyclohexenyl}-3-oxo-2,3-dihydropyridazin-6-yl]-2-phenylpyrazolo[1,5-a]pyridine IR (Film): 3320, 1650, 1590, 1530 cm$^{-1}$; NMR (DMSO-d$_6$, δ): 1.40–2.40 (14H, m), 2.46 (3H, d, J=4.6 Hz), 6.90 (1H, d, J=9.7 Hz), 7.05 (1H, t, J=6.9 Hz), 7.12 (1H, d, J=9.7 Hz), 7.39–7.66 (7H, m), 7.80 (1H, d, J=8.9 Hz), 8.82 (1H, d, J=6.9 Hz); (+)-APCI/MS: 468 (M⁺+1).

EXAMPLE 78

3-[2-{2-(3-(N,N-Dimethylcarbamoyl)propyl)-1-cyclohexenyl}-3-oxo-2,3-dihydropyridazin-6-yl]-2-phenylpyrazolo[1,5-a]pyridine IR (Film): 1650, 1590, 1520 cm$^{-1}$; NMR (DMSO-d$_6$, δ): 1.40–2.40 (14H, m), 2.65 (3H, s), 2.73 (3H, S), 6.89 (1H, d, J=9.7 Hz), 7.07 (1H, t, J=6.8 Hz), 7.12 (1H, d, J=9.7 Hz), 7.38–7.67 (6H, m), 7.81 (1H, d, J=8.9 Hz), 8.82 (1H, d, J=6.8 Hz); (+)-APCI/MS: 482 (M⁺+1).

EXAMPLE 79

3-[2-{(2-(3-(N-Ethoxycarbonylmethyl)carbamoyl)-propyl)-1-cyclochexenyl}-3-oxo-2,3-dihydropyridazin-6-yl]-2-phenylpyrazolo[1,5-a]pyridine mp: 128–130° C. (AcOEt-Et$_2$O); IR (Nujol): 3290, 1750, 1655, 1590, 1535 cm$^{-1}$; NMR (DMSO-$_6$, δ): 1.13 (3H, t, J=7.1 Hz), 1.50–2.40 (14H, m), 3.71 (2H, d, J=5.9 Hz), 4.01 (2H, q, J=7.1 Hz), 6.90 (1H, d, J=9.6 Hz), 7.06 (1H, t, J=6.8 Hz), 7.11 (1H, d, J=9.6 Hz), 7.39–7.63 (6H, m), 7.80 (1H, d, J=8.9 Hz), 8.14 (1H, t, J=5.9 Hz), 8.81 (1H, d, J=6.8 Hz); (+)-APCI/MS: 540 (M⁺+1).

EXAMPLE 80

3-[2-{2-(Thiomorpholin-4-ylcarbonyl)methyl-1-cyclohexenyl}-3-oxo-2,3-dihydropyridazin-6-yl]-2-phenylpyrazolo[1,5-a]pyridine mp: 180.5–182.5° C.; FT IR (KBr): 1660.4, 1587.1, 1529.3 cm$^{-1}$; NMR (CDCl$_3$, δ): 1.60–2.00 (4H, m), 2.10–2.70 (8H, m), 3.10 (2H, m), 3.60–4.00 (4H, m), 6.78 (1H, d, J=9.7 Hz), 6.94 (1H, t, J=6.9 Hz), 7.05 (1H, d, J=9.7 Hz), 7.26–8.05 (6H, m), 8.00 (1H, d, J=9.0 Hz), 8.55 (1H, d, J=6.9 Hz); (+)-APCI/MS: 512 (M⁺+1).

EXAMPLE 81

3-[2-{2-(4-Methylpiperazin-1-ylcarbonyl)methyl-1-cyclohexenyl}-3-oxo-2,3-dihydropyridazin-6-yl]-2-phenylpyrazolo[1,5-a]pyridine hydrochloride mp: 188–191° C. (H$_2$O); IR (Nujol): 2675, 2600, 1650, 1630, 1580, 1530 cm$^{-1}$; NMR (DMSO-d$_6$, δ): 1.55–1.90 (3H, m), 2.00–2.50 (3H, m), 2.60–3.60 (10H, m), 2.66 (3H, s), 3.87 (1H, s), 4.34 (1H, s), 6.90 (1H, d, J=9.7 Hz), 7.05–7.13 (1H, m), 7.10 (1H, d, J=9.7 Hz), 7.40–7.60 (4H, m), 7.61–7.70 (2H, m), 7.89 (1H, d, J=8.8 Hz), 8.83 (1H, d, J=6.9 Hz), 11.01 (1H, s); (+)-APCI/MS: 509 (M⁺+1).

EXAMPLE 82

3-[2-{2-(4-Triphenylmethylpiperazin-1-ylcarbonyl)methyl-1-cyclohexenyl}-3-oxo-2,3-dihydropyridazin-6-yl]-2-phenylpyrazolo[1,5-a]pyridine mp: 249.5–250.5° C.; FT IR (KBr): 1666.2, 1637.3, 1594.8, 1529.3 cm$^{-1}$; NMR (CDCl$_3$, δ): 1.56–2.60 (12H, m), 2.80–3.20 (2H, m), 3.40–3.90 (4H, m), 6.69 (1H, d, J=9.7 Hz), 6.83 (1H, t, J=6.9 Hz), 6.95 (1H, d, J=9.7 Hz), 7.10–7.70 (21H, m), 7.92 (1H, d, J=8.8 Hz), 8.48 (1H, d, J=6.9 Hz); (+)-FAB/MS: 737.2 (M⁺+1).

EXAMPLE 83

3-[2-(2-Morpholinocarbonylmethyl-1-cyclohexenyl)-3-oxo-2,3-dihydropyridazin-6-yl]-2-phenylpyrazolo[1,5-a]pyridine mp: 202–204° C. (AcOEt-hexane); IR (Nujol): 1655, 1590, 1530 cm$^{-1}$; NMR (CDCl$_3$, δ): 1.70–2.0 (4H, m), 2.10–2.60 (4H, m), 3.10 (2H, s), 3.30–3.70 (8H, m), 6.76 (1H, d, J=9.8 Hz), 6.92 (1H, t, J=6.9 Hz), 7.05 (1H, d, J=9.8 Hz), 7.34 (1H, t, J=6.9 Hz), 7.45–7.49 (3H, m), 7.59–7.63 (2H, m), 7.99 (1H, d, J=9.0 Hz), 8.52 (1H, d, J=6.9 Hz); (+)-APCI/MS: 496 (M⁺+1).

EXAMPLE 84

3-[2-{2-(Pyrrolidin-1-ylcarbonyl)methyl-1-cyclohexenyl}-3-oxo-2,3-dihydropyridazin-6-yl]-2-phenylpyrazolo[1,5-a]pyridine mp: 178–179° C. (EtOAc); IR (Nujol): 1660, 1635, 1585, 1525 cm$^{-1}$; NMR (CDCl$_3$, δ): 1.51–2.76 (12H, m), 2.86–3.55 (6H, m), 6.77 (1H, d, J=9.7 Hz), 6.92 (1H, t, J=6.9 Hz), 7.03 (1H, d, J=9.7 Hz), 7.36 (1H, dd, J=8.9, 6.9 Hz), 7.45–7.48 (3H, m), 7.60–7.65 (2H, m), 8.11 (1H, d, J=8.9 Hz), 8.53 (1H, d, J=6.9 Hz).

EXAMPLE 85

3-[2-{2-(Piperidinocarbonyl)methyl-1-cyclohexenyl}-3-oxo-2,3-dihydropyridazin-6-yl]-2-phenylpyrazolo[1,5-a]pyridine mp: 184–185° C. (EtOAc-Et$_2$O); IR (Nujol): 1660, 1635, 1585, 1530 cm$^{-1}$; NMR (CDCl$_3$, δ): 1.28–2.00 (6H, m), 1.70–1.97 (4H, m), 2.20–2.58 (4H, m), 3.09 (2H, s), 3.20–3.43 (4H, m), 6.78 (1H, d, J=9.7 Hz), 6.93 (1H, dd, J=8.9, 6.7 Hz), 7.03 (1H, d, J=9.7 Hz), 7.35 (1H, dd, J=6.7, 8.9 Hz), 7.46–7.49 (3H, m), 7.60–7.63 (2H, m), 8.05 (1H, d, J=8.9 Hz), 8.52 (1H, d, J=6.7 Hz).

EXAMPLE 86

3-[2-{2-(4-Methylaminopiperidinocarbonyl)methyl-1-cyclohexenyl}-3-oxo-2,3-dihydropyridazin-6-yl]-2-phenylpyrazolo[1,5-a]pyridine mp: 101–105° C. (H$_2$O); IR (Nujol): 1660, 1630, 1590, 1525 cm$^{-1}$; NMR (DMSO-d$_6$, δ): 0.60–1.30 (2H, m), 1.70–2.10 (8H, m), 2.20–2.80 (7H, m), 2.82–3.05 (1H, m), 3.11 (2H, s), 3.76–3.83 (1H, m), 4.37 (1H, brd s), 6.77 (1H, d, J=9.7 Hz), 6.92 (1H, t, J=6.9 Hz), 7.03 (1H, d, J=9.7 Hz), 7.35 (1H, t, J=8.9 Hz), 7.45–7.49 (3H, m), 7.60–7.64 (2H, m), 8.03 (1H, d, J=8.9 Hz), 8.51 (1H, d, J=6.9 Hz); (+)-APCI/MS: 523 (M⁺+1).

EXAMPLE 87

A mixture of 3-[2-(2-oxocyclohexyl)-3-oxo-2,3-dihydropyridazin-6-yl]-2-phenylpyrazolo[1,5-a]pyridine (231 mg), semicarbazide hydrochloride (101 mg), potassium carbonate (125 mg), water (2 ml), and ethanol (10 ml) was heated under reflux for 4 hours. Ethanol was evaporated in vacuo and the residue was partitioned between dichloromethane (30 ml) and saturated aqueous sodium bicarbonate (30 ml). After an additional extraction with dichloromethane, the combined extracts were washed with brine (20 ml), dried over anhydrous sodium sulfate, and evaporated in vacuo to give colorless crystals of 3-[2-(2-carbamoylhydrazonocyclohexyl)-3-oxo-2,3-dihydropyridazin-6-yl]-2-phenylpyrazolo[1,5-a]pyridine (125.8 mg).

mp: 227–229° C. (EtOH); IR (Nujol): 1680, 1650, 1580, 1520 cm$^{-1}$; NMR (DMSO-d$_6$, δ): 1.22–1.46 (1H, m), 1.58–2.24 (6H, m), 3.04 (1H, d, J=14.7 Hz), 3.33–3.50 (1H, m), 5.52 (1H, dd, J=10.4, 5.1 Hz), 6.91 (1H, d, J=9.6 Hz), 7.03–7.13 (2H, m), 7.37–7.54 (7H, m), 7.79 (1H, d, J=8.8 Hz), 8.82 (1H, d, J=6.8 Hz), 9.47 (1H, s); (+) APCI/MS: 442 (M$^+$+1); Analysis Calcd. for C$_{24}$H$_{23}$N$_7$O$_2$. H$_2$O: C, 62.73, H, 5.48, N, 21.33; Found: C, 62.50, H, 5.47, N, 20.89.

The following compounds (Examples 88 to 92) were obtained according to a similar manner to that of Example 87.

EXAMPLE 88

3-[2-(2-Hydrazonocyclohexyl)-3-oxo-2,3-dihydropyridazin-6-yl]-2-phenylpyrazolo[1,5-a]pyridine mp: 161–162° C. (EtOAc-IPE); IR (Nujol): 1650, 1580 cm$^{-1}$; NMR (CDCl$_3$, δ): (E) and (Z) mixture 1.48–2.54 (7H, m), 2.77–3.16 (1H, m), 5.62–5.85 (1H, m), 6.59–7.35 (4H, m), 7.41–7.50 (3H, m), 7.58–7.64 (2H, m), 7.80–7.96 (1H, m), 8.40 and 8.51 (1H, 1:1.6, d, J=6.8 Hz); (+)-APCI/MS: 399 (M$^+$+1).

EXAMPLE 89

3-[2-(2-Hydroxyiminocyclohexyl)-3-oxo-2,3-dihydropyridazin-6-yl]-2-phenylpyrazolo[1,5-a]pyridine mp: 238–240° C. (EtOH-H$_2$O); IR (Nujol): 1650, 1580, 1530 cm$^{-1}$; NMR (DMSO-d$_6$, δ): 1.19–1.40 (1H, m), 1.58–2.30 (6H, m), 3.03–3.23 (1H, m), 5.42–5.56 (1H, m), 6.91 (1H, d, J=9.6 Hz), 7.10 (1H, d, J=6.7 Hz), 7.22 (1H, d, J=9.6 Hz), 7.41–7.57 (6H, m), 7.85 (1H, d, J=8.8 Hz), 8.76 (1H, d, J=6.7 Hz); (+)-APCI/MS: 400 (M$^+$+1); Analysis Calcd. for C$_{23}$H$_{21}$N$_5$O$_2$.0.2H$_2$O: C, 68.54, H, 5.35, N, 17.38; Found: C, 68.67, H, 5.47, N, 17.28.

EXAMPLE 90

3-[2-{2-(Methoxyimino)cyclohexyl}-3-oxo-2,3-dihydropyridazin-6-yl]-2-phenylpyrazolo[1,5-a]pyridine mp: 85–87° C. (Et$_2$O); IR (Nujol): 1670, 1635, 1600 cm$^{-1}$; NMR (CDCl$_3$, δ): 1.42–2.16 (7H, m), 2.33–2.55 (1H, m), 3.27 (1H, dm, J=15.4 Hz), 3.53 (3H, s), 5.72 (1H, dd, J=11.0, 4.9 Hz), 5.78 (1H, d, J=9.6 Hz), 6.89 (1H, td, J=7.0 Hz, 1.4 Hz), 7.00 (1H, d, J=9.6 Hz), 7.26 (1H, dd, J=8.9, 7.0 Hz), 7.42–7.47 (3H, m), 7.60–7.84 (2H, m), 7.95 (1H, d, J=8.9 Hz), 8.52 (1H, d, J=7.0 Hz); (+)-APCI/MS: 414 (M$^+$+1); Analysis Calcd. for C$_{24}$H$_{23}$N$_5$O$_2$.0.2H$_2$O: C, 69.11, H, 5.65, N, 16.79; Found: C, 69.28, H, 5.80, N, 16.53.

EXAMPLE 91

3-[2-{2-(tert-Butoxycarbonylmethoxyimino)cyclohexyl}-3-oxo-2,3-dihydropyridazin-6-yl]-2-phenylpyrazolo[1,5-a]-pyridine IR (Film): 1745, 1660, 1570 cm$^{-1}$; NMR (CDCl$_3$, δ): 1.32 (9H, s), 1.43–2.46 (7H, m), 3.38 (1H, dm, J=15.1 Hz), 4.37 (2H, s), 5.71 (1H, dd, J=11.0, 4.8 Hz), 6.75 (1H, d, J=9.7 Hz), 6.88 (1H, t, J=6.9 Hz), 6.98 (1H, d, J=9.7 Hz), 7.31 (1H, dd, J=8.9, 6.9 Hz), 7.41–7.48 (3H, m), 7.60–7.65 (2H, m), 7.93 (1H, d, J=8.9 Hz), 8.51 (1H, d, J=6.9 Hz); (+)-APCI/MS: 514 (M$^+$+1).

EXAMPLE 92

3-[2-{2-Hydroxysulfonyloxyimino)cyclohexyl}-3-oxo-2,3-dihydropyridazin-6-yl]-2-phenylpyrazolo[1,5-a]pyridine mp: 230° C. (CH$_2$Cl$_2$-MeOH); NMR (DMSO-d$_6$, δ): 1.20–2.40 (6H, m), 2.80–3.00 (2H, m), 5.60 (1H, dd, J=10.0, 4.0 Hz), 6.89 (1H, d, J=9.6 Hz), 7.00–7.20 (2H, m), 7.36 (1H, m), 7.40–7.55 (3H, m), 7.55–7.70 (2H, m), 7.93 (1H, d, J=8.2 Hz), 8.78 (1H, d, J=6.1 Hz); (+)-APCI/MS: 480 (M+1).

EXAMPLE 93

To a stirred suspension of methyltriphenylphosphonium bromide (1.39 g) in tetrahydrofuran (30 ml) was added potassium tert-butoxide (437 mg) under nitrogen atmosphere at 0° C. After the mixture was stirred at 0–5° C. for 1.5 hours, to this was added a solution of 3-[2-(2-oxocyclohexyl)-3-oxo-2,3-dihydropyridazin-6-yl]-2-phenylpyrazolo[1,5-a]pyridine (500 mg) in tetrahydrofuran (10 ml). The mixture was stirred at room temperature for 4 hours and stood at room temperature overnight. Insoluble materials were filtered off and the filtrate was evaporated in vacuo. The residue was dissolved in dichloromethane (30 ml). The dichloromethane solution was washed with brine (20 ml), dried over anhydrous sodium sulfate, and evaporated in vacuo. The crude material was purified by column chromatography on silica gel using dichloromethane as an eluant to give colorless crystals of 3-[2-(2-methylenecyclohexyl)-3-oxo-2,3-dihydropyridazin-6-yl]-2-phenylpyrazolo[1,5-a]pyridine (186 mg).

mp: 229–230° C. (dec.) (EtOH); IR (Nujol): 1660, 1585, 1520 cm$^{-1}$; NMR (CDCl$_3$, δ): 1.40–1.72 (2H, m), 1.88–2.60 (6H, m), 4.19 (1H, s), 4.82 (1H, s), 5.58 (1H, dm, J=ca. 10 Hz), 6.80 (1H, d, J=9.6 Hz), 6.90 (1H, t, J=7.0 Hz), 7.02 (1H, d, J=9.6 Hz), 7.30 (1H, t, J=8.0 Hz), 7.44–7.48 (3H, m), 7.60–7.64 (2H, m), 7.97 (1H, d, J=8.0 Hz), 8.52 (1H d, J=7.0 Hz); (+)-APCI/MS: 383 (M$^+$+1); Analysis Calcd. for C$_{24}$H$_{22}$N$_4$O.1/4H$_2$O: C, 74.49, H, 5.86, N, 14.48; Found: C, 74.54, H, 5.73, N, 14.23.

EXAMPLE 94

To a solution of triethyl phosphonoacetate (374 mg) in tetrahydrofuran (3 ml) was added 60% sodium hydride in mineral oil (67 mg) at 5° C. After 5 minutes, to this was added a solution of 3-[2-(4-oxocyclohexyl)-3-oxo-2,3-dihydropyridazin-6-yl]-2-phenylpyrazolo[1,5-a]pyridine (533 mg) in a mixture of tetrahydrofuran (5 ml) and N,N-dimethylformamide (5 ml). The reaction mixture was warmed up to room temperature and allowed to stir for 3 hours. The solvent was evaporated in vacuo and the residue was partitioned between water (30 ml) and ethyl acetate (40 ml). After an additional extraction with ethyl acetate (40 ml), the combined extracts were washed with saturated aqueous sodium bicarbonte (30 ml) and brine (30 ml), dried over anhydrous sodium sulfate, and evaporated in vacuo to give 0.74 g of crystals, which was purified by column chromatography on silica gel using a mixture of dichloromethane and ethyl acetate (10:1) to give colorless crystals of 3-[2-(4-ethoxycarbonylmethylenecyclohexyl)-3-oxo-2,3-dihydropyridazin-6-yl]-2-phenylpyrazolo[1,5-a]-pyridine (412 mg.

mp: 166–168° C. (EtOAc); IR (Nujol): 1700, 1650, 1580 cm$^{-1}$; NMR (CDCl$_3$, δ): 1.30 (3H, t, J=7.2 Hz), 1.44–1.70 (1H, m), 1.85–2.15 (4H, m), 2.53–2.81 (2H, m), 3.93 (1H, d, J=13.3 Hz), 4.17 (2H, q, J=7.2 Hz), 5.10–5.22 (1H, m), 5.76 (1H, s), 6.78 (1H, d, J=9.6 Hz), 6.93 (1H, t, J=6.9 Hz), 7.00 (1H, d, J=9.6 Hz), 7.33 (1H, dd, J=9.0 , 6.9 Hz), 7.44–7.47 (3H, m), 7.58–7.63 (2H, m), 7.92 (1H, d, J=9.0 Hz), 8.54 (1H, d, J=6.9 Hz); (+)-APCI/MS: 455 (M$^+$+1); Analysis Calcd. for C$_{27}$H$_{26}$N$_4$O$_3$: C, 71.35, H, 5.77, N, 12.33; Found: C, 71.10, H, 5.82, N, 12.26.

EXAMPLE 95

To a suspension of sodium hydride (44.2 g, 60% oil) in toluene (5.6 l) was added carefully tert-butyl (diethoxyphosphoryl)acetate (278.3 g) at 0° C. under nitrogen atmosphere. After being stirred for 30 minutes, to a reaction mixture was added by portions 3-[2-(2-oxocyclohexyl)-3-oxo-2,3-dihydropyridazin-6-yl]-2-phenylpyrazolo[1,5-a]pyridine (282.7 g), and which was stirred for additional 68 hours at ambient temperature. A reaction mixture was poured into ice-water (3 l) and organic layer was separated. Aqueous layer was reextracted with ethyl acetate (2 l). Organic layer was combined, washed In turn with water (2 l×3) and saturated sodium chloride in water, and dried over magnesium sulfate. Evaporation of the solvent gave a residue, which was chromatographed on silica gel (270–400 mesh, 7 Kg) eluting in turn with 9%, 17% and 33% ethyl acetate in toluene. Fractions containing another isomer were further purified under the same conditions (silica gel 1 kg). Fractions containing each of desired products were collected and concentrated in vacuo to give 3-[2-{2-(tert-butoxycarbonylmethyl)-1-cyclohexenyl}-3-oxo-2,3-dihydropyridazin-6-yl]-2-phenylpyrazolo-[1,5-a]pyridine (252.9 g), 3-[2-{2-(tert-butoxycarbonylmethyl)-2-cyclohexen-1-yl}-3-oxo-2,3-dihydropyridazin-6-yl]-2-phenylpyrazolo[1,5-a]pyridine (31.68 g) and (E)-3-[2-{2-(tert-butoxycarbonylmethylene)cyclohexyl}-3-oxo-2,3-dihydropyridazin-6-yl]-2-phenylpyrazolo[1,5-a]pyridine (16.08 g) respectively.

(1) 3-[2-{2-(tert-Butoxycarbonylmethyl)-1-cyclohexenyl}-3-oxo-2,3-dihydropyridazin-6-yl]-2-phenylpyrazolo[1,5-a]-pyridine Rf: 0.35 (CH$_2$Cl$_2$:EtOAc=10:1, 2 times); FT IR (KBr): 1727.9, 1668.1, 1635.3, 1592.9, 1529.3 cm$^{-1}$; NMR (CDCl$_3$, δ): 1.31 (9H, s), 1.70–2.00 (4H, m), 2.00–2.60 (4H, m), 2.80–3.00 (2H, m), 6.77 (1H, d, J=9.7 Hz), 6.85–6.94 (1H, m), 7.01 (1H, d, J=9.7 Hz), 7.25–7.35 (1H, m), 7.40–7.50 (3H, m), 7.61–7.67 (2H, m), 8.02 (1H, d, J=8.9 Hz), 8.51 (1H, d, J=7.0 Hz); (+)-APCI/IMS: 483 (M$^+$+1).

(2) 3-[2-{2-(tert-Butoxycarbonylmethyl)-2-cyclohexen-1-yl}-3-oxo-2,3-dihydropyridazin-6-yl]-2-phenylpyrazolo-[1,5-a]pyridine Rf: 0.52 (CH$_2$Cl$_2$:EtOAc=10:1, 2 times); mp: 145.5–147.0° C.; FT IR (KBr): 1726.0, 1668.1, 1631.5, 1592.9, 1523.5 cm$^{-1}$; NMR (CDCl$_3$, δ): 1.40 (9H, s), 1.60–2.30 (6H, m), 2.82 (2H, ABq, J=15.6, 15.5 Hz), 5.82 (1H, br s), 6.06 (1H, br s), 6.73 (1H, d, J=9.7 Hz), 6.85–6.94 (1H, m), 7.00 (1H, d, J=9.7 Hz), 7.20–7.65 (6H, m), 8.07 (1H, d, J=9.0 Hz), 8.51 (1H, d, J=6.9 Hz); (+)-APCI/MS: 483 (M$^+$+1); Analysis Calcd. for C$_{29}$H$_{30}$N$_4$O$_3$: C, 72.18, H, 6.27, N, 11.61; Found: C, 72.13, H, 6.51, N, 11.58.

(3) (E)-3-[2-{2-(tert-Butoxycarbonylmethylene)-cyclohexyl}-3-oxo-2,3-dihydropyridazin-6-yl]-2-phenylpyrazolo[1,5-a]pyridine Rf: 0.65 (CH$_2$Cl$_2$:EtoAc 10:1, 2 times); mp: 110–116° C.; FT IR (KBr): 1712.5, 1666.2, 1592.9, 1531.2 cm$^{-1}$; NMR (CDCl$_3$, δ): 1.42 (9H, s), 1.45–2.50 (7H, m), 4.00–4.15 (1H, m), 5.05 (1H, s), 5.65 (1H, dd, J=11.8, 3.1 Hz), 6.81 (1H, d, J=9.6 Hz), 6.86–6.95 (1H, m), 7.03 (1H, d, J=9.6 Hz), 7.10–7.65 (6H, m), 7.89 (1H, d, J=8.9 Hz), 8.53 (1H, d, J=6.9 Hz); (+)-APCI/MS: 483 (M$^+$+1); Analysis Calcd. for C$_{29}$H$_{30}$N$_4$O$_3$.2/3Toluene: C, 74.33, H, 6.55, N, 10.30; Found: C, 74.26, H, 6.49, N, 10.58.

EXAMPLE 96

To a suspension of sodium hydride (820 mg, 60% Oil) in tetrahydrofuran (100 ml) was added dropwise (diethoxyphosphoryl)acetonitrile (1.74 ml) at 50° C. under nitrogen atmosphere. After stirred for 20 minutes, to a reaction mixture was added by portions 3-[2-(2-oxocyclohexyl)-3-oxo-2,3-dihydropyridazin-6-yl]-2-phenylpyrazolo[1,5-a]pyridine (6 g), and the mixture was stirred for additional 5 hours. The reaction mixture was cooled to room temperature, added carefully water (10 ml) thereto and poured into a mixture of ethyl acetate (500 ml) and n-hexane (150 ml). The resultant was washed in. turn with water (100 ml×3) and saturated sodium chloride in water (100 ml×2), and dried over magnesium sulfate. Evaporation of the solvent gave a residue, which was chromatographed on silica gel eluting in turn with 3% and 5% ethyl acetate in dichloromethane. The former fraction contained (E)-isomer, which was recrystallized from ethanol (342 mg), and the latter fraction contained (Z)-isomer, which was recrystallized from a mixture of diisopropyl ether and ethanol (237 mg).

(E)-isomer (E)-3-[2-{2-Cyanomethylenecyclohexyl}-3-oxo-2,3-dihydropyridazin-6-yl]-2-phenylpyrazolo[1,5-a]pyridine mp: 174.0–175.0° C. (CH$_2$Cl$_2$-n-hexane); FT IR (KBr): 2215.8, 1664.3, 1591.0, 1531.2 cm$^{-1}$; NMR (DMSO-d$_6$, δ): 1.10–1.50 (1H, m), 1.60–2.15 (5H, m), 2.30–2.50 (1H, m), 2.80–3.00 (1H, m), 4.97 (1H, s), 5.40–5.60 (1H, m), 6.96 (1H, d, J=9.7 Hz), 7.04–7.12 (1H, m), 7.21 (1H, d, J=9.7 Hz), 7.40–7.69 (6H, m), 7.85 (1H, d, J=8.9 Hz), 8.83 (1H, d, J=6.9 Hz); (+)-APCI/MS: 408 (M$^+$+1); Analysis Calcd. for C$_{25}$H$_{21}$N$_5$O: C, 73.69, H, 5.19, N, 17.19; Found: C, 73.65, H, 5.31, N, 17.08.

(Z)-isomer (Z)-3-[2-{2-Cyanomethylenecyclohexyl}-3-oxo-2,3-dihydropyridazin-6-yl]-2-phenylpyrazolo[1,5-a]pyridine mp: 70.0–72.0° C.; FT IR (KBr): 2235.0, 1662.3, 1591.0, 1529.3 cm$^{-1}$; NMR (DMSO-d$_6$, δ): 1.50–2.20 (6H, m), 3.18 (2H, s), 5.50–5.65 (1H, m), 6.18 (1H, br s), 6.98–7.12 (2H, m), 7.39–7.65 (6H, m), 7.88 (1H, d, J=8.9 Hz), 8.82 (1H, d, J=6.9 Hz); (+)-APCI/MS: 408 (M$^+$+1).

EXAMPLE 97

(E)-3-[2-{2-(4,4,6-Trimethyl-5,6-dihydro-4H-1,3-oxazin-2-yl)methylenecyclohexyl}-3-oxo-2,3-dihydropyridazin-6-yl]-2-phenylpyrazolo[1,5-a]pyridine and (Z)-3-[2-{2-(4,4,6-trimethyl-5,6-dihydro-4H-1,3-oxazin-2-yl)methylenecyclohexyl}-3-oxo-2,3-dihydropyridazin-6-yl]-2-phenylpyrazolo[1,5-a]pyridine were obtained in substantially the same manner as that of Example 96.

(1) E-Isomer mp: 156.0–158.0° C. (CH$_2$Cl$_2$-n-hexane); FT IR (KBr): 1662.3, 1589.1, 1527.3 cm$^{-1}$; NMR (DMSO-$_6$, δ): 1.10 (3H, s), 1.04 (3H, s), 1.09 (3H, d, J=7.1 Hz), 1.0–1.8 (8H, m), 2.10–2.25 (2H, m), 4.0–4.1 (1H, m), 5.71 (1H, s), 6.14 (1H, m) 6.90 (1H, d, J=9.6 Hz), 7.01–7.08 (1H, m), 7.18 (1H, d, J=9.6 Hz), 7.36–7.60 (6H, m), 7.72 (1H, d, J=8.9 Hz), 8.81 (1H, d, J=6.9 Hz); (+)-APCI/MS: 508 (M$^+$+1); Analysis Calcd. for $C_{31}H_{33}N_5O_2 \cdot 1/3H_2O$: C, 72.49, H, 6.54, N, 13.63; Found: C, 72.60, H, 6.49, N, 13.70.

(2) (Z)-isomer

FT IR (KBr): 1662.3, 1591.0, 1531.2 cm$^{-1}$; NMR (DMSO-d$_6$, δ): 0.95 (3H, s), 1.05 (3H, s), 1.10–1.90 (1H, m), 2.05–2.25 (2H, m), 4.0–4.1 (1H, m), 5.70 (1H, br s), 6.15–6.28 (1H, m), 6.89 (1H, d, J=9.6 Hz), 7.00–7.08 (1H, m), 7.16 (1H, d, J=9.6 Hz), 7.30–7.60 (6H, m), 7.73 (1H, d, J=8.8 Hz), 8.81 (1H, d, J=6.8 Hz); (+)-APCI/MS: 508 (M$^+$+1).

EXAMPLE 98

To a solution of tert-butyl 2-(diethoxyphosphoryl)-acetate (1.08 g) in toluene (22 ml) was added potassium tert-butoxide (480 mg) and 18-crown-6 (75.5 mg) at 5° C. The reaction mixture was allowed to stir at room temperature for 15.5 hours. Then, it was washed with water (25 ml). After the aqueous layer was extracted with ethyl acetate (20 ml), the combined extracts were washed with brine (20 ml), dried over anhydrous magnesium sulfate, and evaporated in vacuo. The crude material was purified by silica gel column chromatography using a mixture of toluene and ethyl acetate (10:1) to give pale yellow crystals of (Z)-3-[2-{2-(tert-butoxycarbonyl-methylene)cyclohexyl}-3-oxo-2,3-dihydropyridazin-6-yl]-2-phenylpyrazolo[1,5-a]pyridine (487 mg).

mp: 171–172° C. (EtOAc); IR (Nujol): 1705, 1660, 1635, 1595, 1530 cm$^{-1}$; NMR (CDCl$_3$, δ): 1.42 (9H, s), 1.53–1.93 (4H, m), 2.23–2.46 (3H, m), 2.67–2.91 (1H, m), 5.85 (1H, s), 6.43 (1H, t, J=4.2 Hz), 6.79 (1H, d, J=9.6 Hz), 6.88 (1H, td, J=7.0, 1.3 Hz), 7.02 (1H, d, J=9.6 Hz), 7.26 (1H, dd, J=9.0, 7.0 Hz), 7.41–7.45 (3H, m), 7.57–7.63 (2H, m), 7.81 (1H, d, J=9.0 Hz), 8.51 (1H, d, J=7.0 Hz); Analysis Calcd. for $C_{29}H_{30}N_4O_3$: C, 72.18, H, 6.27, N, 11.61; Found: C, 71.93, H, 6.51, N, 11.59.

EXAMPLE 99

A mixture of 3-acetyl-2-phenylpyrazolo[1,5-a]pyridine (2.5 g), glyoxylic acid monohydrate (5 g), and 1,2-dimethoxy ethane (125 ml) was refluxed for 5 hours. Solvent was removed in vacuo and the residue was partitioned between ethyl acetate and water. The organic layer was washed with water, dried over anhydrous sodium sulfate, and evaporated in vacuo. To the residue was added 28% aqueous ammonia (10 ml) and phenylhydrazine hydrochloride (1.92 g). The mixture was refluxed for 6 hours. After being cooled to room temperature, the mixture was partitioned between water and ethyl acetate. The organic layer was washed with water, dried over anhydrous sodium sulfate, and evaporated in vacuo. The crude material was purified by column chromatography on, silica gel using a mixture of n-hexane and ethyl acetate (10:1) as an eluant to give yellow crystals of 3-(2-phenyl-3-oxo-2,3-dihydropyridazin-6-yl)- 2-phenylpyrazolo[1,5-a]pyridine (250 mg)

mp: 170° C. (EtOAc); IR (Nujol): 1640, 1600, 1585 cm$^{-1}$; NMR (CDCl$_3$, δ): 6.80–6.99 (4H, m), 7.17–7.25 (4H, m), 7.33–7.43 (5H, m), 7.77–7.82 (2H, m), 8.54 (1H, d, J=7.0 Hz).

The following compounds (Examples 100 and 101) were obtained according to a similar manner to that of Example 99.

EXAMPLE 100

3-[2-(4-Methoxyphenyl)-3-oxo-2,3-dihydropyridazin-6-yl]-2-phenylpyrazolo[1,5-a]pyridine mp: 158° C. (Et$_2$O); IR (Nujol): 1630, 1615, 1600, 1580, 1530 cm$^{-1}$; NMR (CDCl$_3$, δ): 3.75 (3H, s), 6.77–6.94 (3H, m), 6.91 (1H, d, J=9.1 Hz), 7.22 (1H, t, J=6.8 Hz), 7.33–7.43 (6H, m), 7.77–7.82 (2H, m), 8.54 (1H, d, J=7.0 Hz).

EXAMPLE 101

3-[2-(2-Methoxyphenyl)-3-oxo-2,3-dihydropyridazin-6-yl]-2-phenylpyrazolo[1,5-a]pyridine mp: 163° C. (n-hexane-EtOAc); IR (Nujol): 1620, 1595 cm$^{-1}$; NMR (CDCl$_3$, δ): 3.92 (3H, s), 6.83–7.19 (4H, m), 7.19–7.26 (1H, m), 7.42–7.56 (5H, m), 7.68–7.72 (3H, m), 8.15 (1H, d, J=9.0 Hz), 8.47 (1H, d, J=7.0 Hz).

EXAMPLE 102

To a solution of oxalyl chloride (160 μl) in dichloromethane (10 ml) was added dropwise in turn with dimethyl sulfoxide (210 μl), a solution of 3-[2-(3-hydroxycyclohexyl)-3-oxo-2,3-dihydropyridazin-6-yl]-2-phenylpyrazolo[1,5-a]pyridine (366 mg) in dichloromethane (10 ml) and triethylamine (663 μl) at −70° C. under nitrogen atmosphere. A reaction mixture was allowed to warm to ambient temperature and diluted with ethyl acetate (100 ml), which was washed in turn with 1N-aqueous hydrochloric acid (50 ml×2), brine (50 ml), saturated sodium hydrogen carbonate in water (50 ml) and brine (50 ml×2), and dried over magnesium sulfate. Evaporation of the solvent gave a residue, which was chromatographed on silica gel eluting in turn with 30% and 50% ethyl acetate in dichloromethane. Fractions containing desired product were combined and concentrated in vacuo to give solid, which was recrystallized from ethanol to give 3-[2-(3-oxocyclohexyl)-3-oxo-2,3-dihydropyridazin-6-yl]-2-phenylpyrazolo[1,5-a]pyridine (310 mg).

mp: 126–127° C.; FT IR (KBr): 1712.5, 1660.4, 1633.4, 1591.0, 1531.2 cm$^{-1}$; NMR (CDCl$_3$, δ): 1.70–2.60 (6H, m), 2.65–2.80 (1H, m), 2.90–3.03 (1H, m), 5.40–5.50 (1H, m), 6.81 (1H, d, J=9.6 Hz), 6.96 (1H, t, J=6.7 Hz), 7.05 (1H, d, J=9.6 Hz), 7.30–7.65 (6H, m), 7.86 (1H, d, J=8.9 Hz), 8.60 (1H, d, J=6.9 Hz); (+)-APCI/MS: 385 (M$^+$+1); Analysis Calcd. for $C_{23}H_{20}N_4O_2 \cdot 0.5H_2O$: C, 70.21, H, 5.38, N, 14.24; Found: C, 70.58, H, 5.51, N, 13.90.

EXAMPLE 103

A mixture of 3-[2-(4,4-ethylenedioxycyclohexyl)-3-oxo-2,3-dihydropyridazin-6-yl]-2-phenylpyrazolo[1,5-a]pyridine (0.68 g), 1N hydrochloric acid (5 ml), and dioxane (10 ml) was stirred at room temperature for 1 hour and heated at 50° C. for 2 hours. The reaction mixture was poured into 50 ml of water and the mixture was extracted with ethyl acetate (20 ml×2). The combined extracts were sequencially washed with saturated aqueous sodium bicarbonate (30 ml) and brine (30 ml), dried over anhydrous sodium sulfate. Evaporation of the solvent gave yellow crystals of 3-[2-(4-oxocyclohexyl)-3-oxo-2,3-dihydropyr4cazin-6-yl]-2-phenylpyrazolo[1,5-a]pyridine (610 mg).

mp: 138–140° C. (EtOAc); IR (Nujol): 1700, 1650, 1580, 1515 cm$^{-1}$; NMR (CDCl$_3$, δ): 1.85 (1H, m), 2.05–2.44 (5H, m), 2.72 (1H, dd, J=14.3, 5.0 Hz), 2.97 (1H, dd, J=14.3, 10.6 Hz), 5.38–5.50 (1H, m), 6.80 (1H, d, J=9.6 Hz), 6.97 (1H, t, J=7.0 Hz), 7.05 (1H, d, J=9.6 Hz), 7.34 (1H, t, J=8.0 Hz), 7.44–7.48 (3H, m), 7.57–7.62 (2H, m), 7.85 (1H, d, J=8.0 Hz), 8.54 i1H, d, J=7.0 Hz); (+)-APCI/MS: 385 (M$^+$+1).

EXAMPLE 104

A solution of 3-[2-{3-(tert-butyldimethylsilyloxy)cyclohexyl}-3-oxo-2,3-dihydropyridazin-6-yl]-2-phenylpyrazolo[1,5-a]pyridine (570 mg) and 70% aqueous tetrabutylammonium fluoride (4.3 g) in tetrahydrofuran (10 ml) was stirred for overnight at room temperature. A reaction mixture was diluted with ethyl acetate (100 ml), which was washed in turn with water (50 ml×4) and saturated sodium chloride in water (50 ml×2), and dried over magnesium sulfate. Evaporation of the solvent gave a residue, which was chromatographed on silica gel (40 ml) eluting in turn with 30%, 50% ethyl acetate in dichloromethane and ethyl acetate. Fractions containing desired product were concentrated under reduced pressure to give residue, which was recrystallized from ethanol to give 3-[2-(3-hydroxycyclohexyl)-3-oxo-2,3-dihydropyridazin-6-yl]-2-phenylpyrazolo[1,5-a]pyridine (430 mg).

mp: 117–118° C.; FT IR (KBr): 3380.0, 1658.5, 1587.1, 1531.2 cm$^{-1}$; NMR (CDCl$_3$, δ): 1.20–2.40 (8H, m), 3.80–4.00 (1H, m), 5.00–5.20 (1H, m), 6.79 (1H, d, J=9.6 Hz), 6.90–7.00 (1H, m), 7.02 (1H, d, J=9.6 Hz), 7.30–7.40 (1H, m), 7.40–7.50 (3H, m), 7.55–7.70 (2H, m), 7.95 (1H, d, J=8.9 Hz), 8.57 (1H, d, J=6.9 Hz); (+)-APCI/MS: 387 (M$^+$+1); Analysis Calcd. for C$_{23}$H$_{22}$N$_4$O$_2$.3/4H$_2$O: C, 69.07, H, 5.92, N, 14.01; Found: C, 68.98, H, 6.02, N, 13.61.

EXAMPLE 105

To a solution on of 3-[2-(2-carboxymethyl-1-cyclohexenyl)-3-oxo-2,3-dihydropyridazin-6-yl]-2-phenylpyrazolo[1,5-a]pyridine (2.07 g) in tetrahydrofuran (40 ml) was added dropwise under nitrogen atmosphere a solution of borane-tetrahydrofuran complex in tetrahydrofuran (1M solution, 9.72 ml) at −100° C. over a period of 10 minutes. The reaction mixture was allowed to stir at room temperature for 5.5 hours. Then, the mixture was cooled to 10° C. in an ice bath and treated with 1N hydrochloric acid. The organic layer was separated and the aqueous layer was extracted with dichloromethane. The combined extracts were washed with 1N aqueous sodium hydroxide solution, water, and brine, dried over anhydrous magnesium sulfate, and concentrated in vacuo. The crude material was purified by column chromatography on silica gel (toluene:MeOH=10:1) to give colorless crystals of: 3-[2-{2-(2-hydroxyethyl)-1-cyclohexenyl}-3-oxo-2,3-dihydropyridazin-6-yl]-2-phenylpyrazolo[1,5-a]pyridine (1.14 g).

mp: 198–199° C. (aq. EtOH); IR (Nujol): 3375, 1650, 1630, 1585, 1520 cm$^{-1}$; NMR (CDCl$_3$, δ): 1.66–1.97 (4H, m), 2.01–2.24 (2H, m), 2.33–2.47 (4H, m), 3.23 (1H, t, J=5.4 Hz), 3.63–3.83 (2H, m), 6.85 (1H, d, J=9.7 Hz), 6.92 (1H, t, J=6.9 Hz), 7.08 (1H, d, J=9.7 Hz), 7.32 (1H, dd, J=8.9, 6.9 Hz), 7.45–7.50 (3H, m), 7.60–7.65 (2H, m), 7.91 (1H, d, J=8.9 Hz), 8.53 (1H, d, J=6.9 Hz); Analysis Calcd. for C$_{25}$H$_{24}$N$_4$O$_2$.0.2H$_2$O: C, 72.16, H, 5.91, N, 13.46; Found: C, 72.11, H, 5.90, N, 13.48.

EXAMPLE 106

To a solution of 3-[2-(2-carboxymethyl-1-cyclohexenyl)-3-oxo-2,3-dihydropyridazin-6-yl]-2-phenylpyrazolo[1,5-a]pyridine (2 g) in dichloromethane (20 ml) was added in turn 2,2-dimethyl-1,3-dioxane-4,6-dione (750 mg), 1,3-dicyclohexylcarbodiimide (1.1 g) and 4-dimethylaminopyridine (720 mg) at 0° C. A reaction mixture was allowed to warm to ambient temperature and stirred for overnight. Precipitate was removed by filtration, and mother liquor was washed with 1N-aqueous hydrochloric acid and dried over magnesium sulfate. Evaporation of the solvent gave a residue, which was dissolved in a mixture of acetic acid (15 ml) and water (15 ml), and which was. refluxed for 10 hours. A reaction mixture was extracted with ethyl acetate (200 ml) and organic layer was separated, which was neutralized with saturated sodium hydrogen carbonate in water. Organic phase was separated, washed in turn with saturated sodium hydrogen carbonate in water (50 ml) and brine (50 ml×2), and dried over magnesium sulfate. Evaporation of the solvent gave a residue, which was chromatographed on silica gel (100 g) eluting in turn with 33%, 50%, 80% ethyl acetate in n-hexane and ethyl acetate to give 3-[2-{2-(2-oxopropyl)- 1-cyclohexenyl}-3-oxo-2,3-dihydropyridazin-6-yl]-2-phenylpyrazolo[1,5-a]pyridine (0.5 g).

FT IR (KBr): 1712.5, 1666.2, 1633.4, 1592.9, 1529.3 cm$^{-1}$; NMR (CDCl$_3$, δ): 1.70–2.00 (4H, m), 2.08 (3H, s), 2.20–2.60 (4H, m), 3.04 (2H, s), 6.79 (1H, d, J=9.7 Hz), 6.88–6.96 (1H, m), 7.04 (1H, d, J=9.7 Hz), 7.28–7.37 (1H, m), 7.45–7.47 (3H, m), 7.60–7.70 (2H, m), 7.93 (1H, d, J=8.9 Hz), 8.52 (1H, d, J=6.9 Hz); (+)-APCI/MS: 425 (M$^+$+1).

EXAMPLE 107

To a solution of lithium bis(trimethylsilyl) amide (20.5 ml, 1.0 Mol solution in hexane) in tetrahydrofuran (50 ml) was added dropwise ethyl acetate (2.05 ml) at −70° C. under nitrogen atmosphere. After stirred for one hour, to a reaction mixture was added carefully a solution of 3-[2-(2-oxocyclohexyl)-3-oxo-2,3-dihydropyridazin-6-yl]-2-phenylpyrazolo[1,5-a]pyridine (3.85 g) in tetrahydrofuran (40 ml), and the reaction mixture was stirred at −70° C. for. an additional one hour. The reaction mixture was allowed to warm at room temperature, added in turn with 6N-aqueous hydrochloric acid (20 ml) and brine (50 ml). The resulting solution was poured into ethyl acetate (400 ml) and organic layer was separated, which was washed two times with brine (50 ml) and dried over magnesium sulfate. Evaporation of the solvent gave a residue, which was chromatographed on silica gel (250 ml) eluting with 40% ethyl acetate in n-hexane. Fractions. containing desired product were collected. Evaporation of the solvent gave a residue, which was recrystallized from a mixture of dichloromethane and n-hexane to give cis-3-[2-(2-ethoxycarbonylmethyl-2-hydroxycyclohexyl)-3-oxo-2,3-dihydropyridazin-6-yl]-2-phenylpyrazolo[1,5-a]pyridine (3.0 g).

mp: 181.3–182.0° C.; FT IR (KBr): 1708.6, 1666.2, 1592.9, 1529.3 cm$^{-1}$; NMR (DMSO-d$_6$, δ): 1.11 (3H, t, J=7.1 Hz), 1.30–1.95 (7H, m), 2.20–2.45 (1H, m), 2.41 (2H, s), 3.85–4.10 (2H, m), 4.63 (1H, br s), 4.85–5.05 (1H, m), 6.88 (1H, d, J=9.6 Hz), 7.04–7.12 (2H, m), 7.40–7.70 (6H, m), 8.08 (1H, d, J=8.9 Hz), 8.84 (1H, d, J=6.9 Hz).

EXAMPLE 108

To a solution of 3-[2-(2-oxocyclohexyl)-3-oxo-2,3-dihydropyridazin-6-yl]-2-phenylpyrazolo[1,5-a]pyridine (384 mg) and tosylmethyl isocyanide (430 mg) in 1,2-dimethoxyethane (4 ml) was added dropwise a solution of potassium tert-butoxide (448 mg) in a mixture of 1,2-dimethoxyethane and tert-butanol (1:1, 2 ml) at 0° C. The reaction mixture was stirred at 0° C. for 1 hour and at room temperature for 30 minutes. Then, it was partitioned between water and ethyl acetate. The organic layer was washed with brine, dried over anhydrous sodium sulfate, and evaporated in vacuo. The crude product was crystallized from diethyl ether to give yellow crystals of 3-[2-(2- cyanocyclohexyl)-3-oxo-2,3-dihydropyridazin-6-yl]-2-phenylpyrazolo[1,5-a]pyridine (0.12 g).

mp: 214° C.; IR (Nujol): 2125, 1660, 1655, 1625, 1585, 1520 cm$^{-1}$; NMR (CDCl$_3$, δ): 1.80–2.00 (4H, m), 2.30–2.50 (4H, m), 5.10 (1H, m), 5.74 (1H, m), 6.68 (1H, d, J=9.7 Hz), 6.70 (1H, t, J=6.9 Hz), 7.02 (1H, d, J=9.7 Hz), 7.24–7.28 (1H, m), 7.40–7.70 (3H, m), 7.70–7.90 (2H, m), 8.20 (1H, d, J=8.9 Hz), 8.56 (1H, d, J=6.9 Hz); (+)-APCI/MS: 396 (M$^+$+1).

EXAMPLE 109

A mixture of 3-[2-(2-cyanocyclohexyl)-3-oxo-2,3-dihydropyridazin-6-yl]-2-phenylpyrazolo[1,5-a]pyridine (130 mg) and conc. sulfuric acid (1.5 ml) was stirred at room temperature for 45 minutes. Then, the mixture was cooled in an ice-bath and treated with saturated aqueous sodium bicarbonate to make pH of the mixture to 2.0. The mixture was extracted with a mixture of ethyl acetate and tetrahydrofuran. The organic extract was dried over anhydrous sodium sulfate and evaporated in vacuo. The crude product was crystallized from diethyl ether to give colorless crystals of 3-[2-(2-carboxycyclohexyl)-3-oxo-2,3-dihydropyridazin-6-yl]-2-phenylpyrazolo[1,5-a]pyridine (0.10 g).

mp: 164° C.; IR (Nujol): 1690, 1650, 1630, 1580, 1520 cm$^{-1}$; NMR (CDCl$_3$, δ): 1.30–2.60 (8H, m), 5.15 (1H, m), 5.60 (1H, m), 6.52 (1H, d, J=9.7 Hz), 6.90–7.10 (2H, m), 7.20–7.90 (6H, m), 8.35 (1H, d, J=8.9 Hz), 8.60 (1H, d, J=6.9 Hz); (+)-APCI/MS: 415 (M$^+$+1).

EXAMPLE 110

To a solution of 3-[2-(2-carbamoylmethyl-1-cyclohexenyl)-3-oxo-2,3-dihydropyridazin-6-yl]-2-phenylpyrazolo[1,5-a]pyridine (2.15 g) and pyridine (2.1 ml) in dichloromethane (25 ml) was added dropwise trifluoroacetic anhydride (1.1 ml) at 0° C. under nitrogen atmosphere. The reaction mixture was allowed to warm to room temperature and stirred for 3 hours. The resultant was poured into ethyl acetate (500 ml), washed in turn with water (100 ml×2), saturated sodium hydrogen carbonate in water (50 ml×2), 1N-aqueous hydrochloric acid (50 ml×2), brine (100 ml), saturated sodium hydrogen carbonate in water (50 ml×2) and brine (100 ml×2), and dried over magnesium sulfate. Evaporation of the solvent gave a residue, which was chromatographed on silica gel (200 ml) eluting in turn with 3% and 5% ethyl acetate in dichloromethane. Fractions containing desired product were collected. Evaporation of the solvent gave a residue, which was recrystallized from a mixture of dichloromethane and n-hexane to give 3-[2-(2-cyanomethyl-1-cyclohexenyl-3-oxo-2,3-dihydropyridazin-6-yl]-2-phenylpyrazolo[1.5-a]pyridine (1.28 g).

mp: 74.0–76.0° C.; FT IR (KBr): 2250.5, 1733.7, 1670.1, 1633.4, 1594.8, 1529.3 cm$^{-1}$; NMR (DMSO-d$_6$, δ): 1.60–1.85 (4H, m), 2.05–2.40 (4H, m), 3.26 (2H, s), 6.94 (1H, d, J=9.7 Hz), 7.04–7.17 (2H, m), 7.38–7.69 (6H, m), 7.87 (1H, d, J=8.9 Hz), 8.83 (1H; d, J=6.9 Hz); (+)-APCI/MS: 408 (M$^+$+1); Analysis Calcd. for C$_{25}$H$_{21}$N$_5$O$_1$.1/2H$_2$O: C, 72.10, H, 5.32, N, 16.82; Found: C, 72.03, H, 5.13, N, 16.54.

EXAMPLE 111

A mixture of 3-[2-(2-cyanomethyl-1-cyclohexenyl)-3-oxo-2,3-dihydropyridazin-6-yl]-2-phenylpyrazolo[1,5-a]-pyridine (1 g), sodium azide (480 mg) and ammonium chloride (200 mg) in 1-methyl-2-pyrrolidone (10 ml) was heated at 140 to 150° C. for 6 hours with stirring. The reaction mixture was cooled to room temperature, which was poured into water and adjusted to pH 1.0 with 1N-aqueous hydrochloric acid. The resulting solution was extracted three times with ethyl acetate (100 ml). organic layers were combined, washed with brine (50 ml×2) and dried over magnesium sulfate. Evaporation of the solvent gave a residue, which was chromatographed on silica gel eluting in turn with 2%, 3%, 5%, 10% methanol in dichloromethane. Fractions containing desired product were collected. Evaporation of the solvent gave a residue which was recrystallized from ethyl acetate to give 3-[2-{2-(1H-tetrazol-5-yl)methylenecyclohexyl}-3-oxo-2,3-dihydropyridazin-6-yl]-2-phenylpyrazolo[1,5-a]pyridine (85 mg).

mp: 129–131° C.; FT IR (KBr): 1654.6, 1585, 1529.3 cm$^{-1}$; NMR (DMSO-d$_6$, δ): 1.50–2.20 (6H, m), 5.51 (1H, br s), 5.96 (1H, s), 6.83 (1H, d, J=9.7 Hz), 7.01–7.11 (2H, m), 7.39–7.70 (6H, m), 7.90 (1H, d, J=8.9 Hz), 8.82 (1H, d, J=6.9 Hz); (+)-APCI/MS: 451 (M$^+$+1).

EXAMPLE 112

To a solution of 3-[2-{2-(piperazin-1-ylcarbonyl)-methyl-1-cyclohexenyl}-3-oxo-2,3-dihydropyridazin-6-yl]-2-phenylpyrazolo[1,5-a]pyridine (500 mg) and pyridine (123 μl) in dichloromethane (10 ml) was added acetyl chloride (79 μl) at room temperature, and stirred for 30 minutes. The reaction mixture was poured into a mixture of dichloromethane (80 ml) and brine (30 ml), and organic layer was separated, which was dried over magnesium sulfate. Evaporation of the solvent gave a residue, which was chromatographed on silica gel (40 ml) eluting with 5% methanol in dichloromethane. Fractions containing desired product were collected, and solvent was removed under reduced pressure to give 3-[2-{2-(4-acetylpiperazin-1-ylcarbonyl)methyl-1-cyclohexenyl}-3-oxo-2,3-dihydropyridazin-6-yl]-2-phenylpyrazolo[1,5-a]pyridine (0.49 g).

FT IR (KBr): 1662.3, 1635.3, 1591.0, 1527.3 cm$^{-1}$; NMR (CDCl$_3$, δ): 1.60–2.60 (8H, m), 2.03 (3H, s), 3.00–3.70 (8H, m), 6.78 (1H, d, J=9.7 Hz), 6.90–7.00 (1H, m), 7.07 (1H, d, J=9.7 Hz) 7.25–7.70 (6H, m), 7.90–8.10 (1H, m), 8.54 (1H, d, J=6.9 Hz); (+)-APCI/MS: 537 (M$^+$+1).

EXAMPLE 113

The mixture of 3-[2-{2-(4-triphenylmethylpiperazin-1-ylcarbonyl)methyl-1-cyclohexenyl}-3-oxo-2,3-dihydropyridazin-6-yl]-2-phenylpyrazolo[1,5-a]pyridine (4.2 g), formic acid (10 ml) and concentrated hydrochloric acid (1.43 ml) was stirred for 2 hours at room temperature. The reaction mixture was poured into a mixture of ethyl acetate (200 ml) and water (100 ml). Aqueous layer was separated, and the pH was adjusted to pH 12.0 with 4N-aqueous sodium hydroxide solution, which was extracted with dichloromethane (300 ml and 150 ml). Organic phase was combined and dried over magnesium sulfate. Evaporation of the solvent gave a residue, which was chromatographed on silica gel eluting in turn with 5% and 10% methanol in dichloromethane. Fractions containing desired product were collected, and solvent was removed under reduced pressure to give solid, which was recrystallized from ethyl acetate to give 3-[2-{2-(piperazin-1-ylcarbonyl)methyl-1-cyclohexenyl}-3-oxo-2,3-dihydropyridazin-6-yl]-2-phenylpyrazolo[1,5-a]pyridine (2.2 g).

mp: 208.5–209.0° C.; FT IR (KBr): 1662.3, 1637.3, 1587.1, 1529.3 cm$^{-1}$; NMR (CDCl$_3$, δ): 1.70–2.00 (4H, m), 2.20–2.60 (4H, m), 2.70–2.80 (4H, m), 3.10 (2H, s), 3.30–3.70 (4H, m), 6.77 (1H, d, J=9.7 Hz), 6.89–6.96-(1H, m), 7.04 (1H, d, J=9.7 Hz), 7.30–7.40 (1H, m), 7.45–7.70 (5H, m), 8.00 (1H, d, J=8.9 Hz), 8.52 (1H, d, J=6.9 Hz); (+)-APCI/MS: 495 (M$^+$+1).

EXAMPLE 114

To a solution of 3-[2-(1-tert-butoxycarbonyl-4-oxopiperidin-3-yl)-3-oxo-2,3-dihydropyridazin-6-yl]-2-phenylpyrazolo[1,5-a]pyridine (500 mg) in dichloromethane (10 ml) was added trifluoroacetic acid (5 ml) at room temperature, and stirred for 2 hours. Solvent was evaporated and removed by toluene azeotrope to give residue, which was chromatographed on silica gel eluting in turn with 5% and 10% methanol in dichloromethane. Fractions containing desired product were collected and concentrated in vacuo to give residue, which was dissolved in methanol and passed through Amberlite IRA-910 (10ml). eluting with methanol. Solvent was removed under reduced pressure to give 3-[2-(4-oxopiperidin-3-yl)-3-oxo-2,3-dihydropyridazin-6-yl]-2-phenylpyrazolo[1,5-a]pyridine (0.3 g).

FT IR (KBr): 1724.0, 1660.4, 1589.1, 1529.3 cm$^{-1}$; NMR (CDCl$_3$, δ): 2.60–2.70 (2H, m), 2.99–3.14 (1H, m), 3.48–3.80 (3H, m), 5.71 (1H, dd, J=6.6, 10.9 Hz), 6.80 (1H, d, J=9.6 Hz), 6.90 (1H, t, J=6.9 Hz), 7.04 (1H, d, J=9.6 Hz), 7.24–7.33 (1H, m), 7.40–7.50 (3H, m), 7.60–7.65 (2H, m), 7.87 (1H, d, J=8.9 Hz), 8.52 (1H, d, J=6.9 Hz); (+)-APCI/MS: 386 (M$^+$+1).

EXAMPLE 115

3-[2-(3-Oxopiperidin-4-yl)-3-oxo-2,3-dihydropyridazin-6-yl]-2-phenylpyrazolo[1,5-a]pyridine was obtained in substantially the same manner as that of Example 114.

FT IR (KBr): 1729.8, 1664.3, 1635.3, 1591.0, 1529.3 cm$^{-1}$; NMR (CDCl$_3$, δ): 2.00–3.80 (6H, m), 5.80–5.95 (1H, m), 6.80 (1H, d, J=9.6 Hz), 6.89 (1H, t, J=6.9 Hz), 7.05 (1H, d, J=9.6 Hz), 7.26–7.65 (6H, m), 7.88 (1H, d, J=8.9 Hz), 8.51 (1H, d, J=6.9 Hz); (+)-APCI/MS: 386 (M$^+$+1).

EXAMPLE 116

To a solution of 3-[2-(2-oxopyrrolidin-3-yl)-3-oxo-2,3-dihydropyridazin-6-yl]-2-phenylpyrazolo[1,5-a]pyridine (740 mg) in N,N-dimethylformamide (5 ml) was added 60% sodium hydride in mineral oil (120 mg) at 0° C. After the mixture was stirred for 30 minutes, to this was added ethyl 2-bromoacetate (0.22 ml). After the reaction mixture was stirred at 0° C. for 1 hour, it was poured into water and extracted with ethyl acetate. The extract was washed with brine, dried over anhydrous sodium sulfate, and evaporated in vacuo. The crude material was purified by column chromatography on silica gel (CHCl$_3$—CHCl$_3$:MeOH (30:1)) to give 3-[2-(1-ethoxycarbonylmethyl-2-oxopyrrolidin-3-yl)-3-oxo-2,3-dihydropyridazin-6-yl]-2-phenylpyrazolo[1,5-a]pyridine (0.7 g) (yellow oil).

NMR (CDCl$_3$, δ): 1.29 (3H, t, J=7.1 Hz), 2.30–2.90 (2H, m), 3.50–3.80 (2H, m), 4.04 (1H, d, J=17.5 Hz), 4.22 (2H, q, J=7.1 Hz), 4.36 (1H, d, J=17.5 Hz), 5.93 (1H, t, J=9.2 Hz), 6.77 (1H, d, J=9.7 Hz), 6.90 (1H, t, J=7.0 Hz), 7.00 (1H, d, J=9.7 Hz), 7.26–7.34 (1H, m), 7.44–7.48 (3H, m), 7.59–7.64 (2H, m), 8.03 (1H, d, J=9.0 Hz), 8.50 (1H, d, J=7.0 Hz); (+)-APCI/MS: 458 (M$^+$+1).

EXAMPLE 117

3-[2-(1-Carboxymethyl-2-oxopiperidin-3-yl)-3-oxo-2,3-dihydropyridazin-6-yl]-2-phenylpyrazolo[1,5-a]pyridine was obtained according to similar manners to those of Examples 116 and 38.

mp: 145–150° C. (Et$_2$O); IR (Nujol): 1730, 1715, 1690, 1575, 1525 cm$^{-1}$; NMR (DMSO-d$_6$, δ): 1.90–2.30 (4H, m), 3.20–3.40 (2H, m), 3.90–4.39 (2H, m), 5.50–5.78 (1H, m), 6.80–7.20 (3H, m), 7.40–7.70 (6H, m), 7.80–8.10 (2H, m), 8.81 (1H, d, J=6.9 Hz); (+)-APCI/MS: 444 (M$^+$+1).

EXAMPLE 118

3-[2-(1-Methoxycarbonylmethoxy-5-oxo-5,6,7,8-tetrahydro-6-naphthyl)-3-oxo-2,3-dihydropyridazin-6-yl]-2-phenylpyrazolo[1,5-a]pyridine was obtained according to a similar manner to that of Example 2.

mp: 175–176° C. (AcOEt); IR (Nujol): 1740, 1700, 1665, 1630, 1595, 1525 cm$^{-1}$; NMR (DMSO-d$_6$, δ): 2.28–2.64 (1H, m), 2.74–3.21 (2H, m), 3.52 (1H, d, J=16.4 Hz), 4.74 (2H, s), 6.05 (1H, dd, J=4.7, 13.3 Hz), 6.81 (1H, d, J=7.2 Hz), 7.85 (1H, dd, J=1.3, 7.8 Hz), 6.96 (1H, d, J=7.5 Hz), 7.05 (1H, d, J=7.2 Hz), 7.16–7.36 (2H, m), 7.44–7.48 (3H, m), 7.61–7.66 (2H, m), 7.77–7.85 (2H, m), 8.48 (1H, d, J=6.9 Hz); (+)-APCI/MS: 521 (M$^+$+1). Analysis Calcd. for C$_{30}$H$_{24}$N$_4$O$_5$. 1/2H$_2$O: C, 68.05, H, 4.76, N, 10.58; Found: C, 68.45, H, 4.59, N, 10.57.

EXAMPLE 119

3-[2-(1-Carboxymethoxy-5-oxo-5,6,7,8-tetrahydro-6-naphthyl)-3-oxo-2,3-dihydropyridazin-6-yl]-2-phenylpyrazolo[1,5-a]pyridine was obtained according to a similar manner to that of Example 38.

mp: 225–227° C. (EtOH-CH$_2$Cl$_2$); IR (Nujol): 1740, 1695, 1635, 1560, 1530 cm$^{-1}$; NMR (DMSO-d$_6$, δ): 2.40–3.55 (4H, m), 4.81 (2H, s), 5.94 (1H, dd, J=3.5, 13 Hz), 6.97 (1H, d, J=9.7 Hz), 7.04 (1H, dt, J=1.3, 8.4 Hz), 7.17 (1H, d, J=9.7 Hz), 7.23 (1H, s), 7.32–7.59 (8H, m 7.78 (1H, d, J=8.9 Hz), 8.80 (1H, d, J=6.9 Hz); (+)-APCI/MS: 507 (M$^+$+1); Analysis Calcd. for C$_{29}$H$_{22}$N$_4$O$_5$. 1/2H$_2$O: C, 67.57, H, 4.50, N, 10.87; Found: C, 67.81, H, 4.76, N, 10.62.

What is claimed is:

1. A pyrazolopyridine compound of following formula:

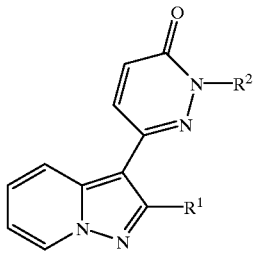

wherein

R$^1$ is aryl, and

R$^2$ is:

cyclo(lower)alkyl or cyclo(lower)alkenyl, each of which may have 1 to 3 suitable substituent(s) selected from the group consisting of oxo, lower alkylenedioxy group, hydroxy, lower alkanoyloxy, tri(lower)alkylsilyloxy, hydroxy(lower)alkyl, lower alkanoyl, carboxy, protected carboxy, hydroxysulfonyl, lower alkyl, lower alkylidene, lower alkanoyl(lower)alkyl, carboxy(lower)alkyl, protected carboxy(lower)alkyl, lower alkanoyl (lower)alkylidene, carboxy(lower)alkylidene, protected carboxy(lower)alkylidene, cyano, cyano (lower)alkyl, cyano(lower)alkylidene, lower alkylidene substituted with unsaturated 3 to 8-membered heteromonocyclic group containing 1 to 4 nitrogen atom(s) which may have 1 to 4 lower alkyl, lower alkylidene substituted with unsaturated 3 to 8-membered heteromonocyclic group containing 1 to 2 oxygen atom(s) and 1 to 3 nitrogen atom(s) which may have 1 to 4 lower alkyl, hydroxyimino, lower alkoxyimino, lower alkanoyl(lower)alkoxyimino, carboxy(lower)alkoxyimino, protected carboxy(lower)alkoxyimino, hydroxysulfonyl(lower)alkoxyimino, lower alkanoyloxyimino, and hydroxysulfonyloxyimino;

saturated 5 to 6-membered heterocyclic group containing a nitrogen or oxygen atom, which have oxo, and a suitable substituent selected from the group consisting of carboxy(lower)alkyl, lower alkoxycarbonyl(lower)alkyl and lower alkoxycarbonyl;

2,4-dioxo-1,2,3,4-tetrahydropyrimidin-6-yl, both nitrogen atoms of which have a suitable substituent selected from the group consisting of lower alkyl, carboxy(lower)alkyl and lower alkoxycarbonyl(lower)alkyl; or phenyl which may have lower alkoxy.

2. The compound of claim 1, wherein R¹ is phenyl.

3. A process for the preparation of the pyrazolopyridine compound of claim 1, or a salt thereof, which comprises:

1) reacting a compound of the formula:

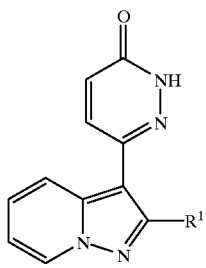

wherein R¹ is aryl,
or a salt thereof, with a compound of the formula:

R²—X wherein R² is as defined in claim 1, and
X is an acid residue,
or a salt thereof, or 2) subjecting a compound of the formula:

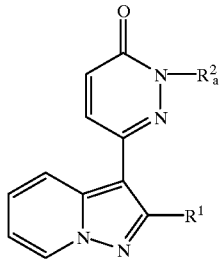

wherein
R¹ is aryl, and
R²ₐ is:
cyclo(lower)alkyl having oxo, which may have one or two suitable substituent(s);
cyclo(lower)alkenyl having oxo, which may have one or two suitable substituent(s);

wherein said suitable substituents are selected from the group consisting of oxo, lower alkylenedioxy group, hydroxy, lower alkanoyloxy, tri(lower)alkylsilyloxy, hydroxy(lower)alkyl, lower alkanoyl, carboxy, protected carboxy, hydroxysulfonyl, lower alkyl, lower alkylidene, lower alkanoyl(lower)alkyl, carboxy(lower)alkyl, protected carboxy(lower)alkyl, lower alkanoyl(lower)alkylidene, carboxy(lower)alkylidene, protected carboxy(lower)alkylidene, cyano, cyano(lower)alkyl, cyano(lower)alkylidene, lower alkylidene substituted with unsaturated 3 to 8-membered heteromonocyclic group containing 1 to 4 nitrogen atom(s) which may have 1 to 4 lower alkyl, lower alkylidene substituted with unsaturated 3 to 8-membered heteromonocyclic group containing 1 to 2 oxygen atom(s) and 1 to 3 nitrogen atom(s) which may have 1 to 4 lower alkyl, hydroxyimino, lower alkoxyimino, lower alkanoyl(lower)alkoxyimino, carboxy(lower)alkoxyimino, protected carboxy(lower)alkoxyimino, hydroxysulfonyl(lower)alkoxyimino, lower alkanoyloxyimino, and hydroxysulfonyloxyimino;

or a salt thereof, to a reduction reaction to give a compound of the formula:

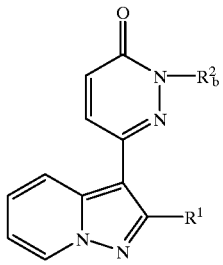

wherein
R¹ is aryl, and
R²_b is:
cyclo(lower)alkyl having hydroxy, which may have one or two suitable substituent(s); or
cyclo(lower)alkenyl having hydroxy, which may have one or two suitable substituent(s);
wherein said suitable substituents are selected from the group consisting of oxo, lower alkylenedioxy group, hydroxy, lower alkanoyloxy, tri(lower)alkylsilyloxy, hydroxy(lower)alkyl, lower alkanoyl, carboxy, protected carboxy, hydroxysulfonyl, lower alkyl, lower alkylidene, lower alkanoyl(lower)alkyl, carboxy(lower)alkyl, protected carboxy(lower)alkyl, lower alkanoyl(lower)alkylidene, carboxy(lower)alkylidene, protected carboxy(lower)alkylidene, cyano, cyano(lower)alkyl, cyano(lower)alkylidene, lower alkylidene substituted with unsaturated 3 to 8-membered heteromonocyclic group containing 1 to 4 nitrogen atom(s) which may have 1 to 4 lower alkyl, lower alkylidene substituted with unsaturated 3 to 8-membered heteromonocyclic group containing 1 to 2 oxygen atom(s) and 1 to 3 nitrogen atom(s) which may have 1 to 4 lower alkyl, hydroxyimino, lower alkoxyimino, lower alkanoyl(lower)alkoxyimino, carboxy (lower)alkoxyimino, protected carboxy(lower) alkoxyimino, hydroxysulfonyl(lower) alkoxyimino, lower alkanoyloxyimino, and hydroxysulfonyloxyimino;

or a salt thereof, or 3) reacting a compound of the formula:

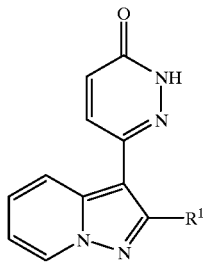

wherein R¹ is aryl,
or a salt thereof, with a compound of the formula:

wherein a compound of the formula:

is:
cyclo(lower)alkane having epoxy, which may have one or two suitable substituent(s);
cyclo(lower)alkene having epoxy, which may have one or two suitable substituent(s);
wherein said suitable substituents are selected from the group consisting of oxo, lower alkylenedioxy group, hydroxy, lower alkanoyloxy, tri(lower)alkylsilyloxy, hydroxy(lower)alkyl, lower alkanoyl, carboxy, protected carboxy, hydroxysulfonyl, lower alkyl, lower alkylidene, lower alkanoyl(lower)alkyl, carboxy(lower)alkyl, protected carboxy(lower)alkyl, lower alkanoyl(lower)alkylidene, carboxy(lower)alkylidene, protected carboxy(lower)alkylidene, cyano, cyano(lower)alkyl, cyano(lower)alkylidene, lower alkylidene substituted with unsaturated 3 to 8-membered heteromonocyclic group containing 1 to 4 nitrogen atom(s) which may have 1 to 4 lower alkyl, lower alkylidene substituted with unsaturated 3 to 8-membered heteromonocyclic group containing 1 to 2 oxygen atom(s) and 1 to 3 nitrogen atom(s) which may have 1 to 4 lower alkyl, hydroxyimino, lower alkoxyimino, lower alkanoyl(lower)alkoxyimino, carboxy(lower)alkoxyimino, protected carboxy(lower)alkoxyimino, hydroxysulfonyl(lower) alkoxyimino, lower alkanoyloxyimino, and hydroxysulfonyloxyimino;

to give a compound of the formula:

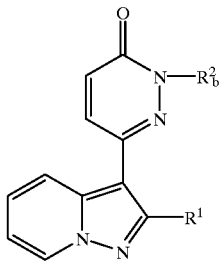

wherein
R¹ is aryl, and
R²$_b$ is as defined above
or a salt thereof, or 4) subjecting a compound of the formula:

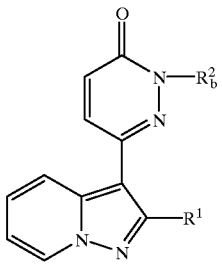

wherein R¹ is aryl, and
R²$_b$ is as defined above,
or a salt thereof, to oxidation reaction, to give a compound of the formula:

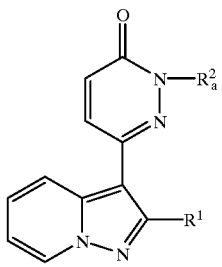

wherein R¹ and R²$_a$ are each as defined above, or a salt thereof, or 5) subjecting a compound of the formula:

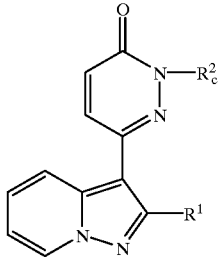

wherein
R¹ is aryl, and
R²$_c$ is:

cyclo(lower)alkyl having oxo, which may have one or two suitable substituent(s); or
cyclo(lower)alkenyl having oxo, which may have one or two suitable substituent(s),
or a salt thereof,
wherein said suitable substituents are selected from the group consisting of oxo, lower alkylenedioxy group, hydroxy, lower alkanoyloxy, tri(lower)alkylsilyloxy, hydroxy(lower)alkyl, lower alkanoyl, carboxy, protected carboxy, hydroxysulfonyl, lower alkyl, lower alkylidene, lower alkanoyl(lower)alkyl, carboxy(lower)alkyl, protected carboxy(lower)alkyl, lower alkanoyl(lower)alkylidene, carboxy(lower)alkylidene, protected carboxy(lower)alkylidene, cyano, cyano(lower)alkyl, cyano(lower)alkylidene, lower alkylidene substituted with unsaturated 3 to 8-membered heteromonocyclic group containing 1 to 4 nitrogen atom(s) which may have 1 to 4 lower alkyl, lower alkylidene substituted with unsaturated 3 to 8-membered heteromonocyclic group containing 1 to 2 oxygen atom(s) and 1 to 3 nitrogen atom(s) which may have 1 to 4 lower alkyl, hydroxyimino, lower alkoxyimino, lower alkanoyl(lower)alkoxyimino, carboxy(lower)alkoxyimino, protected carboxy(lower)alkoxyimino, hydroxysulfonyl(lower)alkoxyimino, lower alkanoyloxyimino, and hydroxysulfonyloxyimino;
to a Wittig type reaction to give a compound of the formula:

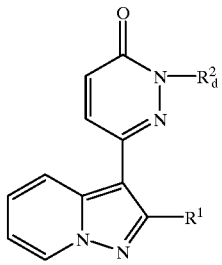

wherein
$R^1$ is aryl, and
$R^2_d$ is:
cyclo(lower)alkyl having lower alkylidene, which may have one or two suitable substituent(s);
cyclo(lower)alkyl having cyano(lower)alkylidene, which may have one or two suitable substituent(s);
cyclo(lower)alkenyl having lower alkylidene, which may have one or two suitable substituent(s);
cyclo(lower)alkenyl having cyano(lower)alkylidene, which may have one or two suitable substituent(s); or
a salt thereof,
wherein said suitable substituents are selected from the group consisting of oxo, lower alkylenedioxy group, hydroxy, lower alkanoyloxy, tri(lower)alkylsilyloxy, hydroxy(lower)alkyl, lower alkanoyl, carboxy, protected carboxy, hydroxysulfonyl, lower alkyl, lower alkylidene, lower alkanoyl(lower)alkyl, carboxy(lower)alkyl, protected carboxy(lower)alkyl, lower alkanoyl(lower)alkylidene, carboxy(lower)alkylidene, protected carboxy(lower)alkylidene, cyano, cyano(lower)alkyl, cyano(lower)alkylidene, lower alkylidene substituted with unsaturated 3 to 8-membered heteromonocyclic group containing 1 to 4 nitrogen atom(s) which may have 1 to 4 lower alkyl, lower alkylidene substituted with unsaturated 3 to 8-membered heteromonocyclic group containing 1 to 2 oxygen atom(s) and 1 to 3 nitrogen atom(s) which may have 1 to 4 lower alkyl, hydroxyimino, lower alkoxyimino, lower alkanoyl(lower)alkoxyimino, carboxy(lower)alkoxyimino, protected carboxy(lower)alkoxyimino, hydroxysulfonyl(lower)alkoxyimino, lower alkanoyloxyimino, and hydroxysulfonyloxyimino; or 6) subjecting a compound of the formula:

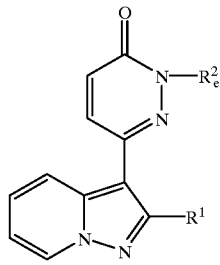

wherein
$R^1$ is aryl, and
$R^2_c$ is:
cyclo(lower)alkyl having protected carboxy, which may have one or two suitable substituent(s);
cyclo(lower)alkyl having protected carboxy(lower)alkyl, which may have one or two suitable substituent(s);
cyclo(lower)alkyl having protected carboxy(lower)alkylidene, which may have one or two suitable substituents;
cyclo(lower)alkyl having protected carboxy(lower)alkoxyimino, which may have one or two suitable substituent(s);
cyclo(lower)alkenyl having protected carboxy, which may have one or two suitable substituent(s);
cyclo(lower)alkenyl having protected carboxy(lower)alkyl, which may have one or two suitable substituent(s);
cyclo(lower)alkenyl having protected carboxy(lower)alkylidene, which may have one or two suitable substituent(s); or
cyclo(lower)alkenyl having protected carboxy(lower)alkoxyimino, which may have one or two suitable substituent(s);
or a salt thereof,
wherein said suitable substituents are selected from the group consisting of oxo, lower alkylenedioxy group, hydroxy, lower alkanoyloxy, tri(lower)alkylsilyloxy, hydroxy(lower)alkyl, lower alkanoyl, carboxy, protected carboxy, hydroxysulfonyl, lower alkyl, lower alkylidene, lower alkanoyl(lower)alkyl, carboxy(lower)alkyl, protected carboxy(lower)alkyl, lower alkanoyl(lower)alkylidene, carboxy(lower)alkylidene, protected carboxy(lower)alkylidene, cyano, cyano(lower)alkyl, cyano(lower)alkylidene, lower alkylidene substituted with unsaturated 3 to 8-membered heteromonocyclic group containing 1 to 4 nitrogen atom(s) which may have 1 to 4 lower alkyl, lower alkylidene substituted with unsaturated 3 to 8-membered heteromonocyclic group containing 1 to 2 oxygen atom(s) and 1 to 3 nitrogen atom(s) which may have 1 to 4 lower alkyl, hydroxyimino, lower alkoxyimino, lower alkanoyl(lower)alkoxyimino, carboxy(lower)alkoxyimino, protected carboxy(lower)alkoxyimino, hydroxysulfonyl(lower)alkoxyimino, lower alkanoyloxyimino, and hydroxysulfonyloxyimino;

to elimination reaction of carboxy protective group to give a compound of the formula:

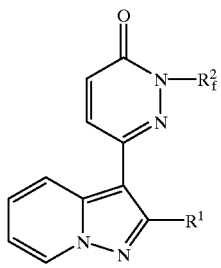

wherein
R$^1$ is aryl, and
R$^2_f$ is:
- cyclo(lower)alkyl having carboxy, which may have one or two suitable substituent(s);
- cyclo(lower)alkyl having carboxy(lower)alkyl, which may have one or two suitable substituent(s);
- cyclo(lower)alkyl having carboxy(lower)alkylidene, which may have one or two suitable substituent(s);
- cyclo(lower)alkyl having carboxy(lower)alkoxyimino, which may have one or two suitable substituent(s);
- cyclo(lower)alkenyl having carboxy, which may have one or two suitable substituent(s);
- cyclo(lower)alkenyl having carboxy(lower)alkyl, which may have one or two suitable substituent(s);
- cyclo(lower)alkenyl having carboxy(lower)alkylidene, which may have one or two suitable substituent(s); or
- cyclo(lower)alkenyl having carboxy(lower)alkoxyimino, which may have one or two suitable substituent(s);
- wherein said suitable substituents are selected from the group consisting of oxo, lower alkylenedioxy group, hydroxy, lower alkanoyloxy, tri(lower)alkylsilyloxy, hydroxy(lower)alkyl, lower alkanoyl, carboxy, protected carboxy, hydroxysulfonyl, lower alkyl, lower alkylidene, lower alkanoyl(lower)alkyl, carboxy(lower)alkyl, protected carboxy(lower)alkyl, lower alkanoyl(lower)alkylidene, carboxy(lower)alkylidene, protected carboxy(lower)alkylidene, cyano, cyano(lower)alkyl, cyano(lower)alkylidene, lower alkylidene substituted with unsaturated 3 to 8-membered heteromonocyclic group containing 1 to 4 nitrogen atom(s) which may have 1 to 4 lower alkyl, lower alkylidene substituted with unsaturated 3 to 8-membered heteromonocyclic group containing 1 to 2 oxygen atom(s) and 1 to 3 nitrogen atom(s) which may have 1 to 4 lower alkyl, hydroxyimino, lower alkoxyimino, lower alkanoyl(lower)alkoxyimino, carboxy(lower)alkoxyimino, protected carboxy(lower)alkoxyimino, hydroxysulfonyl(lower)alkoxyimino, lower alkanoyloxyimino, and hydroxysulfonyloxyimino;

or a salt thereof; or 7) subjecting a compound of the formula:

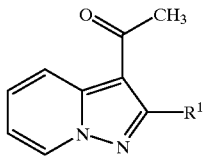

wherein R$^1$ is aryl,
or a salt thereof, to cyclization reaction to give a compound of the formula:

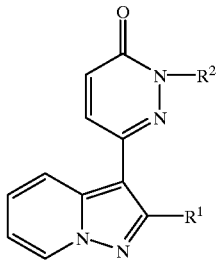

wherein R$^2$ is as defined in claim 1,
or a salt thereof, or 8) subjecting a compound of the formula:

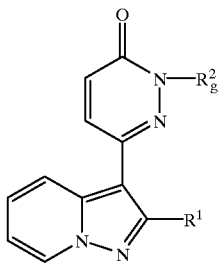

wherein
R$^1$ is aryl, and
R$^2_g$ is:
- cyclo(lower)alkyl having carboxy(lower)alkyl, which may have one or two suitable substituent(s);
- cyclo(lower)alkyl having carboxy(lower)alkylidene, which may have one or two suitable substituent(s);
- cyclo(lower)alkenyl having carboxy(lower)alkyl, which may have one or two suitable substituent(s);
- cyclo(lower)alkenyl having carboxy(lower)alkylidene, which may have one or two suitable substituent(s);
- or its reactive derivative at the carboxy group or a salt thereof,
- wherein said suitable substituents are selected from the group consisting of oxo, lower alkylenedioxy group, hydroxy, lower alkanoyloxy, tri(lower)alkylsilyloxy, hydroxy(lower)alkyl, lower alkanoyl, carboxy, protected carboxy, hydroxysulfonyl, lower alkyl, lower alkylidene, lower alkanoyl(lower)alkyl, carboxy (lower)alkyl, protected carboxy(lower)alkyl, lower alkanoyl(lower)alkylidene, carboxy(lower) alkylidene, protected carboxy(lower)alkylidene, cyano, cyano(lower)alkyl, cyano(lower)alkylidene, lower alkylidene substituted with unsaturated 3 to 8-membered heteromonocyclic group containing 1 to 4 nitrogen atom(s) which may have 1 to 4 lower alkyl, lower alkylidene substituted with unsaturated 3 to 8-membered heteromonocyclic group containing 1 to 2 oxygen atom(s) and 1 to 3 nitrogen atom(s) which may have 1 to 4 lower alkyl, hydroxyimino, lower alkoxyimino, lower alkanoyl(lower) alkoxyimino, carboxy(lower)alkoxyimino, protected carboxy(lower)alkoxyimino, hydroxysulfonyl (lower)alkoxyimino, lower alkanoyloxyimino, and hydroxysulfonyloxyimino;

to amidation reaction to give a compound of the formula:

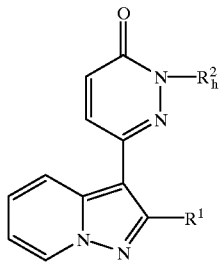

wherein
R$^1$ is aryl, and
R$^2_h$ is cyclo(lower)alkyl having amidated carboxy (lower)alkyl, which may have one or two suitable substituent(s);
cyclo(lower)alkyl having amidated carboxy (lower)alkylidene, which may have one or two suitable substituent(s);
cyclo(lower)alkenyl having amidated carboxy (lower)alkyl, which may have one or two suitable substituent(s);
cyclo(lower)alkenyl having amidated carboxy (lower)alkylidene, which may have one or two suitable substituent(s); or a salt thereof,
wherein said suitable substituents are selected from the group consisting of oxo, lower alkylenedioxy group, hydroxy, lower alkanoyloxy, tri(lower)alkylsilyloxy, hydroxy(lower)alkyl, lower alkanoyl, carboxy, protected carboxy, hydroxysulfonyl, lower alkyl, lower alkylidene, lower alkanoyl(lower)alkyl, carboxy(lower)alkyl, protected carboxy (lower)alkyl, lower alkanoyl(lower)alkylidene, carboxy(lower)alkylidene, protected carboxy (lower)alkylidene, cyano, cyano(lower)alkyl, cyano(lower)alkylidene, lower alkylidene substituted with unsaturated 3 to 8-membered heteromonocyclic group containing 1 to 4 nitrogen atom(s) which may have 1 to 4 lower alkyl, lower alkylidene substituted with unsaturated 3 to 8-membered heteromonocyclic group containing 1 to 2 oxygen atom(s) and 1 to 3 nitrogen atom(s) which may have 1 to 4 lower alkyl, hydroxyimino, lower alkoxyimino, lower alkanoyl(lower)alkoxyimino, carboxy (lower)alkoxyimino, protected carboxy(lower) alkoxyimino, hydroxysulfonyl(lower) alkoxyimino, lower alkanoyloxyimino, and hydroxysulfonyloxyimino.

4. A pharmaceutical composition or medicament comprising:
the compound of claim 1 or a pharmaceutically acceptable salt thereof in admixture with a pharmaceutically acceptable carrier or excipient.

5. A method of manufacturing a pharmaceutical composition or a medicament comprising admixing the compound of claim 1 or a pharmaceutically acceptable salt thereof with a pharmaceutically acceptable carrier or excipient.

6. The pharmaceutical composition or medicament of claim 4, in the form of a tablet, pellet, troche, capsule, suppository, cream, ointment, aerosol, powder, solution, emulsion, or suspension.

7. A method for the treatment of depression; dementia; anxiety; pain; cerebrovascular disease; heart failure; hypertension; circulatory insufficiency; post-resuscitation asystole; bradyarrhythmia; electro-mechanical dissociation; hemodynamic collapse; SIRS (systemic inflammatory response syndrome); multiple organ failure; renal failure (renal insufficiency); renal toxicity; nephrosis; nephritis; edema; obesity; bronchial asthma; gout; hyperuricemia; sudden infant death syndrome; immunosuppression; diabetes; ulcer; pancreatitis; Meniere's syndrome; anemia; myocardial infarction; thrombosis; obstruction; arteriosclerosis obliterans; thrombophlebitis; cerebral infarction; transient ischemic attack; or angina pectoris;
that comprises administering a therapeutically effective amount of a compound of claim 1 or a pharmaceutically acceptable salt thereof to a subject in need thereof.

* * * * *